United States Patent [19]

Baker et al.

[11] Patent Number: 5,545,734
[45] Date of Patent: Aug. 13, 1996

[54] ARYL AND HETEROARYL MACROLIDES HAVING IMMUNOSUPPRESSIVE ACTIVITY

[75] Inventors: Robert K. Baker, Cranford; Gerard R. Kieczykowski, Westfield; Hyun O. Ok; William H. Parsons, both of Edison; Kathleen M. Rupprecht, Cranford, all of N.J.

[73] Assignee: Merck & Co., Inc., Rahway, N.J.

[21] Appl. No.: 328,225

[22] Filed: Oct. 25, 1994

[51] Int. Cl.$^6$ ............................................. C07D 498/16
[52] U.S. Cl. ................................. 540/456; 540/450
[58] Field of Search ........................ 540/456; 514/291; 518/411

[56] References Cited

FOREIGN PATENT DOCUMENTS

| | | | |
|---|---|---|---|
| 0427680A1 | 5/1991 | European Pat. Off. | 540/456 |
| 2244991 | 12/1991 | United Kingdom | 540/456 |
| 2245891 | 1/1992 | United Kingdom | 540/456 |

*Primary Examiner*—John M. Ford
*Assistant Examiner*—Pavanaram K. Sripada
*Attorney, Agent, or Firm*—J. Eric Thies; David L. Rose

[57] ABSTRACT

Aryl and heteroaryl macrolides of the general structural Formula I:

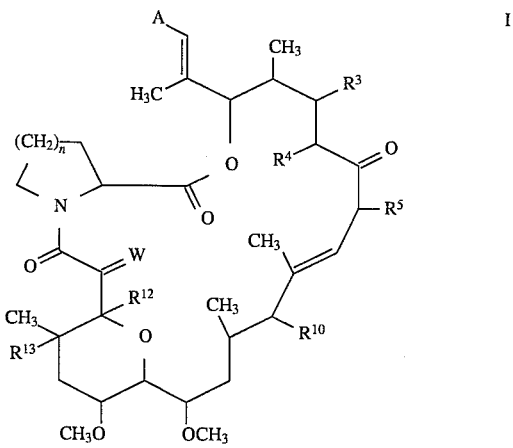

have been prepared from suitable precursors by olefination at C-27. These macrolide immunosuppressants are useful in a mammalian host for the treatment of autoimmune diseases, infectious diseases, the prevention of rejection of foreign organ transplants and/or related afflictions, diseases, and illnesses.

9 Claims, No Drawings

ARYL AND HETEROARYL MACROLIDES HAVING IMMUNOSUPPRESSIVE ACTIVITY

SUMMARY OF THE INVENTION

The present invention is related to aryl and heteroaryl macrolides which are useful in a mammalian subject for the treatment of autoimmune diseases (such as juvenile-onset or recent-onset diabetes mellitus, multiple sclerosis, and rheumatoid arthritis, liver disease, posterior uveitis, allergic encephalomyelitis, and glomerulonephritis), immunodepression, infectious diseases and/or the prevention of rejection of foreign organ transplants, (e.g. bone marrow, kidney, liver, heart, skin, small-bowel, and pancreatic islet-cell transplants, including xeno transplants), the topical treatment of inflammatory and hyperproliferative skin diseases and cutaneous manifestations of immunologically-mediated illnesses (such as: psoriasis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, Lupus erythematosus or Alopecia areata), male pattern alopecia, alopecia senilis, reversible obstructive airways disease, particularly asthma, inflammation of mucosa and blood vessels, cytomegalovirus infection, multidrag resistance, idiopathic thromboytopenic purpura, Behcet's syndrome, conjunctivitis, Crohn's disease, Mooren's ulcer, uveitis, servere intraocular inflammation and/or hepatic injury associated with ischemia. The present compounds are further useful in combination with a 5α-reductase inhibitor, a cyclosporin, a potassium channel opener or a phospholipid in a mammalian host for the treatment of baldness, especially male pattern alopecia, female pattern alopecia, alopecia senilis, or alopecia areata. In addition, some of the compounds of this invention may have antagonistic properties and so have utility in the reversal of immunosuppressive activity and/or diminishing the toxicity of other immunosuppressive agents.

More particularly, this invention relates to compounds of the general structural Formula I:

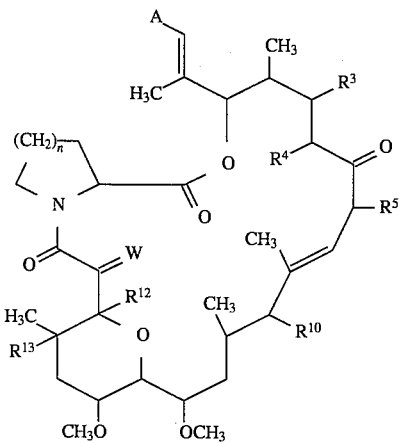

wherein $R^3$, $R^4$, $R^5$, $R^{10}$, $R^{12}$, $R^{13}$, A, W, and n are hereinafter defined.

This invention also relates to pharmaceutical compositions containing the compounds and to a method of use of the present compounds and other agents for the treatment of and prevention of certain afflictions, diseases and illnesses.

BRIEF DESCRIPTION OF DISCLOSURES IN THE ART

Fujisawa United States, European and Japanese patents and applications (U.S. Pat. No. 4,894,366, issued Jan. 16, 1990, EPO Publication No. 0,184,162 and PBJ Disclosure 63-17884) and publications (*J. Am. Chem. Soc.,* 1987, 109, 5031 and *J. Antibiotics* 1987, 40, 1249) disclose 17-allyl-1, 14-dihydroxy-12-[2'-(4"-hydroxy- 3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene- 2,3, 10,16-tetraone (FR-900506) (FK-506) (L-679,934), 17-ethyl-1,14-dihydroxy- 12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (FR-900520) and related compounds which are the starting materials for the preparation of the compounds described. The synthetic preparation of the aforementioned starting material (FR-900506) has been reported (*J. Am. Chem. Soc.,* 1989, 111, 1157). A Sandoz U.S. patent (U.S. Pat. No. 5,011,844) and European patent application (EPO Publication No. 0,356,399) disclose stereoisomers of FR-900506 and derivatives at the 17-position. Fisons European and WIPO patent applications (EPO Publication No. 0,323,042 and PCT Publication No. WO89/05304) disclose various derivatives of FR-900506, FR-900520 and related compounds. A Sandoz European patent application (EPO Publication No. 0,437,680) discloses chloro, bromo, iodo and azido derivatives of FR-900506, FR-900520 and related compounds. A Merck European patent application (EPO Publication No. 0,428, 365) discloses various amino derivatives of FR-900506, FR-900520 and related compounds. A Fujisawa UK patent application (UK Publication No. GB 2,245,891A) discloses various aryl(lower alkyl) and heteroaryl derivatives of FR-900506, FR-900520 and related compounds. Merck U.S. Pat. Nos. 5,247,076, 5,250,678 and 5,252,732 disclose various aryl and heteroaryl derivatives of FR-900506, FR-900520 and related compounds. Merck U.S. Pat. No. 5,284,877 discloses C-17 alkyl and alkenyl derivatives of FR-900506, FR-900520 and related compounds.

Fujisawa United States patents (U.S. Pat. No. 4,929,611, issued May 29, 1990 and U.S. Pat. No. 4,956,352, issued Sep. 11, 1990) disclose the use of FK-506-type compounds in treating resistance to transplantation. A Sandoz European patent application (EPO Publication No. 0,315,978) discloses the use of FR-900506 and related compounds in the topical treatment of inflammatory and hyperproliferative skin diseases and of cutaneous manifestations of immunologically-mediated illness. A Fisons World patent application (PCT Publication WO 90/14826) discloses the use of FR-900506 and related compounds in the treatment of reversible obstructive airways disease, particularly asthma. A Fujisawa European patent application (EPO Publication No. 0,423,714) discloses the use of FK-506 and derivatives as hair revitalizing agents. Various studies have suggested the efficacy of FK-506 in the treatment of a number of ailments, including rheumatoid arthritis (C. Arita, et al., *Clinical exp. Immunol.,* 1990, 82, 456–461; N. Inamura, et al., *Clin. Immunol. Immunopathol.* 1988, 46, 82–90), recent-onset diabetes (N. Murase, et al., *Diabetes,* 1990, 39, 1584–86; N. Murase, et al., *Lancet,* 1990, 336, 373–74), posterior uveitis (H. Kawashima, *Invest. Ophthalmul. Vis. Sci.,* 1988, 29, 1265–71), hepatic injury associated with ischemia (M. Sakr, et al., *Life Sci.,* 1990, 47, 687–91) allergic encephalomyelitis (K. Deguchi, et al., *Brain Nerve,* 1990, 42, 391–97), glomerulonephritis (J. McCauley, et al., *Lancet,* 1990, 335, 674), systemic lupus erythematosus (K. Takabayashi, et al., *Clin. Immunol. Immunopathol.,* 1989, 51, 110–117), multidrug resistance (M. Naito, et al., *Cancer Chemother. Pharmacol.,* 1992, 29, 195–200), inflammation of mucosa and blood vessels (PCT Publication WO 91/17754), cytomegalovirus infection (UK Publication GB 2,247,620A), and idiopathic thrombocytopenic purpura and Basedow's disease (PCT Publication WO 91/19495).

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, and Graves ophthalmopathy. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Antiinflammatory agents such as NSAID's and corticosteroids act principally by blocking the effect or secretion of these mediators but do nothing to modify the immunologic basis of the disease. On the other hand, cytotoxic agents such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A which was approved by the US FDA in 1983 is currently the leading drug used to prevent rejection of transplanted organs. The drug acts by inhibiting the body's immune system from mobilizing its vast arsenal of natural protecting agents to reject the transplant's foreign protein. Though cyclosporin A is effective in fighting transplant rejection, it is nephrotoxic and is known to cause several undesirable side effects including kidney failure, abnormal liver function and gastrointestinal discomfort.

Newer, safer drugs exhibiting less side effects are constantly being searched for in the field.

The 23-membered tricyclo-macrolide immunosuppressant, tacrolimus, FR-900506, FK-506,

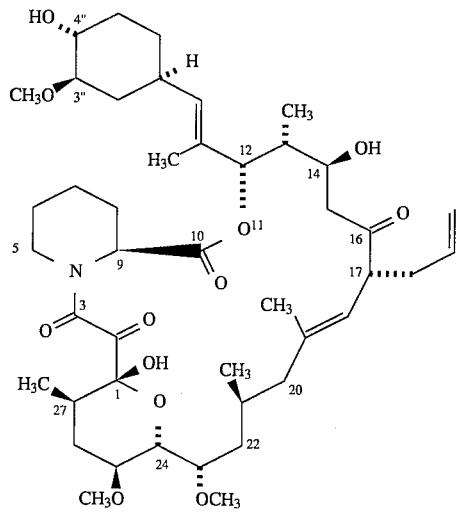

(17-allyl-1,14-dihydroxy-12-[2'-(4"-hydroxy-3"-methoxycyclohexyl)- 1'-methylvinyl]-23,25-dimethoxy-13,19,21, 27-tetramethyl-11,28-dioxa- 4-azatricyclo-[22.3.1.0$^{4,9}$]octacos-18-ene-2,3,10,16-tetraone) and related compounds which were isolated and characterized by Tanaka, Kuroda, and co-workers at Fujisawa Pharmaceutical Co. in Japan, see *J. Am. Chem. Soc.,* 1987, 109, 5031, and U.S. Pat. No. 4,894,366, issued Jan. 16, 1990) have been shown to possess exceptional immunosuppressive activity. Fujisawa United States patents (U.S. Pat. No. 4,929,611, issued May 29, 1990, U.S. Pat. No. 4,956,352, issued Sep. 11, 1990 and U.S. Pat. No. 5,110,811, issued May 5, 1992) disclose the use of FK-506-type compounds in treating resistance to transplantation. In particular, the compound FR-900506 has been reported to be 100 times more effective than cyclosporin in the supression of in vitro immune systems (*J. Antibiotics* 1987, 40, 1256). In addition, these compounds are reputed to possess topical activity in the treatment of inflammatory and hyperproliferative skin diseases and cutaneous manifestations of immunologically-mediated illnesses (EPO Pub. No. 0,315,978).

The compound FK-506 and related compounds further have been suggested to be useful in the treatment of obstructive airways disease, particularly asthma (PCT Publication WO 90/14826), male pattern alopecia or alopecia senilis (EPO Publication No. 0,423,71.4), rheumatoid arthitis (C. Arita, et al., *Clinical exp. Immunol.,* 1990, 82, 456–461; N. Inamura, et al., *Clin. Immunol. Immunopathol.* 1988, 46, 82–90), recent-onset diabetes (N. Murase, et al., *Diabetes,* 1990, 39, 1584–86; N. Murase, et al., *Lancet,* 1990, 336, 373–74), posterior uveitis (H. Kawashima, *Invest. Ophthalmol. Vis. Sci.,* 1988, 29, 1265–71), hepatic injury associated with ischemia (M. Sakr, et al., *Life Sci.,* 1990, 427, 687–91) allergic encephalomyelitis (K, Deguchi, et al., *Brain Nerve,* 1990, 42, 391–97), glomerulonephritis (J. McCauley, et al., *Lancet,* 1990, 335, 674), systemic lupus erythematosus (K. Takabayashi, et al., *Clin. Immunol. Immunopathol.,* 1989, 51, 110–117) multidrug resistance (M. Naito, et al., *Cancer Chemother. Pharmacol.,* 1992, 29, 195–200), inflammation of mucosa and blood vessels (PCT Publication WO 92/17754), cytomegalovirus infection (UK Publication GB 2,247,620A), and idiopathic thrombocytophenic purpura and Basedow's disease (PCT Publication WO 91/19495).

DETAILED DESCRIPTION OF THE INVENTION

A. Scope of the Invention

The novel compound of this invention has structural Formula I:

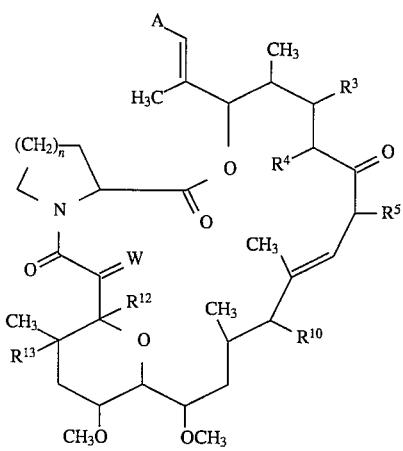

or a pharmaceutically acceptable salt thereof, wherein:
A is selected from the group consisting of:
 (1) Ar—B—, and
 (2) Ar—B—Ar'—;
Ar is selected from the group consisting of:
 (1) phenyl,
 (2) substituted phenyl in which the substituents are X, Y, and Z,
 (3) heteroaryl, and
 (4) substituted heteroaryl in which the substituents are X, Y, and Z;
Ar' is selected from the group consisting of:
 (1) phenyl,
 (2) substituted phenyl in which the substituents are X, Y, and Z,
 (3) heteroaryl, and
 (4) substituted heteroaryl in which the substituents are X, Y, and Z;
B is a bond or is selected from the group consisting of:
 —O—,
 (2) —NR$^6$—, wherein R$^6$ is as defined below,
 (3) —S(O)p—, wherein p is 0, 1 or 2,
 (4) C$_{1-10}$alkyl,
 (5) substituted C$_{1-10}$alkyl in which the alkyl portion may be substituted with one or more of the substituent(s) selected from:
  (a) hydroxy,
  (b) oxo,
  (c) C$_{1-6}$alkoxy,
  (d) phenyl-C$_{1-3}$ alkoxy,
  (e) substituted phenyl-C$_{1-3}$alkoxy, in which the substituents on phenyl are X, Y and Z,
  (f) unsubstituted or substituted phenyloxy, in which the substituents on phenyl are X, Y and Z,
  (g) —OCO—C$_{1-6}$alkyl,
  (h) —NR$^6$R$^7$, wherein R$^6$ and R$^7$ are independently selected from:
   (i) hydrogen,
   (ii) C$_{1-10}$alkyl unsubstituted or substituted with
    (a') phenyl, which is unsubstituted or substituted with X, Y and Z,
    (b') —OH,
    (c') C$_{1-6}$alkoxy,
    (d') —CO$_2$H,
    (e') —CO$_2$C$_{1-6}$alkyl,
    (f') —C$_{3-7}$cycloalkyl,
    (g') —OR$^{11}$
   (iii) C$_{3-10}$alkenyl unsubstituted or substituted with one or more of the substituent(s) selected from:
    (a') aryl, which is unsubstituted or substituted with X, Y and Z,
    (b') heteroaryl, which is unsubstituted or substituted with X, Y and Z,
    (c') —OH,
    (d') C$_{1-6}$alkoxy,
    (e') —CO$_2$H,
    (f') —CO$_2$—C$_{1-6}$alkyl,
    (g') —C$_{3-7}$cycloalkyl, and
    (h') —OR$^{11}$,
   (iv) or where R$^6$ and R$^7$ and the N to which they are attached may form an unsubstituted or substituted 3–7-membered heterocyclic ring which may include one or two additional heteroatoms independently selected from the group consisting of O, S(O)p, NR$^{14}$, wherein R$^{14}$ is hydrogen or C$_{1-6}$alkyl unsubstituted or substituted by phenyl, and p is 0, 1 or 2, such as morpholine, thiomorpholine, piperidine, or piperizine,
   (i) —NR$^6$CO—C$_{1-6}$alkyl-R$^7$ wherein R$^6$ and R$^7$ are as defined above,
   (j) —NR$^6$CO$_2$—C$_{1-6}$alkyl-R$^7$,
   (k) —NR$^6$CONR$^6$R$^7$,
   (l) —OCONR$^6$R$^7$,
   (m) —COOR$^6$,
   (n) —CHO,
   (o) phenyl,
   (p) substituted phenyl in which the substituents are X, Y and Z
   (q) —OR$^{11}$ and
   (r) —S(O)$_p$—C$_{1-6}$alkyl,
 (6) C$_{1-10}$alkyl wherein one or more of the alkyl carbons is replaced by a group selected from: —NR$^6$—, —O—, —S(O)$_p$—, —CO$_2$—, —O$_2$C—, —CONR$^6$—, —NR$^6$CO—, —NR$^6$CONR$^7$—,
 (7) substituted C$_{1-10}$alkyl wherein one or more of the alkyl carbons is replaced by a group selected from: —NR$^6$—, —O—, —S(O)$_p$—, —CO$_2$—, —O$_2$C—, —CONR$^6$—, —N$^6$CO— and —NR$^6$CONR$^7$—, and the alkyl group may be substituted by one or more of the substituent(s) selected from:
  (a) hydroxy,
  (b) oxo,
  (c) C$_{1-6}$alkoxy,
  (d) phenyl-C$_{1-3}$alkoxy,
  (e) substituted phenyl-C$_{1-3}$alkoxy, in which the substituents on phenyl are X, Y and Z,
  (f) unsubstituted or substituted phenyloxy, in which the substituents on phenyl are X, Y and Z,
  (g) —OCO—C$_{1-6}$alkyl,
  (h) —NR$^6$R$^7$, wherein R$^6$ and R$^7$ are as defined above,
  (i) —NR$^6$CO—C$_{1-6}$alkyl-R$^7$,
  (j) —NR$^6$CO$_2$C$_{1-6}$alkyl-R$^6$,
  (k) —NR$^6$CONR$^6$R$^7$,
  (l) —OCONR$^6$R$^7$, (m) —COOR$^6$,
(n) —CHO,
(o) phenyl,
(p) substituted phenyl in which the substituents are X, Y and Z
(q) —OR$^{11}$ and
(r) —S(O)$_p$-C$_{1-6}$alkyl, (8) C$_{3-10}$alkenyl wherein alkenyl contains one to four double bonds, (9) C$_{3-10}$alkenyl wherein alkenyl contains one to four double bonds and wherein one or more of the alkyl carbons is replaced by a group selected from: —NR$^6$—, —O—, —S(O)$_p$—, —CO$_2$—, —O$_2$C—, —CONR$^6$—, —NR$^6$CO—, —NR$^6$CONR$^7$—,

(10) substituted C$_{3-10}$alkenyl wherein alkenyl contains one to four double bonds and wherein one or more of the alkyl carbons may be replaced by a group selected from: —NR$_6$—, —O—, —S(O)$_p$—, —CO$_2$—, —O$_2$C—, —CONR$^6$—, —NR$^6$CO—, —NR$^6$CONR$^7$, and the alkyl group may be substituted by one or more of the substituent(s) selected from:
(a) hydroxy,
(b) oxo,
(c) C$_{1-6}$alkoxy,
(d) phenylC$_{1-3}$alkoxy,
(e) substituted phenylC$_{1-3}$alkoxy, in which the substituents on phenyl are X, Y and Z,
(f) unsubstituted or substituted phenyloxy, in which the substituents on phenyl are X, Y and Z,
(g) —OCO—C$_{1-6}$alkyl,
(h) —NR$^6$R$^7$, wherein R$^6$ and R$^7$ are as defined above,
(i) —NR$^6$CO—C$_{1-6}$alkyl,
(j) —NR$^6$CO$_2$—Cl$_{1-6}$alkyl,
(k) —NR$^6$CONR$^6$R$^7$,
(l) —OCONR$^6$R$^7$,
(m) —COOR$^6$,
(n) —CHO,
(o) phenyl,
(p) substituted phenyl in which the substituents are X, Y and Z
(q) —OR$^{11}$ and
(r) —S(O)$_n$—C$_{1-6}$alkyl,

(11) C$_{3-10}$alkynyl wherein alkynyl contains one or two triple bonds,

(12) C$_{3-10}$alkynyl wherein alkynyl contains one or two triple bonds and wherein one or more of the alkyl carbons is replaced by a group selected from: —NR$^6$—, —O—, —S(O)$_p$—, —CO$_2$—, —O$_2$C—, —CONR$^6$—, —NR$^6$CO—, —NR$^6$CONR$^7$—,

(13) substituted C$_{3-10}$alkynyl wherein alkynyl contains one or two triple bonds and wherein one or more of the alkyl carbons is replaced by a group selected from: —NR$^6$—, —O—, —S(O)$_p$—, —CO$_2$—, —O$_2$C—, —CONR$^6$—, —NR$^6$CO—, —NR$^6$CONR$^7$, and Z, and the alkyl group may be substituted by one or more of the substituent(s) selected from:
(a) hydroxy,
(b) oxo,
(c) C$_{1-6}$alkoxy,
(d) phenyl-C$_{1-3}$alkoxy,
(e) substituted phenylC$_{1-3}$alkoxy, in which the substituents on phenyl are X, Y and Z,
(f) unsubstituted or substituted phenyloxy, in which the substituents on phenyl are X, Y and Z,
(g) —OCOR$_6$,
(h) —NR$^6$R$^7$, wherein R$^6$ and R$^7$ are as defined above,
(i) —NR$^6$CO—C$_{1-6}$alkyl,
(j) —NR$^6$CO$_2$—C$_{1-6}$alkyl,
(k) —NR$^6$CONR$^6$R$^7$,
(l) —OCONR$^6$R$^7$,
(m) —COOR$^6$,
(n) —CHO,
(o) phenyl,
(p) substituted phenyl in which the substituents are X, Y and Z
(q) —OR$^{11}$, and
(r) —S(O)$_p$—C$_{1-6}$alkyl;

R$^3$ is hydrogen, hydroxy, —OR$^{11}$, or C$_{1-6}$alkoxy;
R$^4$ is hydrogen, or R$^3$ and R$^4$ taken together form a double bond;
R$^5$ is methyl, ethyl, propyl, or allyl;
R$^{10}$ is hydrogen, hydroxy, —OR$_{11}$ or fluoro;
R$^{11}$ is selected from:
(a) —PO(OH)O—M+, wherein M+ is a positively charged inorganic or organic counterion,
(b) —SO$_3$—M+,
(c) —CO(CH$_2$)$_q$CO$_2$—M+, wherein q is 1–3, and
(d) —CO—C$_{1-6}$alkyl-NR$^6$R$^7$, wherein R$^6$ and R$^7$ are as defined above and the alkyl is unsubstituted or substituted with one or more substituents selected from:
(i) hydroxy,
(ii) C$_{1-6}$alkoxy,
(iii) —NR$^{17}$R$^{18}$, wherein R$^{17}$ and R$^{18}$ are independently selected from:
(a') hydrogen, and
(b') C$_{1-6}$alkyl,
(iv) —COOR$_6$, wherein R$^6$ is as defined above,
(v) phenyl,
(vi) substituted phenyl in which the substituents are X, Y and Z,
(vii) heteroaryl,
(viii) —SH, and
(ix) —S—C$_{1-6}$alkyl;
R$^{12}$ is hydroxy, or hydrogen;
R$^{13}$ is hydrogen, or R$^{12}$ and R$^{13}$ taken together form a double bond;
W is O or (H, OH);
X, Y and Z independently are selected from the group consisting of:
(a) hydrogen,
(b) C$_{1-10}$alkyl, unsubstituted or substituted with one or more substituents selected from:
(i) aryl,
(ii) substituted aryl in which the substituents are X', Y' and Z',
(iii) heteroaryl,
(iv) substituted heteroaryl in which the substituents are X', Y', and Z',
(v) unsubstituted or substituted aryloxy, in which the substituents on aryl are X', Y' and Z',
(vi) —OR$^6$,
(vii) —OR$^{11}$,
(viii) —OCOR$^6$,
(ix) —OCO$_2$R$^6$,
(x) —NR$^6$R$^7$,
(xi) —CHO,
(xii) —NR$^6$COC$_{1-6}$alkyl-R$^7$,
(xiii) —NR$^6$CO$_2$C$_{1-6}$alkyl-R$^7$,
(xiv) —NR$^6$CONR$^6$R$^7$,
(xv) —OCONR$^6$R$^7$, (xvi) —CONR$^6$R$^7$, (c) C$_{1-10}$alkyl wherein one or more of the alkyl carbons is replaced by a group selected from —NR$^6$—, —O—, —S(O)$_p$—, —CO$_2$—, —O$_2$C—, —CONR$^6$—, —NR$^6$CO—, —NR$^6$CONR$^7$—, —CO—, —CH(OH)—, alkenyl or alkynyl and the alkyl may be unsubstituted or substituted with one or more substituents selected from:
(i) aryl,
(ii) substituted aryl in which the substituents are X', Y' and Z',
(iii) heteroaryl,
(iv) substituted heteroaryl in which the substituents are X', Y', and Z',
(v) unsubstituted or substituted aryloxy, in which the substituents on aryl are X', Y', and Z',
(vi) —OR$^6$,
(vii) —OR$^{11}$,
(viii) —OCOR$^6$,
(ix) —OCO$_2$R$^6$,
(x) —NR$^6$R$^7$,
(xi) —CHO
(xii) —NR$^6$COC$_{1-6}$alkyl-R$^7$,
(xiii) —NR$^6$CO$_2$C$_{1-6}$alkyl-R$^7$,
(xiv) —NR$^6$CONR$^6$R$^7$,
(xv) —OCONR$^6$R$^7$,
(xvi) —CONR$^6$R$^7$,
(d) halogen,
(e) —NR$^6$R$^7$,
(f) —CN,
(g) —CHO,
(h) —CF$_3$,
(i) —SR$^8$, wherein R$^8$ is hydrogen, C$_{1-6}$alkyl, trifluoromethyl, or phenyl,
(j) —SOR$_8$,
(k) —SO$_2$R$^8$,
(l) —CONR$^6$R$^7$,
(m) R$^9$O(CH$_2$)$_m$— wherein R$^9$ is hydrogen, C$_{1-6}$alkyl, hydroxy-C$_{2-3}$alkyl, —CF$_3$, phenyl, R$^{11}$ or naphthyl and m is 0, 1, 2, or 3,
(n) —CH(OR$^{15}$)(OR$^{16}$), wherein R$^{15}$ and R$^{16}$ are C$_{1-3}$alkyl or taken together form an ethyl or propyl bridge,
(o)

wherein R$^9$ and m are as defined above,
(p)

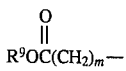

wherein R$^9$ and m are as defined above, and
(q) —R$^{11}$,
(r) aryl,
(s) substituted aryl in which the substituents are X', Y' and Z', or any two of X, Y and Z may be joined to form a saturated ring having 5, 6 or 7 ring atoms, said ring atoms comprising 1 or 2 oxygen atoms, the remaining ring atoms being carbon, such as dioxolanyl or dioxanyl;

X', Y' and Z' independently are selected from the group consisting of:
(a) hydrogen,
(b) C$_{1-7}$alkyl,
(c) C$_{2-6}$alkenyl,
(d) halogen,
(e) —(CH$_2$)$_m$—NR$^6$R$^7$, wherein R$^6$, R$^7$, and m are as defined above,
(f) —CN,
(g) —CHO,
(h) —CF$_3$,
(i) —SR$^8$, wherein R$^8$ is hydrogen, C$_{1-6}$alkyl, trifluoromethyl, or phenyl,
(j) —SOR$^8$, wherein R$^8$ is as defined above,
(k) —SO$_2$R$^8$, wherein R$^8$ is as defined above,
(l) —CONR$^6$R$^7$, wherein R$^6$ and R$^7$ are as defined above,
(m) R$^9$O(CH$_2$)$_m$— wherein R$^9$ and m are as defined above,
(n) —CH(OR$^{15}$)(OR$^{16}$), wherein R$^{15}$ and R$^{16}$ are as defined above,
(o)

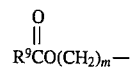

wherein R$^9$ and m are as defined above,
(p)

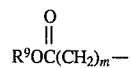

wherein R$^9$ and m are as defined above, and
(q) —R$^{11}$;
n is 1 or 2;
with the proviso that if: A is Ar—B—, Ar is substituted phenyl in which the substituents are X, Y and Z, B is a bond, X is hydrogen, and Y is HO—, then Z is other than CH$_3$O— or R$^9$CO$_2$, wherein R$^9$ is a defined above.

The compounds of the present invention have asymmetric centers and this invention includes all of the optical isomers and mixtures thereof.

In addition compounds with carbon—carbon double bonds may occur in Z- and E- forms with all isomeric forms of the compounds being included in the present invention.

When any variable (e.g., alkyl, aryl, R$^6$, R$^7$, R$^8$, R$^9$, R$^{10}$ etc.) occurs more than one time in any variable or in Formula I, its definition on each ocurrence is independent of its definition at every other occurrence.

As used herein, the term "alkyl" includes those alkyl groups of a designated number of carbon atoms of either a straight, branched, or cyclic configuration. Examples of "alkyl" include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentoxy.

"Alkenyl" is intended to include hydrocarbon chains of a specified number of carbon atoms of either a straight- or branched-configuration and at least one unsaturation, which may occur at any point along the chain, such as ethenyl, propenyl, butenyl, pentenyl, dimethylpentyl, and the like, and includes E and Z forms, where applicable; and "heteroarylalkyl" represents heteroaryl groups as herein defined which are attached through a straight or branched chain alkyl group of from one to ten carbon atoms. "Halogen" or "halo", as used herein, means fluoro, chloro, bromo and iodo.

The Ar group may include:

(1) phenyl or naphthyl, which are optionally substituted by from one- to three-members independently selected as defined above, and (2) heteroaryl, which may include acridine, carbazole, cinnoline, dibenzofuran, dibenzothiophene, quinoxaline, pyrrazole, benzoxazole, indole, imidazole, thiazole, benzothiazole, benzotriazole, furan, benzofuran, benzimidazole, quinoline, isoquinoline, oxazole, pyrazine pyridazine, pyridine, pyrimidine and pyrrole which are optionally substituted.

As will be understood by those skilled in the art, pharmaceutically acceptable salts include, but are not limited to salts with inorganic acids such as hydrochloride, sulfate, phosphate, diphosphate, hydrobromide, and nitrate or salts with an organic acid such as malate, maleate, fumarate, tanrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with amines of the formula $HNR^6R^7$).

In the compounds of Formula I the heteroaryl group may be optionally substituted with X, Y and Z at any available carbon atom or nitrogen atom (if present), but compounds bearing certain of X, Y and Z directly substituted to a nitrogen atom of the heteroaryl ring may be relatively unstable and are not preferred.

The term "heteroaryl" as utilized herein is specifically intended to include the following heteroaromatic groups which may include X, Y and Z substitution as indicated and wherein Q is —N(X)—, —O—, —S—, —SO—, or —SO$_2$—:

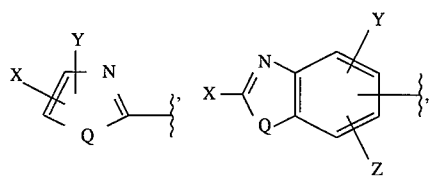

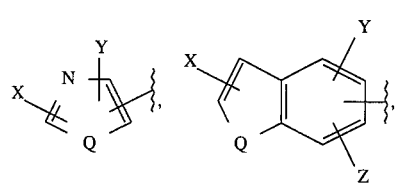

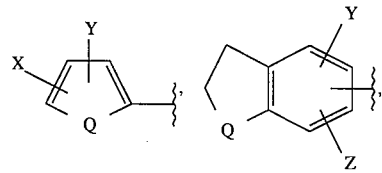

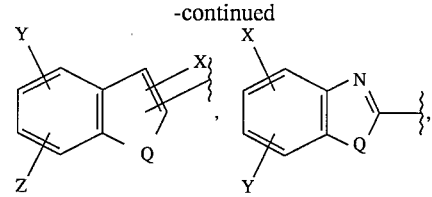

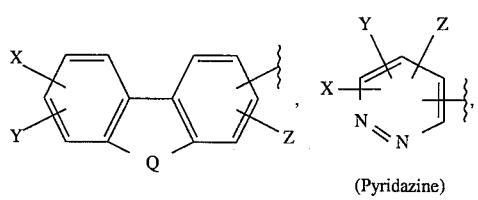

(Pyridazine)

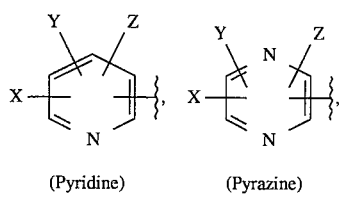

(Pyridine)  (Pyrazine)

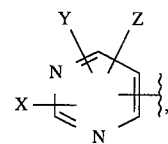

(Pyrimidine)

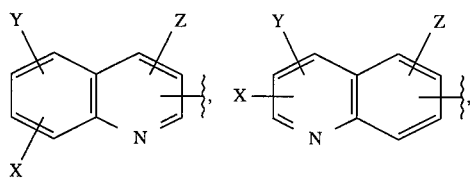

(Quinoline)

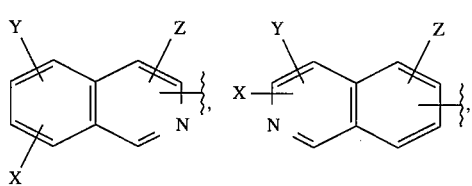

(Isoquinoline)

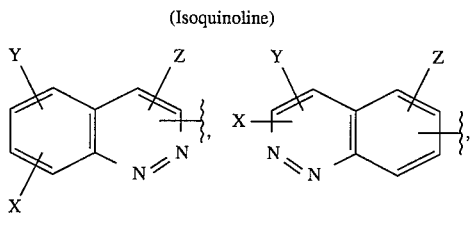

(Cinnoline)

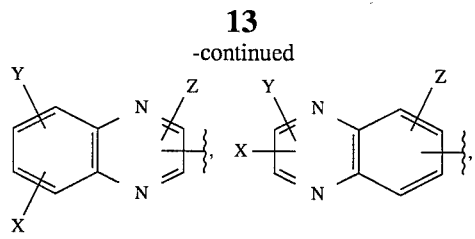

(Quinoxaline)

The aryl or aromatic group may include phenyl or naphthyl which are optionally substituted by from one- to three-members independently selected from the group consisting of: alkyl, alkenyl, halogen, carboxyl, CHO, amino, mono-alkylamino, di-alkylamino, aminoalkyl, mono-alkylaminoalkyl, di-alkylaminoalkyl, alkylthio, alkylsulfinyl, alkysulfonyl, trifluoromethyl, amido, mono-alkylamido, dialkylamido, hydroxy, hydroxyalkyl, $R^{11}$O-alkyl, alkoxy, alkoxyalkyl, formamido, alkyl-$CO_2$—, formamidoalkyl, alkyl-$CO_2$— alkyl-, carboxyl, alkyl-$CO_2$H, alkyl-$O_2$C—, alkyl-$O_2$C-alkyl-, and $OR^{11}$.

In the compound of formula I it is preferred that heteroaryl is selected from the group consisting of:

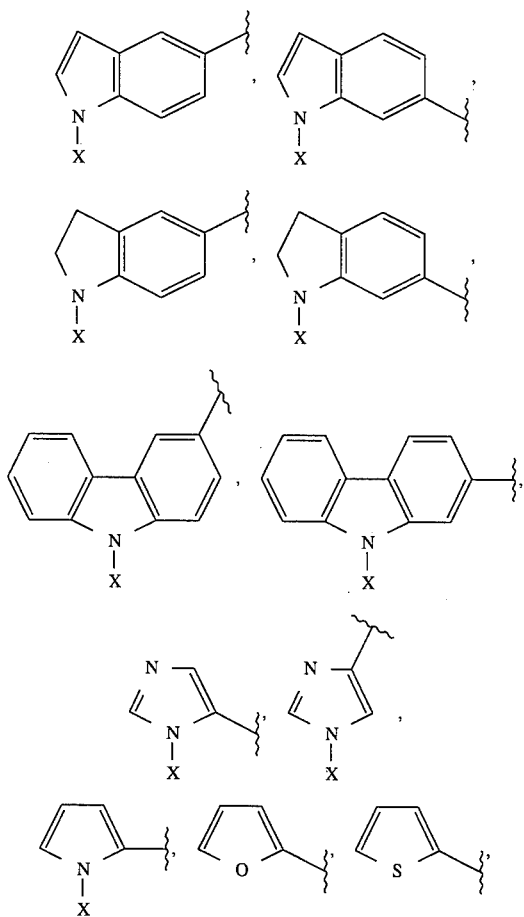

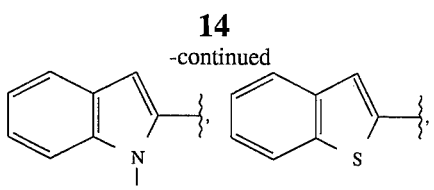

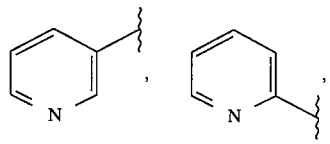

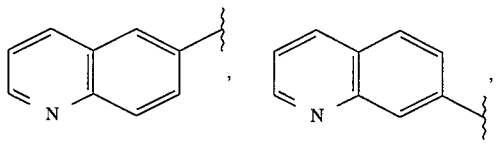

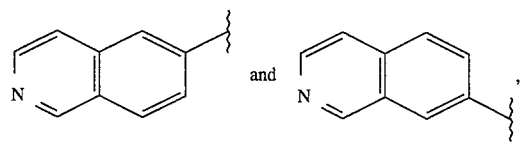

wherein X is as defined above.

In the compound of Formula I it is also preferred that:
A is Ar—B—Ar'—, wherein Ar is heteroaryl, Ar' is phenyl, and B is —O—,
$R^2$ is selected from:
  (1) hydrogen,
  (2) methyl,
  (3) ethyl,
  (4) propyl,
  (5) allyl,
  (6) —$R^{11}$,
  (7) —$C_{2-3}$alkyl—OH; and
  (8) —$C_{2-3}$alkyl—$OR^{11}$;
$R^3$ is selected from:
  (1) hydrogen,
  (2) hydroxy,
  (3) —$OR^{11}$, or $R^3$ and $R^4$ taken together form a double bond;
$R^{10}$ is hydrogen, hydroxy, fluoro, or —$OR^{11}$;
W is O; and
n is 2.

In one embodiment of the present invention, heteroaryl is indole, which may be represented by:

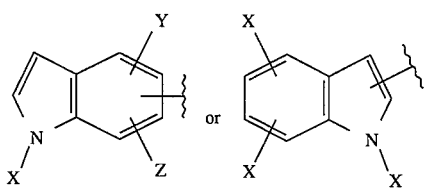

wherein X, Y and Z are as defined above.

Representative compounds of the present invention include the compounds of Formula X and XI:

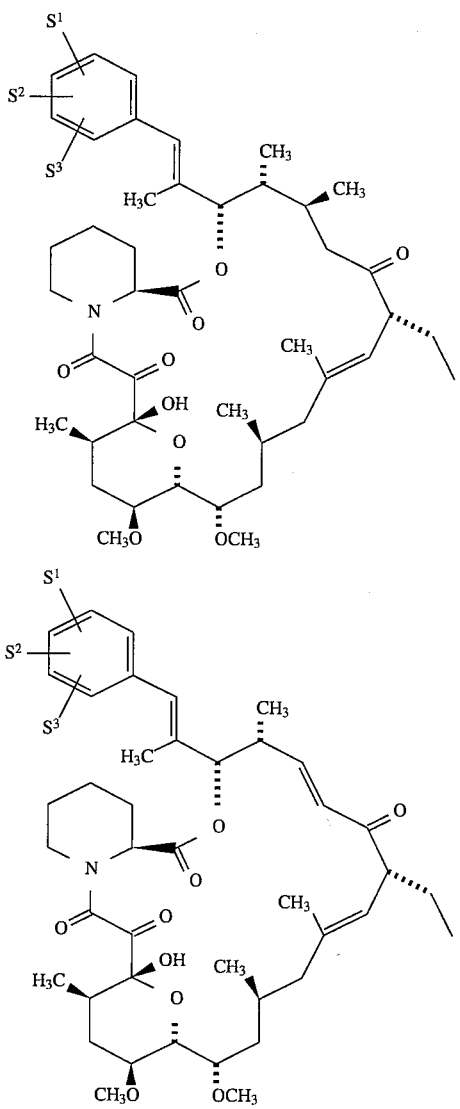

wherein $S^1$, $S^2$, and $S^3$ are selected from the following groups of substituents:

| $S^1$ | $S^2$ | $S^3$ |
|---|---|---|
| 3-H | 4-H | 5-H |
| 3-H | 4-OH | 5-H |
| 3-OH | 4-OH | 5-H |
| 3-OCH$_3$ | 4-OH | 5-H |
| 3-OEt | 4-OH | 5-H |
| 3-Oallyl | 4-OH | 5-H |
| 3-Opropyl | 4-OH | 5-H |
| 3-OH | 4-OCH$_3$ | 5-H |
| 3-OH | 4-OEt | 5-H |
| 3-OH | 4-O-allyl | 5-H |
| 3-OH | 4-O-propyl | 5-H |
| 3-OCH$_3$ | 4-C$_6$H$_5$—O— | 5-H |
| 3-OCH$_3$ | 4-(4-CH$_3$OC$_6$H$_4$O)— | 5-H |
| 3-OCH$_3$ | 4-(4-HOC$_6$H$_4$O)— | 5-H |
| 3-OCH$_3$ | 4-(4-ClC$_6$H$_4$O)— | 5-H |
| 3-OCH$_3$ | 4-[4-(CH$_3$)$_2$NC$_6$H$_4$O]— | 5-H |
| 3-OCH$_3$ | 4-[4-(Et)$_2$NC$_6$H$_4$O]— | 5-H |
| 3-C$_6$H$_4$O— | 4-OCH$_3$ | 5-H |
| 3-(4-CH$_3$OC$_6$H$_4$O)— | 4-OCH$_3$ | 5-H |
| 3-(4-HOC$_6$H$_4$O)— | 4-OCH$_3$ | 5-H |
| 3-(4-ClC$_6$H$_4$O)— | 4-OCH$_3$ | 5-H |
| 3-[4-(CH$_3$)$_2$NC$_6$H$_4$O]— | 4-OCH$_3$ | 5-H |
| 3-[4-(Et)$_2$NC$_6$H$_4$O]— | 4-OCH$_3$ | 5-H |
| 3-OH | 4-OH | 5-OH |
| 3-OCH$_3$ | 4-OH | 5-OH |
| 3-OCH$_3$ | 4-OCH$_3$ | 5-OH |
| 3-OCH$_3$ | 4-OCH$_3$ | 5-OCH$_3$ |
| 3-OEt | 4-OH | 5-OH |
| 3-OEt | 4-OH | 5-OH |
| 3-OEt | 4-OEt | 5-OEt |
| 3-OCH$_3$ | 4-OH | 5-C$_6$H$_5$—O— |
| 3-OCH$_3$ | 4-OH | 5-(4-CH$_3$OC$_6$H$_4$O)— |
| 3-OCH$_3$ | 4-OH | 5-(4-HOC$_6$H$_4$O)— |
| 3-OCH$_3$ | 4-OH | 5-(4-ClC$_6$H$_4$O)— |
| 3-OCH$_3$ | 4-OH | 5-[4-(CH$_3$)$_2$NC$_6$H$_4$O]— |
| 3-OCH$_3$ | 4-OH | 5-[4-(Et)$_2$NC$_6$H$_4$O]— |
| 3-OCH$_3$ | 4-OCH$_3$ | 5-C$_6$H$_5$O— |
| 3-OCH$_3$ | 4-OCH$_3$ | 5-(4-CH$_3$OC$_6$H$_4$O)— |
| 3-OCH$_3$ | 4-OCH$_3$ | 5-(4-HOC$_6$H$_4$O)— |
| 3-OCH$_3$ | 4-OCH$_3$ | 5-(4-ClC$_6$H$_4$O)— |
| 3-OCH$_3$ | 4-OH | 5-[4-(CH$_3$)$_2$NC$_6$H$_4$O]— |
| 3-OCH$_3$ | 4-OCH$_3$ | 5-[4-(Et)$_2$NC$_6$H$_4$O]— |
| 3-OEt | 4-OH | 5-C$_6$H$_5$O— |
| 3-OEt | 4-OH | 5-(4-CH$_3$OC$_6$H$_4$O)— |
| 3-OEt | 4-OH | 5-(4-HOC$_6$H$_4$O)— |
| 3-OEt | 4-OH | 5-(4-ClC$_6$H$_4$O)— |
| 3-OEt | 4-OH | 5-[4-(CH$_3$)$_2$NC$_6$H$_4$O]— |
| 3-OEt | 4-OH | 5-[4-(Et)$_2$NC$_6$H$_4$O]— |
| 3-OEt | 4-OEt | 5-C$_6$H$_5$O— |
| 3-OEt | 4-OH | 5-(4-CH$_3$OC$_6$H$_4$O)— |
| 3-OEt | 4-OH | 5-(4-HOC$_6$H$_4$O)— |
| 3-OEt | 4-OH | 5-(4-ClC$_6$H$_4$O)— |
| 3-OEt | 4-OH | 5-[4-(CH$_3$)$_2$NC$_6$H$_4$O]— |
| 3-OEt | 4-OH | 5-[4-(Et)$_2$NC$_6$H$_4$O]— |
| 3-OCH$_3$ | 4-(3-CH$_3$OC$_6$H$_4$O)— | 5-H |
| 3-OCH$_3$ | 4-(3-HOC$_6$H$_4$O)— | 5-H |
| 3-OCH$_3$ | 4-(3-ClC$_6$H$_4$O)— | 5-H |
| 3-OCH$_3$ | 4-[3-(CH$_3$)$_2$NC$_6$H$_4$O]— | 5-H |
| 3-OCH$_3$ | 4-[3-(Et)$_2$NC$_6$H$_4$O]— | 5-H |
| 3-(3-CH$_3$OC$_6$H$_4$O)— | 4-OCH$_3$ | 5-H |
| 3-(3-HOC$_6$H$_4$O)— | 4-OCH$_3$ | 5-H |
| 3-(3-ClC$_6$H$_4$O)— | 4-OCH$_3$ | 5-H |
| 3-[3-(CH$_3$)$_2$NC$_6$H$_4$O]— | 4-OCH$_3$ | 5-H |
| 3-[3-(Et)$_2$NC$_6$H$_4$O]— | 4-OCH$_3$ | 5-H |
| 3-OCH$_3$ | 4-OH | 5-[3-CH$_3$OC$_6$H$_4$O]— |
| 3-OCH$_3$ | 4-OH | 5-[3-HOC$_6$H$_4$O]— |
| 3-OCH$_3$ | 4-OH | 5-[3-ClC$_6$H$_4$O]— |
| 3-OCH$_3$ | 4-OH | 5-[3-(CH$_3$)$_2$NC$_6$H$_4$O]— |
| 3-OCH$_3$ | 4-OH | 5-[3-(Et)$_2$NC$_6$H$_4$O]— |
| 3-OCH$_3$ | 4-OCH$_3$ | 5-(3-CH$_3$OC$_6$H$_4$O)— |
| 3-OCH$_3$ | 4-OCH$_3$ | 5-(3-HOC$_6$H$_4$O)— |
| 3-OCH$_3$ | 4-OCH$_3$ | 5-(3-ClC$_6$H$_4$O)— |
| 3-OCH$_3$ | 4-OCH$_3$ | 5-[3-(CH$_3$)$_2$NC$_6$H$_4$O]— |
| 3-OCH$_3$ | 4-OCH$_3$ | 5-[3-(Et)$_2$NC$_6$H$_4$O]— |
| 3-OEt | 4-OH | 5-(3-CH$_3$OC$_6$H$_4$O)— |
| 3-OEt | 4-OH | 5-(3-HOC$_6$H$_4$O)— |
| 3-OEt | 4-OH | 5-(3-ClC$_6$H$_4$O)— |
| 3-OEt | 4-OH | 5-[3-(CH$_3$)$_2$NC$_6$H$_4$O]— |
| 3-OEt | 4-OH | 5-[3-(Et)$_2$NC$_6$H$_4$O]— |
| 3-OEt | 4-OEt | 5-(3-CH$_3$OC$_6$H$_4$O)— |
| 3-OEt | 4-OEt | 5-(3-HOC$_6$H$_4$O)— |
| 3-OEt | 4-OEt | 5-(3-ClC$_6$H$_4$O)— |
| 3-OEt | 4-OEt | 5-[3-(CH$_3$)$_2$NC$_6$H$_4$O]— |
| 3-OEt | 4-OEt | 5-[3-(Et)$_2$NC$_6$H$_4$O]— |

| $S^1$ | $S^2$ |
|---|---|
| 3-OH | 4-(1-H-indol-5-yl)—O— |
| 3-OH | 4-(1-CH$_3$-indol-5-yl)—O— |
| 3-OH | 4-(—CH$_3$CH$_2$-indol-5-yl)—O— |
| 3-OH | 4-(HO—CH$_2$CH$_2$-indol-5-yl)—O— |
| 3-OH | 4-(—HO—CH$_2$CH$_2$-indol-5-yl)—O— |
| 3-OH | 4-(—M$^+$O(HO)PO—O—CH$_2$CH$_2$-indol-5-yl)—O— |
| 3-OH | 4-(—M$^+$O(HO)PO—O—CH$_2$CH$_2$-indol-5-yl)—O— |
| 3-OCH$_3$ | 4-(1-H-indol-5-yl)—O— |
| 3-OCH$_3$ | 4-(1-CH$_3$-indol-5-yl)—O— |
| 3-OCH$_3$ | 4-(CH$_3$CH$_2$-indol-5-yl)—O— |

-continued

| $S^1$ | $S^2$ |
|---|---|
| 3-OCH$_3$ | 4(—HO—CH$_2$CH$_2$-indol-5-yl)—O— |
| 3-OCH$_3$ | 4-(—HO—CH$_2$CH$_2$CH$_2$-indol-5-yl)—O— |
| 3-OCH$_3$ | 4-(—M$^+$O(HO)PO—O—CH$_2$CH$_2$-indol-5-yl)—O— |
| 3-OCH$_3$ | 4-(—M$^+$O(HO)PO—O—CH$_2$CH$_2$CH$_2$-indol-5-yl)—O— |
| 3-OCH$_2$CH$_3$ | 4-(1-H-indol-5-yl)—O— |
| 3-OCH$_2$CH$_3$ | 4-(1-CH$_3$-indol-5-yl)—O— |
| 3-OCH$_2$CH$_3$ | 4-(—CH$_3$CH$_2$-indol-5-yl)—O— |
| 3-OCH$_2$CH$_3$ | 4-(—HO—CH$_2$CH$_2$-indol-5-yl)—O— |
| 3-OCH$_2$CH$_3$ | 4-(—HO—CH$_2$CH$_2$CH$_2$-indol-5-yl)—O— |
| 3-OCH$_2$CH$_3$ | 4-(—M$^+$O(HO)PO—O—CH$_2$CH$_2$-indol-5-yl)—O— |
| 3-OCH$_2$CH$_3$ | 4-(—M$^+$O(HO)PO—O—CH$_2$CH$_2$CH$_2$-indol-5-yl)—O— |
| 4-OH | 5-(1-H-indol-5-yl)—O— |
| 4-OH | 5-(1-CH$_3$-indol-5-yl)—O— |
| 4-OH | 5-(—CH$_3$CH$_2$-indol-5-yl)—O— |
| 4-OH | 5-(—HO—CH$_2$CH$_2$-indol-5-yl)—O— |
| 4-OH | 5-(—HO—CH$_2$CH$_2$CH$_2$-indol-5-yl)—O— |
| 4-OH | 5-(—M$^+$O(HO)PO—O—CH$_2$CH$_2$-indol-5-yl)—O— |
| 4-OH | 5-(—M$^+$O(HO)PO—O—CH$_2$CH$_2$CH$_2$-indol-5-yl)—O— |
| 4-OCH$_3$ | 5-(1-H-indol-5-yl)—O— |
| 4-OCH$_3$ | 5-(1-CH$_3$-indol-5-yl)—O— |
| 4-OCH$_3$ | 5-(—CH$_3$CH$_2$-indol-5-yl)—O— |
| 4-OCH$_3$ | 5-(—HO—CH$_2$CH$_2$-indol-5-yl)—O— |
| 4-OCH$_3$ | 5-(—HO—CH$_2$CH$_2$CH$_2$-indol-5-yl)—O— |
| 4-OCH$_3$ | 5-(—M$^+$O(HO)PO—O—CH$_2$CH$_2$-indol-5-yl)—O— |
| 4-OCH$_3$ | 5-(—M$^+$O(HO)PO—O—CH$_2$CH$_2$CH$_2$-indol-5-yl)—O— |
| 4-OCH$_2$CH$_3$ | 5-(1-H-indol-5-yl)—O— |
| 4-OCH$_2$CH$_3$ | 5-(1-CH$_3$-indol-5-yl)—O— |
| 4-OCH$_2$CH$_3$ | 5-(—CH$_3$CH$_2$-indol-5-yl)—O— |
| 4-OCH$_2$CH$_3$ | 5-(—HO—CH$_2$CH$_2$-indol-5-yl)—O— |
| 4-OCH$_2$CH$_3$ | 5-(—HO—CH$_2$CH$_2$CH$_2$-indol-5-yl)—O— |
| 4-OCH$_2$CH$_3$ | 5-(—M$^+$O(HO)PO—O—CH$_2$CH$_2$-indol-5-yl)—O— |
| 4-OCH$_2$CH$_3$ | 5-(-M$^+$O(HO)PO—O—CH$_2$CH$_2$CH$_2$-indol-5-yl)—O— |
| 3-OH | 4-(1-H-indol-6-yl)—O— |
| 3-OH | 4-(1-CH$_3$-indol-6-yl)—O— |
| 3-OH | 4-(—CH$_3$CH$_2$-indol-6-yl)—O— |
| 3-OH | 4-(—HO—CH$_2$CH$_2$-indol-6-yl)—O— |
| 3-OH | 4-(—HO—CH$_2$CH$_2$CH$_2$-indol-6-yl)—O— |
| 3-OH | 4-(—M$^+$O(HO)PO—O—CH$_2$CH$_2$-indol-6-yl)—O— |
| 3-OH | 4-(—M$^+$O(HO)PO—O—CH$_2$CH$_2$CH$_2$-indol-6-yl)—O— |
| 3-OCH$_3$ | 4-(1-H-indol-6-yl)—O— |
| 3-OCH$_3$ | 4-(1-CH$_3$-indol-6-yl)—O— |
| 3-OCH$_3$ | 4-(—CH$_3$CH$_2$-indol-6-yl)—O— |
| 3-OCH$_3$ | 4-(—HO—CH$_2$CH$_2$-indol-6-yl)—O— |
| 3-OCH$_3$ | 4-(—HO—CH$_2$CH$_2$CH$_2$-indol-6-yl)—O— |
| 3-OCH$_3$ | 4-(—M$^+$O(HO)PO—O—CH$_2$CH$_2$-indol-6-yl)—O— |
| 3-OCH$_3$ | 4-(—M$^+$O(HO)PO—O—CH$_2$CH$_2$CH$_2$-indol-6-yl)—O— |
| 3-OCH$_2$CH$_3$ | 4-(1-H-indol-6-yl)—O— |
| 3-OCH$_2$CH$_3$ | 4-(1-CH$_3$-indol-6-yl)—O— |
| 3-OCH$_2$CH$_3$ | 4-(—CH$_3$CH$_2$-indol-6-yl)—O— |
| 3-OCH$_2$CH$_3$ | 4-(—HO—CH$_2$CH$_2$-indol-6-yl)—O— |
| 3-OCH$_2$CH$_3$ | 4-(—HO—CH$_2$CH$_2$CH$_2$-indol-6-yl)—O— |
| 3-OCH$_2$CH$_3$ | 4-(—M$^+$O(HO)PO—O—CH$_2$CH$_2$-indol-6-yl)—O— |
| 3-OCH$_2$CH$_3$ | 4-(—M$^+$O(HO)PO—O—CH$_2$CH$_2$CH$_2$-indol-6-yl)—O— |
| 4-OH | 5-(1-H-indol-6-yl)—O— |
| 4-OH | 5-(1-CH$_3$-indol-6-yl)—O— |
| 4-OH | 5-(—CH$_3$CH$_2$-indol-6-yl)—O— |
| 4-OH | 5-(—HO—CH$_2$CH$_2$-indol-6-yl)—O— |
| 4-OH | 5-(—HO—CH$_2$CH$_2$CH$_2$-indol-6-yl)—O— |
| 4-OH | 5-(—M$^+$O(HO)PO—O—CH$_2$CH$_2$-indol-6-yl)—O— |
| 4-OH | 5-(—M$^+$O(HO)PO—O—CH$_2$CH$_2$CH$_2$-indol-6-yl)—O— |
| 4-OCH$_3$ | 5-(1-H-indol-6-yl)—O— |
| 4-OCH$_3$ | 5-(1-CH$_3$-indol-6-yl)—O— |
| 4-OCH$_3$ | 5-(—CH$_3$CH$_2$-indol-6-yl)—O— |
| 4-OCH$_3$ | 5-(—HO—CH$_2$CH$_2$-indol-6-yl)—O— |
| 4-OCH$_3$ | 5-(—HO—CH$_2$CH$_2$CH$_2$-indol-6-yl)—O— |
| 4-OCH$_3$ | 5-(—M$^+$O(HO)PO—O—CH$_2$CH$_2$-indol-6-yl)—O— |
| 4-OCH$_3$ | 5-(—M$^+$O(HO)PO—O—CH$_2$CH$_2$CH$_2$-indol-6-yl)—O— |
| 4-OCH$_2$CH$_3$ | 5-(1-H-indol-6-yl)—O— |
| 4-OCH$_2$CH$_3$ | 5-(1-CH$_3$-indol-6-yl)—O— |
| 4-OCH$_2$CH$_3$ | 5-(—CH$_3$CH$_2$-indol-6-yl)—O— |
| 4-OCH$_2$CH$_3$ | 5-(—HO—CH$_2$CH$_2$-indol-6-yl)—O— |
| 4-OCH$_2$CH$_3$ | 5-(—HO—CH$_2$CH$_2$CH$_2$-indol-6-yl)—O— |
| 4-OCH$_2$CH$_3$ | 5-(—M$^+$O(HO)PO—O—CH$_2$CH$_2$-indol-yl)—O— |
| 4-OCH$_2$CH$_3$ | 5-(—M$^+$O(HO)PO—O—CH$_2$CH$_2$CH$_2$-indol-6-yl)—O— |
| 4-OH | 3-[C$_6$H$_4$—COCH$_2$—O—] |
| 4-OCH$_3$ | 3-[C$_6$H$_4$—COCH$_2$—O—] |

-continued

| $S^1$ | $S^2$ |
|---|---|
| 4-OEt | 3-[C$_6$H$_4$—COCH$_2$—O—] |
| 4-OH | 3-[3-CH$_3$C$_6$H$_4$—COCH$_2$—O—] |
| 4-OCH$_3$ | 3-[3-CH$_3$C$_6$H$_4$—COCH$_2$—O—] |
| 4-OEt | 3-[3-CH$_3$C$_6$H$_4$—COCH$_2$—O—] |
| 4-OH | 3-[3-CH$_3$OC$_6$H$_4$—COCH$_2$—O—] |
| 4-OCH$_3$ | 3-[3-CH$_3$OC$_6$H$_4$—COCH$_2$—O—] |
| 4-OEt | 3-[3-CH$_3$OC$_6$H$_4$—COCH$_2$—O—] |
| 4-OH | 3-[3-HOC$_6$H$_4$—COCH$_2$—O—] |
| 4-OCH$_3$ | 3-[3-HOC$_6$H$_4$—COCH$_2$—O—] |
| 4-OEt | 3-[3-HOC$_6$H$_4$—COCH$_2$—O—] |
| 4-OH | 3-[C$_6$H$_4$—CH(OH)CH$_2$—O—] |
| 4-OCH$_3$ | 3-[C$_6$H$_4$—CH(OH)CH$_2$—O—] |
| 4-OEt | 3-[C$_6$H$_4$—CH(OH)CH$_2$—O—] |
| 4-OH | 3-[3-CH$_3$C$_6$H$_4$—CH(OH)CH$_2$—O—] |
| 4-OCH$_3$ | 3-[3-CH$_3$C$_6$H$_4$—CH(OH)CH$_2$—O—] |
| 4-OEt | 3-[3-CH$_3$C$_6$H$_4$—CH(OH)CH$_2$—O—] |
| 4-OH | 3-[3-CH$_3$OC$_6$H$_4$—CH(OH)CH$_2$—O—] |
| 4-OCH$_3$ | 3-[3-CH$_3$OC$_6$H$_4$—CH(OH)CH$_2$—O—] |
| 4-OEt | 3-[3-CH$_3$OC$_6$H$_4$—CH(OH)CH$_2$—O—] |
| 4-OH | 3-[3-HOC$_6$H$_4$—CH(OH)CH$_2$—O—] |
| 4-OCH$_3$ | 3-[3-HOC$_6$H$_4$—CH(OH)CH$_2$—O—] |
| 4-OEt | 3-[3-HOC$_6$H$_4$—CH(OH)CH$_2$—O—] |

Representative compounds of the present invention include the compounds of Formula XII, XIII XIV and XV:

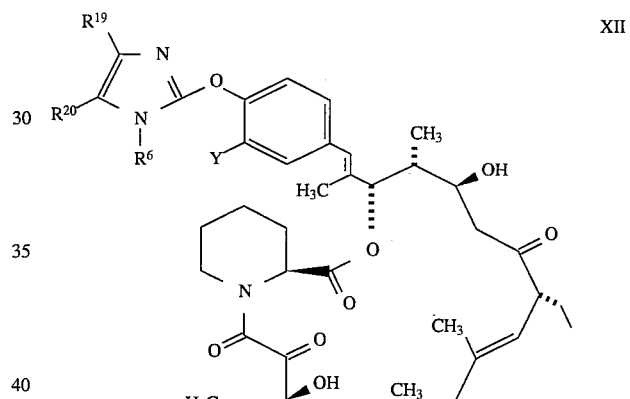

XII

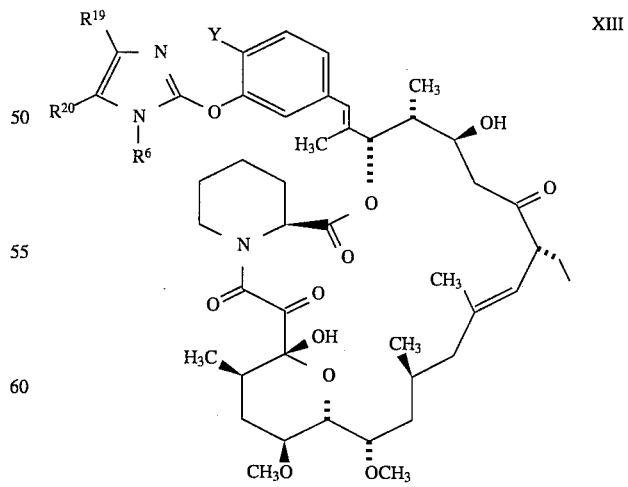

XIII

-continued

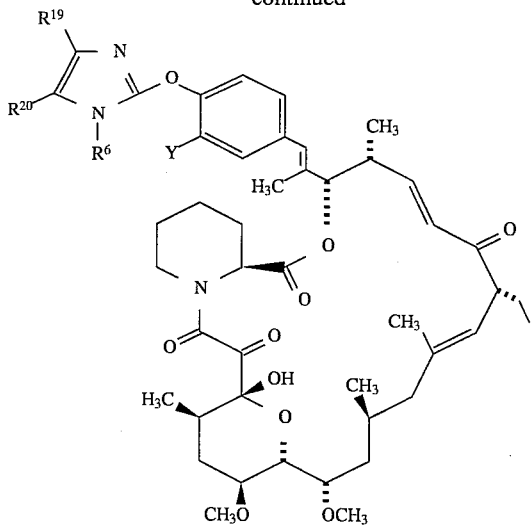

XIV

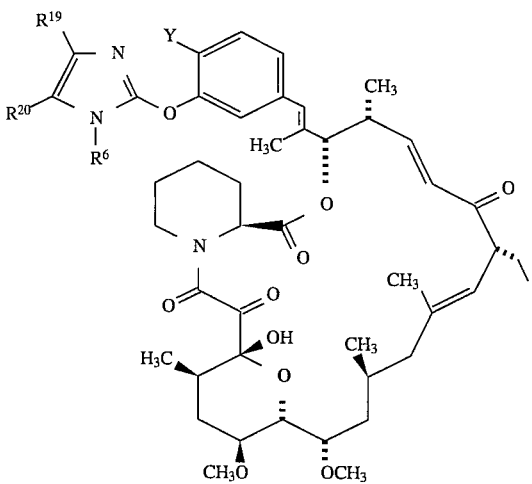

XV wherein $R^6$, $R^{19}$, $R^{20}$, and Y are selected from the following groups of substituents:

| Y | $R^6$ | $R^{19}$ | $R^{20}$ |
|---|---|---|---|
| OH | H | H | H |
| OH | H | H | $C_6H_5$— |
| OH | H | H | 3-Cl$C_6H_4$— |
| OH | H | H | 4-Cl$C_6H_4$— |
| OH | H | H | 3-Br$C_6H_4$— |
| OH | H | H | 4-Br$C_6H_4$— |
| OH | H | H | 3-HO$C_6H_4$— |
| OH | H | H | 4-HO$C_6H_4$— |
| OH | H | H | 3-$CH_3OC_6H_4$— |
| OH | H | H | 4-$CH_3OC_6H_4$— |
| OH | H | H | 3-$CH_3CH_2OC_6H_4$— |
| OH | H | H | 4-$CH_3CH_2OC_6H_4$— |
| OH | H | H | 3-$CH_3CH_2CH_2$— |
| OH | H | H | 4-$CH_3CH_2CH_2$— |
| OH | H | H | 3-$HOCH_2CH_2$— |
| OH | H | H | 4-$HOCH_2CH_2$— |
| $OCH_3$ | H | H | H |
| $OCH_3$ | H | H | $C_6H_5$— |
| $OCH_3$ | H | H | 3-Cl$C_6H_4$— |
| $OCH_3$ | H | H | 4-Cl$C_6H_4$— |
| $OCH_3$ | H | H | 3-Br$C_6H_4$— |
| $OCH_3$ | H | H | 4-Br$C_6H_4$— |
| $OCH_3$ | H | H | 3-HO$C_6H_4$— |
| $OCH_3$ | H | H | 4-HO$C_6H_4$— |
| $OCH_3$ | H | H | 3-$CH_3OC_6H_4$— |
| 3-$OCH_3$ | H | H | 4-$CH_3OC_6H_4$— |
| $OCH_3$ | H | H | 3-$CH_3CH_2OC_6H_4$— |
| $OCH_3$ | H | H | 4-$CH_3CH_2OC_6H_4$— |
| $OCH_3$ | H | H | 3-$CH_3CH_2CH_2$— |
| $OCH_3$ | H | H | 4-$CH_3CH_2CH_2$— |
| $OCH_3$ | H | H | 3-$HOCH_2CH_2$— |
| $OCH_3$ | H | H | 4-$HOCH_2CH_2$— |
| $OCH_2CH_3$ | H | H | H |
| $OCH_2CH_3$ | H | H | $C_6H_5$— |
| $OCH_2CH_3$ | H | H | 3-Cl$C_6H_4$— |
| $OCH_2CH_3$ | H | H | 4-Cl$C_6H_4$— |
| $OCH_2CH_3$ | H | H | 3-Br$C_6H_4$— |
| $OCH_2CH_3$ | H | H | 4-Br$C_6H_4$— |
| $OCH_2CH_3$ | H | H | 3-HO$C_6H_4$— |
| $OCH_2CH_3$ | H | H | 4-HO$C_6H_4$— |
| $OCH_2CH_3$ | H | H | 3-$CH_3OC_6H_4$— |
| $OCH_2CH_3$ | H | H | 4-$CH_3OC_6H_4$— |
| $OCH_2CH_3$ | H | H | 3-$CH_3CH_2OC_6H_4$— |
| $OCH_2CH_3$ | H | H | 4-$CH_3CH_2OC_6H_4$— |
| $OCH_2CH_3$ | H | H | 3-$CH_3CH_2CH_2$— |
| $OCH_2CH_3$ | H | H | 4-$CH_3CH_2CH_2$— |
| $OCH_2CH_3$ | H | H | 4-$HOCH_2CH_2$— |

Representative compounds of the present invention include the compounds of the formula XVI and XVII:

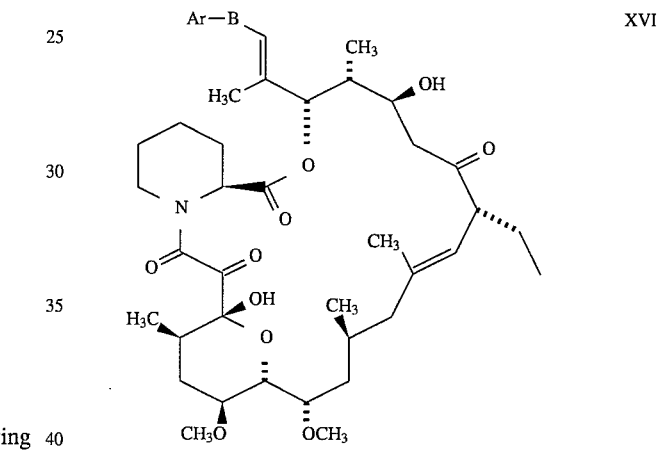

XVI

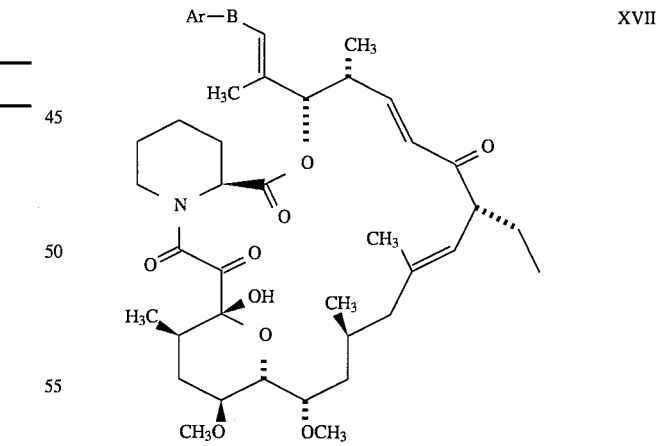

XVII wherein Ar is selected from the group consisting of:
3—$CH_3O$—$C_6H_4$—,
3—HO—$C_6H_4$—,
3—Cl—$C_6H_4$—,
3—$(CH_3)_2N$—$C_6H_4$—,
3—$(Et)_2N$—$C_6H_4$—,
4—$CH_3O$—$C_6H_4$—,
4—HO—$C_6H_4$—,
4—Cl—$C_6H_4$—,
4—$(CH_3)_2N$—$C_6H_4$—, 4—(Et)$_2$N—C$_6$H$_4$—,
1—H-indol-5-yl—,
1—CH$_3$-indol-5-yl—,
1—CH$_3$CH$_2$-indol-5-yl)—,
1—HO—CH$_2$CH$_2$-indol-5-yl)—,
1—HO—CH$_2$CH$_2$CH$_2$-indol-5-yl)—,
1—[—M$^+$ $^-$O(HO)PO—O—CH$_2$CH$_2$]-indol-5-yl—,
1—[—M$^+$ $^-$O(HO)PO—O—CH$_2$CH$_2$CH$_2$]-indol-5-yl—,
1—H-indol-6-yl—,
1—CH$_3$-indol-6-yl—,
1—CH$_3$CH$_2$-indol-6-yl)—,
1—HO—CH$_2$CH$_2$-indol-6-yl)—,
1—HO—CH$_2$CH$_2$CH$_2$-indol-6-yl)—,
1—[—M$^+$ $^-$O(HO)PO—O—CH$_2$CH$_2$]-indol-6-yl—, and
1—[—M$^+$ $^-$O(HO)PO—O—CH$_2$CH$_2$CH$_2$]-indol-6-yl—;
B is selected from the group consisting of:
—NHCO—,
—O$_2$C—,
—CH$_2$—,
—CH$_2$CH$_2$—,
—CH$_2$CH$_2$CH$_2$—,
—CH=CH—,
—(CH$_3$)C=CH—,
—CH=C(CH$_3$)—,
—(CH$_3$)C=(CCH$_3$)—,
—CH$_2$—CH=CH—,
—CH$_2$—(CH$_3$)C=CH—,
—CH$_2$—CH=C(CH$_3$)—,
—CH$_2$—(CH$_3$)C=(CCH$_3$)—,
—CH$_2$—CH$_2$—CH=CH—,
—CH$_2$—CH$_2$—(CH$_3$)C=CH—,
—CH$_2$—CH$_2$—CH=C(CH$_3$)—,
—CH$_2$—CH(CH$_3$)—CH=CH—,
—CH$_2$—CH(CH$_3$)—(CH$_3$)C=CH—,
—CH$_2$—CH(CH$_3$)—CH=C(CH$_3$)—,
—CH(CH$_3$)—CH$_2$—CH=CH—,
—CH(CH$_3$)—CH$_2$—(CH$_3$)C=CH—,
—CH(CH$_3$)—CH$_2$—CH=C(CH$_3$)—,
—CH$_2$—CH(OCH$_3$)—CH=CH—,
—CH$_2$—CH(OCH$_3$)—(CH$_3$)C=CH—,
—CH$_2$—CH(OCH$_3$)—CH=C(CH$_3$)—,
—CH(OCH$_3$)—CH$_2$—CH=CH—,
—CH(OCH$_3$)—CH$_2$—(CH$_3$)C=CH—,
—CH(OCH$_3$)—CH$_2$—CH=C(CH$_3$)—,
—CH$_2$—CH$_2$—CH$_2$—CH=CH—,
—CH$_2$—CH$_2$—CH(CH$_3$)—CH=CH—,
—CH$_2$—CH$_2$—CH(CH$_3$)—(CH$_3$)C=CH—,
—CH$_2$—CH$_2$—CH(CH$_3$)—CH=C(CH$_3$)—,
—CH$_2$—CH(CH$_3$)—CH$_2$—CH=CH—,
—CH$_2$—CH(CH$_3$)—CH$_2$—(CH$_3$)C=CH—,
—CH$_2$—CH(CH$_3$)—CH$_2$—CH=C(CH$_3$)—,
—CH$_2$—CH$_2$—CH(OCH$_3$)—CH=CH—,
—CH$_2$—CH$_2$—CH(OCH$_3$)—(CH$_3$)C=CH—,
—CH$_2$—CH$_2$—CH(OCH$_3$)—CH=C(CH$_3$)—,
—CH$_2$—CH(OCH$_3$)—CH$_2$—CH=CH—,
—CH$_2$—CH(OCH$_3$)—CH$_2$—(CH$_3$)C=CH—,
—CH$_2$—CH(OCH$_3$)—CH$_2$—CH=C(CH$_3$)—,
—CH$_2$—CH(CH$_3$)—CH(OCH$_3$)—CH=CH—,
—CH$_2$—CH(CH$_3$)—CH(OCH$_3$)—(CH$_3$)C=CH—,
—CH$_2$—CH(CH$_3$)—CH(OCH$_3$)—CH=C(CH$_3$)—,
—CH$_2$—CH(OCH$_3$)—CH(CH$_3$)—CH=CH—,
—CH$_2$—CH(OCH$_3$)—CH(CH$_3$)—(CH$_3$)C=CH—, and
—CH$_2$—CH(OCH$_3$)—CH(CH$_3$)—CH=C (CH$_3$)—.

B. Preparation of Compounds Within the Scope of the Present Invention

The starting materials for the prepartion of the compounds of this invention are represented by Formula II:

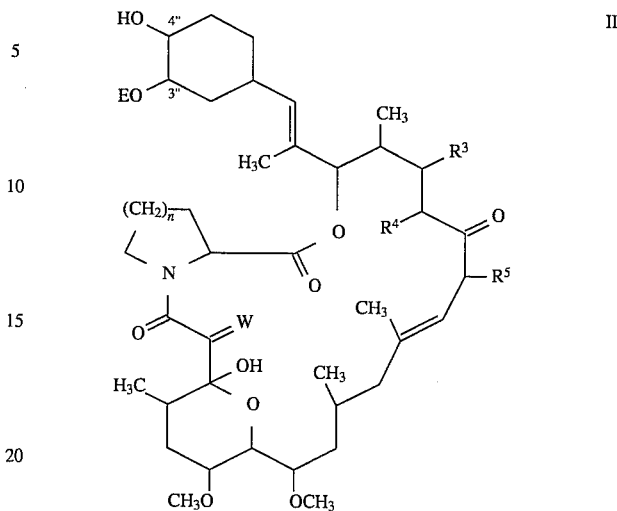

wherein:
E is hydrogen or methyl;
W is O or (H, OH);
R$^3$ is hydrogen, hydroxy, or C$_{1-6}$ alkoxy;
R$^4$ is hydrogen, or R$_3$ and R$_4$ taken together form a double bond;
R$^5$ is methyl, ethyl, propyl or allyl; and
n is 1 or 2.

The production and characterization of compounds of Formula II is well known in the literature (see U.S. Pat. No. 4,894,366, issued Jan. 16, 1990; U.S. Pat. No. 4,929,611, issued May 29, 1990; U.S. Pat. No. 3,244,592, issued Apr. 15, 1966; EPO Publication No. 0,323,042; EPO Publication No. 0,356,399; PBJ Disclosure 63-17884; *J. Am. Chem. Soc.*, 1987, 109, 5031; *J. Antibiotics*, 1987, 40, 1249, *J. Antibiotics*, 1988, 41(11), 1592; and *J. Antibiotics*, 1992, 45(1), 118). Both biological fermentation and synthetic processes may be found. A synthetic route to compounds of Formula II can involve modifications of a route described in *J. Am. Chem. Soc.*, 1989, 111, 1157.

Biological fermentation followed by synthetic modification is presently favored in the an as the method to produce compounds of Formula II. Organisms belonging to the genus Streptomyces such as *Streptomyces tsukubaensis*, No. 9993 and *Streptomyces hygroscopicus*, var. *ascomycetis*, No. 14891 placed in an aqueous nutrient medium will produce desired compounds in isolable amounts. The nutrient medium contains sources of assimilable carbon and nitrogen, preferably under aerobic conditions. Produced in fermentation are four compounds of Formula II, (A) where E is methyl, W is O, R$^3$ is hydroxyl, R$^4$ is hydrogen, R$^5$ is allyl and n is 2; (B) where E is methyl, W is O, R$^3$ is hydroxyl, R$^4$ is hydrogen, R$^5$ is ethyl and n is 2; (C) where E is methyl, W is O, R$^3$ is hydroxyl, R$^4$ is hydrogen, R$^5$ is methyl and n is 2; and (D) where E is methyl W is O, R$^3$ is hydroxyl, R$^4$ is hydrogen, R$^5$ is allyl and n is 1.

A lyophilized sample of the isolated *Streptomyces tsukubaensis*, No. 9993 was deposited with the Fermentation Research Institute, Agency of Industrial Science and Technology (No. 1–3, Higashi 1-chome, Yatabemachi Tsukuba-gun, Ibaraki Prefecture, Japan) under the deposit number of FERM P-7886 (deposit date: Oct. 5, 1984), and then convened to Budapest Treaty route of the same depository on Oct. 19, 1985 under the new deposit number of FERM BP-927.

Using the four compounds produced in fermentation above, the remaining compounds of Formula II may be easily produced. The allyl of $R^5$ may be conveniently reduced to propyl by well known methods, for example as described in U.S. Pat. No. 4,894,366. The hydroxy of $R^3$ may be protected by well known methods, for example as disclosed in EPO Publication No. 0,323,042. Likewise, the hydroxyl at C-4" may also be protected. In addition, the hydroxy of $R^3$ may be reduced to a hydrogen or eliminated to form a double bond with $R^4$ (by methods disclosed in U.S. Pat. No. 4,894,366, EPO publication No. 0,323,042 or EPO Publication No. 0,413,532). The carbonyl of W may be reduced to the alcohol by methods disclosed in EPO Publication No. 0,323,042 or by methods disclosed in EPO Publication No. 0,445,975.

The methyl of E as produced may be replaced with hydrogen or demethylated and subsequently protected as desired, if necessary. This demethylation of compounds wherein E is methyl may be carried out in a fermentation reaction using the compounds of Formula II as a feedstock. For instance, compound A named under Formula II above may be demethylated at E above by using the microorganism Actinomycetales ATCC No. 53771 (described in U.S. Pat. No. 4,981,792) or by using the microorganism *Streptomyces tsukubaensis*, No. 9993 (described in EPO Publication No. 0,353,678). Similarly, compound B named under Formula II above may be demethylated at E above using the microorganism Actinoplanacete sp. ATCC No. 53771 (described in EPO Publication No. 0,349,061). In addition the compound of Formula II wherein E is H, W is O, $R^3$ is hydroxy, $R^4$ is hydrogen, $R^5$ is ethyl and n is 2 may be produced directly by fermentation using the mutant microorganism *Streptomyces hygroscopicus* sup. *ascomyceticus*, No. 53855 (being a blocked mutant of *Streptomyces hygroscopicus* sup. *ascomyceticus*, No. 14891) (as described in EPO Publication No. 0,388,152). Similarly, the compound of Formula II wherein E is hydrogen, W is O, $R^3$ is hydroxy, $R^4$ is hydrogen, $R^5$ is methyl and n is 2 may be produced directly by fermentation using the mutant microorganism *Streptomyces hygroscopicus* sup. *ascomyceticus*, No. 53855 (being a blocked mutant of *Streptomyces hygroscopicus* sup. *ascomyceticus*, No. 14891) (EPO Publication No. 0,388,153). The hydroxy of C-3" may be protected by methods similar to those known for the protection of the hydroxyl groups of $R^3$ and/or C-4", for example as disclosed in U.S. Pat. No. 4,894,366.

Suitable protecting groups for hydroxyl include those groups well known in the art such as: methylthiomethyl, ethylthiomethyl; trisubstituted silyl such as trimethylsilyl, triethylsilyl, tributylsilyl, tri-i-propylsilyl, t-butyldimethylsilyl, tri-t-butylsilyl, methyl-diphenylsilyl, ethyldiphenylsilyl, t-butyldiphenylsilyl, and the like; acyl such as acetyl, pivaloyl benzoyl, 4-methoxybenzoyl, 4-nitrobenzoyl and aliphatic acyl substituted with aromatic group, which are derived from carboxylic acids; and the like.

Compounds A, B, C and D of Formula II, organisms to produce the same, conditions of fermentation, separation techniques, and chemical modification of the products are fully described in U.S. Pat. No. 4,894,366, dated Jan. 16, 1990, U.S. Pat. No. 4,929,611, issued May 29, 1990 and U.S. Pat. No. 5,110,811, issued May 5, 1992.

The novel processes for preparing the novel compounds of the present invention are illustrated as follows, wherein $R^1$, $R^2$, $R^3$, $R^5$, $R^6$, $R^7$, $R^8$, $R^9$, $R^{10}$, $R^{11}$, E, W and n are as defined above unless otherwise indicated. It will be readily apparent to one of ordinary skill in the art reviewing the synthetic route depicted below that other compounds within Formula I can be synthesized by substitution of appropriate reactants and agents in the synthesis shown below.

REACTION SCHEME A

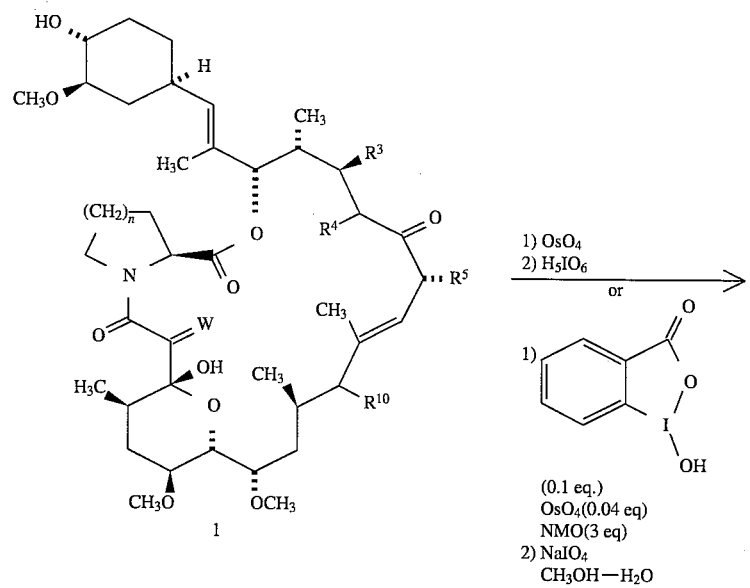

REACTION SCHEME A

-continued

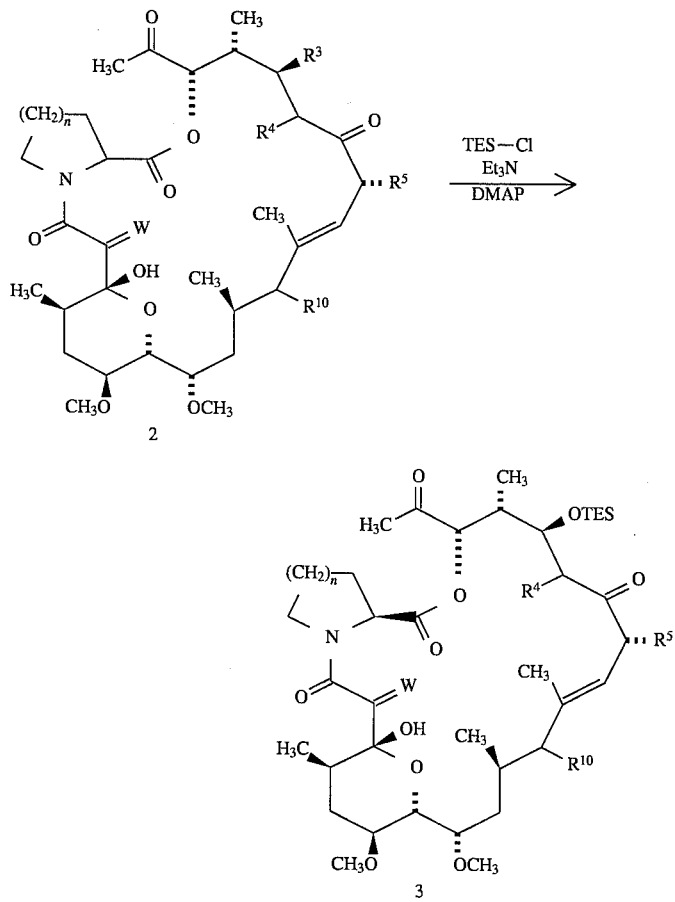

Compounds of this invention may be prepared by a method in which pre-formed components (Ar—A—B—) are combined with the appropriate ketone by various olefination procedures.

The ketone precursors are prepared according to procedures described in Schemes A, B and C.

As shown in Reaction Scheme A, a solution of a 4"-hydroxy- 3"-methoxy macrolide 1 may be regioselectively osmylated with catalytic, stochiometric or excess quantities of $OsO_4$ in methylene chloride. The resulting osmylate maybe cleaved to ketone 2 with periodic acid in reasonable yield. Preferably, the osmylation may be conducted catalytically with 4-methylmorpholine-N-oxide, iodosobenzoic acid, and osmium tetroxide Protection of the $C_{14}$-hydroxyl group ($R^3$=OH) may be accomplished by methods known in the prior an such as by treatment with: 2,6-lutidine and triisopropylsilyl trifluoromethansulfonate in a solution of methylene chloride; 2,6-lutidine; t-butyldimethylsilyl trifluoromethanesulfonate in a solution of methylene chloride; pyridine and acetic anhydride in a solution of methylene chloride; pyridine and benzoyl chloride in a solution of dichloromethane; pyridine and p-nitrobenzoyl chloride in a solution of dichloromethane, imidazole and t-butyldiphenylsilyl chloride in a solution of methylene chloride; and the like. For example, as shown in Reaction Scheme A, ketone 2 may be protected at $C_{14}$ as the tri-ethylsilyl ether (TES) by treatment with tri-ethylsilyl trifluoromethanesulfonate in methylene chloride to give macrolide 3.

REACTION SCHEME B

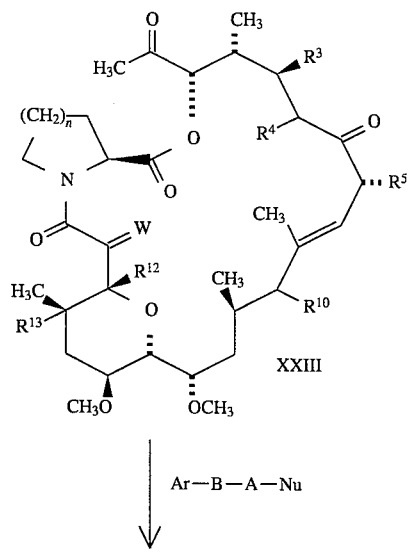

-continued
REACTION SCHEME B

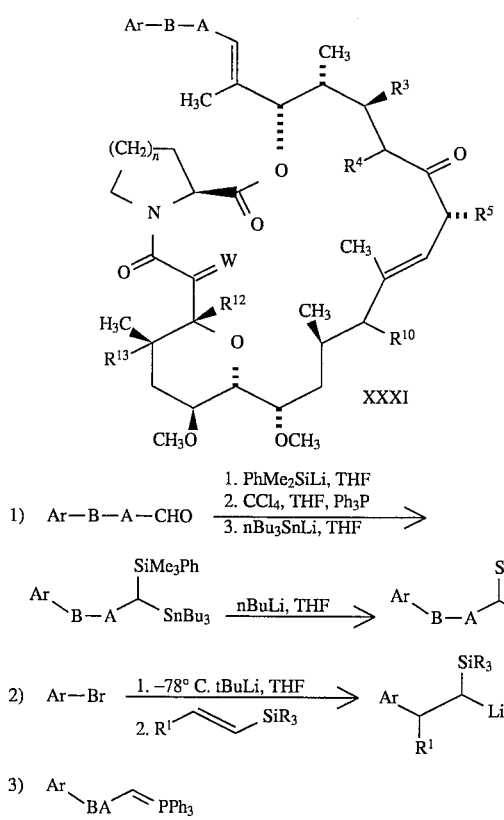

From these olefination reactions, geometric mixtures (E and Z) are produced with the E isomer predominating. These may be separated by standard chromatography methods. The silyl protecting group for the $C_{14}$ hydroxy group (should present) may be removed by stirring the compound in a solution of HF in pyridine.

The reaction sequences described in Reaction Schemes A and B may also be carried out on various structural types of the general structure II.

REACTION SCHEME C

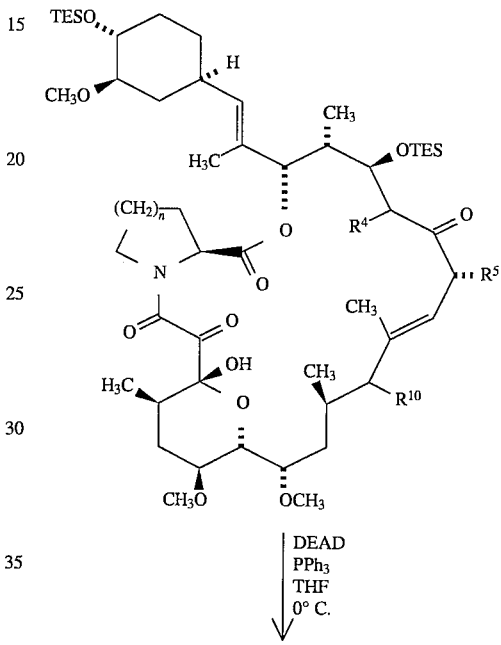

Several olefination methods have been utilized to prepare compounds of the formula XXI from ketones of general structure XXIII. Peterson olefination [addition of an α-silyl lithium carbanion to the carbonyl group at −78° C., followed by spontaneous or HF-mediated elimination of the vicinal hydroxyl group and silyl substituent (5% HF in acetonitrile, rt] is an effective method [Peterson, *J. Org. Chem.* 33, 780 (1968), Magnus, *Aldrichchimica Acta*, 13, 43–51 (1980)]. A general method for preparing the Peterson-type reagents from aldehydes involves the preparation of α-stannyl silane reagents, and their reaction with n-Butyl lithium in an aprotic solvent such as THF, diethyl ether or dimethoxyethane (A. G. M. Barrett, J. M. Hill, *Tetrahedron Lett.* 1991, 32, 3285–3288) [Scheme B, sequence 1]. Another method involves the reaction of aryl carbanions (produced from reaction with t-butyl lithium in a aprotic solvent such as THF at −78° C.) with substituted vinyl silanes [Scheme B, sequence 2].

Stabilized Wittig-type ylid reagents in solvents such as toluene at moderately elevated temperatures (40°–70° C.) are also effective in achieving olefinations [Scheme B, sequence 3].

29
-continued
REACTION SCHEME C
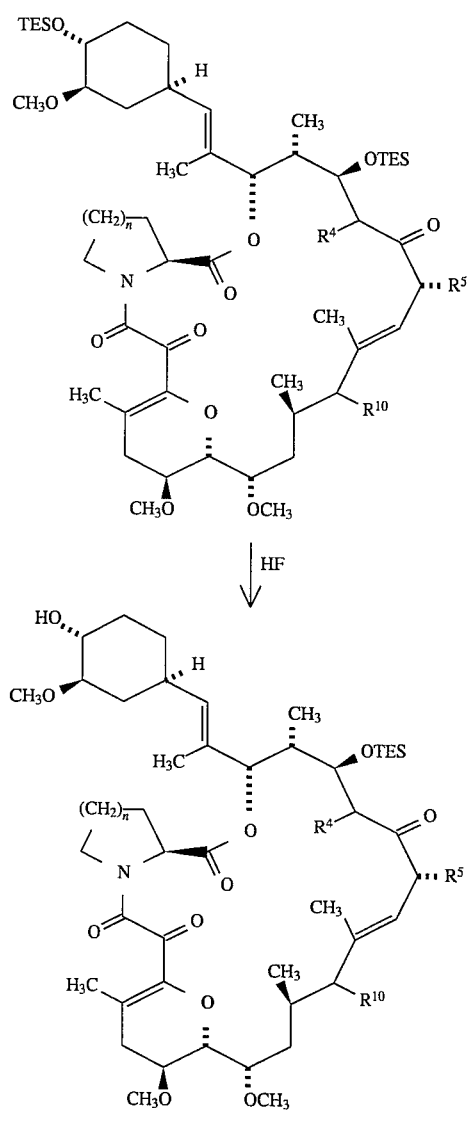
30
-continued
REACTION SCHEME C
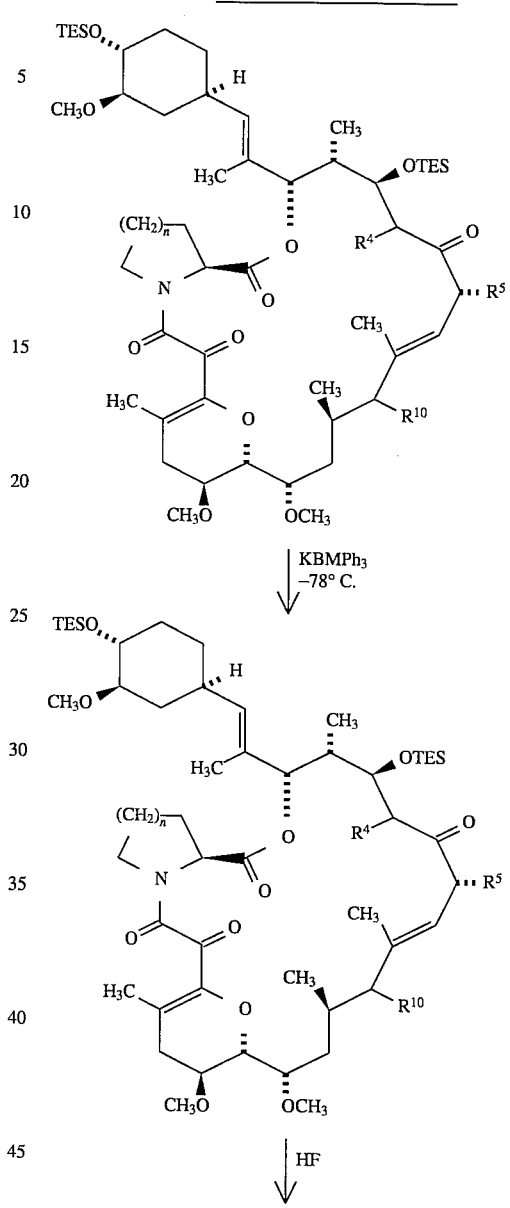

REACTION SCHEME C -continued

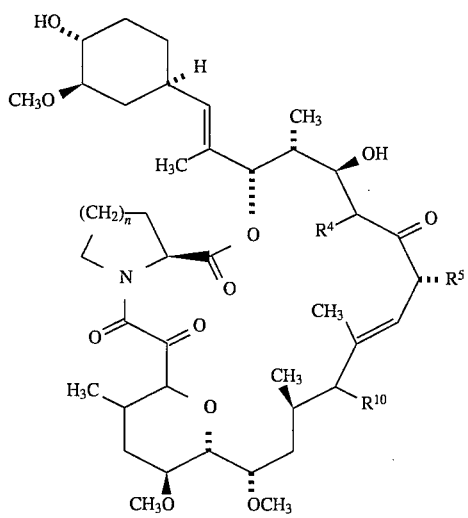

The 4"- and 14- hydroxyl groups of compound 1 may be both protected by methods known in the art such as by treatment with: 2,6-lutidine and triisopropylsilyl trifluoromethanesulfonate in a solution of methylene chloride; 2,6-lutidine; t-butyldimethylsilyl trifluoromethanesulfonate in a solution of methylene chloride; pyridine and acetic anhydride in a solution of methylene chloride; pyridine and benzoyl chloride in a solution of dichloromethane; pyridine and p-nitrobenzoyl chloride in a solution of dichloromethane; imidazole and t-butyldiphenylsilyl chloride in a solution of methylene chloride; and the like. For example, as shown in Reaction Scheme C, the C-4",14-dihydroxy-C-3"-methoxy macrolide 1 may be protected as the bistriethylsilyl ether (TES) 1a by treatment with triethylsilyl trifluoromethanesulfonate in methylene chloride. The C-1 hydroxyl group of 1a may be dehydrated (eliminated) to give $C_{1-2}$ dehydro derivative 4 by Mitsunobu conditions which require diethyldiazo dicarboxylate (DEAD) and triphenyl phosphine in an aprotic solvent such as tetrahydrofuran at reduced temperatures, preferably 0° C. or below [Mitsunobu, et. al. *Tetrahedron*, 26, 5731 (1970)].

The C-1, C-2 olefin of compound 4 may be reduced by a variety of methods. In particular, reaction with a reducing reagent such as potassium triphenylborohydride at reduced temperatures, preferably at −78° C. for an extended time period ranging from 24 to 72 hours to give compound 6. The C-14 and C-4" protecting groups of compounds 4 or 6 can be removed with HF-pyridine complex in tetrahydrofuran to give free alcohols 5 and 2.

REACTION SCHEME D

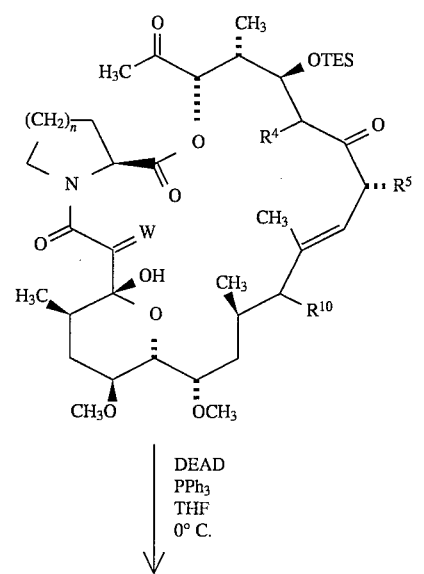

↓ DEAD PPh₃ THF 0° C.

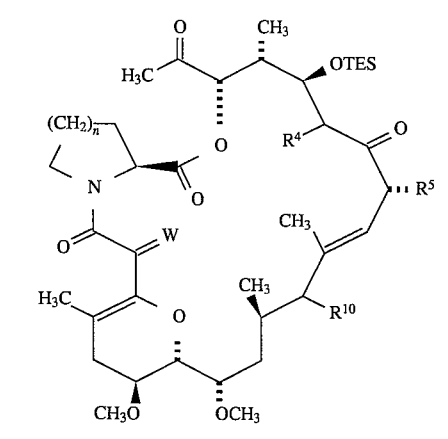

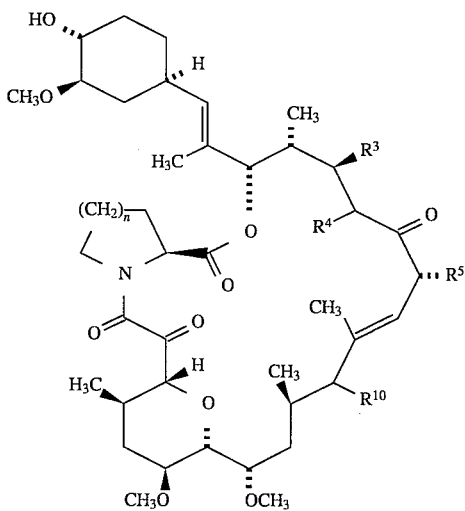

↓

-continued
REACTION SCHEME D

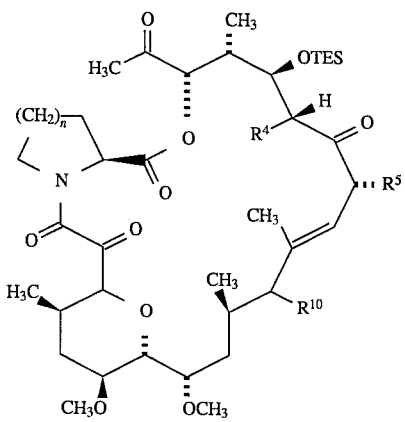

The C-1 hydroxyl group of keto derivative 2 can be dehydrated to compound 8 utilizing Mitsunobu conditions (DEAD, Ph$_3$P, THF) previously described in Reaction Scheme C.

Ketone 9 may be prepared from 7 by procedures described in Reaction Scheme A for the conversion of compound 1 to ketone 2.

Reaction Scheme E

When a derivative of compound I contains a C-14 hydroxyl group (R$^3$=OH, wherein R$^1$, R$^2$, R$^5$, R$^{10}$, W and n are as defined above), the hydroxyl group may be eliminated by treatment with p-toluenesulfonic acid, benzenesulfonic acid or methanesulfonic acid in an inert organic solvent such as benzene, or toluene at from 40° C. to 60° C., for about 0.5 to 6 hours, or a sufficient period of time to eliminate the 14-hydroxy group. Neutralization with an aqueous solution of a weak base such as aqueous saturated sodium bicarbonate gives the 14,15-dehydro macrolides. The 14-hydroxy group may also be eliminated by activation followed by basic elimination, as described in U.S. Pat. No. 4,894,366.

By changing the sequence of synthetic steps, all possible variations of substitution may be achieved.

The object compounds of Formula I obtained according to the reactions as explained above can be isolated and purified in a conventional manner, for example, extraction, precipitation, fractional cyrstallization, recrystallization, chromatography, and the like.

It is to be noted that in the aformentioned reactions and the post-treatment of the reaction mixture therein, the stereoisomer(s) of starting and object compounds due to asymmetric carbon atom(s) or double bond(s) of the object compounds of Formula I may occasionally be transformed into the other stereo isomer(s), and such cases are also included within the scope of the present invention.

In the present invention, compounds with asymmetric centers may occur as racemates, as diastereomeric mixtures and as individual diastereomers, with all isomeric forms of the compounds being included in the present invention. These may be prepared by methods such as those disclosed in publications which describe synthetic routes to fragments of the macrolide FR-900506 and the total synthesis of the macrolide FR-900506 itself (*J. Am. Chem. Soc.* 1989, 111, 1157; *J. Am. Chem. Soc.* 1990, 112, 2998; *J. Org..Chem.* 1990, 55, 2786; *J. Am. Chem. Soc.* 1990, 112, 5583. *Tetrahedron Lett.* 1988, 29, 277; *Tetrahedron Lett.* 1988, 29, 281; *Tetrahedron Lett.* 1988, 29, 3895; *J. Org. Chem.* 1988, 53, 4643; *Tetrahedron Lett.* 1988, 29, 4245; *Tetrahedron Lett.* 1988, 29, 4481; *J. Org. Chem.* 1989, 54, 9; *J. Org. Chem.* 1989, 54, 11; *J. Org. Chem.* 1989, 54, 12; *J. Org. Chem.* 1989, 54, 15; *J. Org. Chem.* 1989, 54, 17; *Tetrahedron Lett.* 1989, 30, 919; *Tetrahedron Lett.* 1989, 30, 1037; *J. Org. Chem.* 1989, 54, 2785; *J. Org. Chem.* 1989, 54, 4267; *Tetrahedron Lett.* 1989, 30, 5235; *Tetrahedron Lett.* 1989, 30, 6611; *Tetrahedron Lett.* 1989, 30, 6963; *Synlett* 1990, 38; *J. Org. Chem.* 1990, 55, 2284; *J. Org. Chem.* 1990, 55, 2771; *J. Org. Chem.* 1990, 55, 2776; *Tetrahedron Lett.* 1990, 31, 1439; *Tetrahedron Lett.* 1990, 31, 1443; *Tetrahedron Lett.* 1990, 31, 3007; *Tetrahedron Lett.* 1990, 31, 3283, 3287).

The compounds of the present invention are capable of forming salts with various inorganic and organic acids and bases and such salts are also within the scope of this invention. Examples of such acid addition salts (which are negative counterions defined herein as M–) include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, oxalate, pamoate, persulfate, picrate, pivalate, propionate, succinate, tartrate, tosylate, and undecanoate. Base salts (which are positive counterions defined herein as M+) include ammonium salts, alkali metal salts such as sodium, lithium and potassium salts, alkaline earth metal salts such as calcium and magnesium salts, salts with organic bases such as dicyclohexylamine salts, N-methyl-D-glucamine, and salts with amino acids such as arginine, lysine and so forth. Also, the basic nitrogen-containing groups may be quaternized with such agents as: lower alkyl halides, such as methyl, ethyl, propyl, and butyl chloride, bromides and iodides; dialkyl sulfates like dimethyl, diethyl, dibutyl; diamyl sulfates; long chain halides such as decyl, lauryl, myristyl and stearyl chlorides, bromides and iodides; aralkyl halides like benzyl bromide and others. The non-toxic physiologically acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

C. Utility of the Compounds Within the Scope of the Invention

The compounds of Formula I may be employed as immunosuppressants or antimicrobial compounds by methods and in dosages known in the prior an for compounds of Formula II. These compounds possess pharmacological activity such as immunosuppressive activity, antimicrobial activity, and the like, and therefore are useful for the treatment and prevention of the resistance to transplantation or transplantation rejection of organs or tissues (such as heart, kidney, liver, lung, bone marrow, cornea, pancreas, intestinum tenue, limb, muscle, nervus, medulla ossium, duodenum, small-bowel, medulla ossium, skin, pancreatic islet-cell, etc. including xeno transplantation), graft-versus-host diseases by medulla ossium transplantation, autoimmune diseases such as rheumatoid arthritis, systemic lupus erythematosis, nephrotic syndrome lupus, Hashimoto's thyroiditis, multiple sclerosis, myasthenia gravis, type I diabetes mellitus, type II adult onset diabetes, uveitis, nephrotic syndrome, steroiddependent and steroid-resistant nephrosis, Palmo-planter pustulosis, allergic encephalomyelitis, glomerulonephritis, etc., and infectious diseases caused by pathogenic microorganisms.

The compounds of Formula I are also useful for treating inflammatory, proliferative and hyperproliferative skin diseases and cutaneous manifestations of immunologically-mediated illnesses such as: psoriasis, psoriatic arthritis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, acne Alopecia areata, eosinophilic fasciitis, and atherosclerosis. More particularly, the compounds of Formula I are useful in hair revitalizing, such as in the treatment of male or female pattern alopecia or alopecia senilis, by providing epilation prevention, hair germination, and/or a promotion of hair generation and hair growth.

The compounds of Formula I are further useful in the treatment of respiratory diseases, for example sarcoidosis, fibroid lung, idiopathic interstitial pneumonia, and reversible obstructive airways disease, including conditions such as asthma, including bronchial asthma, allergic asthma, intrinsic asthma, extrinsic asthma and dust asthma, particularly chronic or inveterate asthma (for example late asthma and airway hyperreponsiveness), bronchitis and the like. The compounds of Formula I may also be useful for treating hepatic injury associated with ischemia.

The compounds of the invention are also indicated in certain eye diseases such as keratoconjunctivitis, vernal conjunctivitis, uveitis associated with Behcet's disease, keratitis, herpetic keratitis, conical cornea, dystorphia epithelialis corneae, corneal leukoma, ocular pemphigus, Mooren's ulcer, Scleritis, Graves' ophthalmopathy, severe intraocular inflammation, and the like.

The compounds of Formula I are also useful for treating multidrug resistance of tumor cells, (i.e. enhancing the activity and/or sensitivity of chemotherapeutic agents), preventing or treating inflammation of mucosa or blood vessels (such as leukotriene $B_4$-mediated diseases, gastric ulcers, vascular damage caused by ischemic diseases and thrombosis, ischemic bowel disease, inflammatory bowel disease (e.g., Crohn's disease and ulcerative colitis) necrotizing enterocolitis), or intestinal lesions associated with thermal burns, cytomegalovirus infection, particularly HCMV infection.

Further, the compounds of Formula I are also useful for treating or preventing renal diseases including interstitial nephritis, Goodpasture's syndrome, hemolytic-uremic syndrome and diabetic nephropathy; nervous diseases selected from multiple myositis, Guillain-Barre syndrome, Meniere's disease and radiculopathy; endocrine diseases including hyperthyroidism and Basedow's disease; hematic diseases including pure red cell aplasia, aplastic anemia, hypoplastic anemia, idiopathic thrombocytopenic purpura, autoimmune hemolytic anemia, agranulocytosis and anerythroplasia; bone diseases including osteoporosis; respiratory diseases including sarcoidosis, fibroid lung and idiopathic interstitial pneumonia; skin diseases including dermatomyositis, leukoderma vulgaris, ichthyosis vulgaris, photoallergic sensitivity and cutaneous T cell lymphoma; circulatory diseases including arteriosclerosis, aortitis syndrome, polyarteritis nodosa and myocardosis; collagen including scleroderma, Wegener's granuloma and Sjogren's syndrome; adiposis; eosinophilic fasciitis; periodontal disease; nephrotic syndrome; hemolytic-uremic syndrome; and muscular dystrophy.

Further, the compounds of the invention are indicated in the treatment of diseases including intestinal inflammations/allergies such as Coeliac disease, proctitis, eosinophilic gastroenteritis, mastocytosis, Crohn's disease and ulcerative colitis; and food related allergic diseases which have symptomatic manifestation remote from the gastrointestinal tract, for example migraine, rhinitis and eczema.

The compounds of the invention also have liver regenerating activity and/or activity in stimulating hypertrophy and hyperplasia of hepatocytes. Therefore, they are useful for the treatment and prevention of hepatic diseases such as immunogenic diseases (e.g. chronic autoimmune liver diseases including autoimmune hepatitis, primary biliary cirrhosis and sclerosing cholangitis), partial liver resection, acute liver necrosis (e.g. necrosis caused by toxins, viral hepatitis, shock or anoxia), B-virus hepatitis, non-A/non-B hepatitis and cirrhosis.

The compounds of the invention are also indicated for use as antimicrobial agents, and thus may be used in the treatment of diseases caused by pathogenic microorganisms and the like.

The compounds of Formula I may also be useful in the prevention or treatment of immunodepression (such as AIDS, HIV infection, cancer, senile dementia, trauma (including wound healing, surgery and shock), chronic bacterial infection and certain central nervous system disorders), overdosages or toxicity of such immunosuppressive compounds, and as an adjunct to the administration of an antigen in vaccination.

The pharmaceutical compositions of this invention can be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non- toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. For example, the compounds of Formula I may be utilized with hydroxypropyl methylcellulose essentially as described in U.S. Pat. No. 4,916,138, issued Apr. 10, 1990, or with a surfactant essentially as described in EPO Publication 0,428, 169. Oral dosage forms may be prepared essentially as described by T. Hondo, et al., *Transplantation Proceedings,* 1987, XIX, Supp. 6, 17–22. Dosage forms for external application may be prepared essentially as described in EPO Publication 0,423,714. The active object compound is included in the pharmaceutical composition in an amount sufficient to produce the desired effect upon the process or condition of diseases.

For the treatment of these conditions and diseases caused by immmunoirregularity a compound of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

For the treatment of reversible obstructive airways disease, it is preferable that the compound of Formula I be administered by inhalation to the lung, especially in the form of a powder.

For modifying the activity and/or toxicity of FK-506-type immunosuppressants, a compound of Formula I may be administered prior to, in conjuction with or subsequent to the administration of an FK-506-type of a compound.

The compounds of Formula I may optionally be employed in co-therapy with anti-proliferative agents. Particularly preferred is co-therapy with an antiproliferative agent selected from the group consisting of azathioprine (AZA), brequinar sodium, deoxyspergualin (DSG), mizaribine, mycophenolic acid morpholino ester (RS-61443), cyclosporin and rapamycin.

The compounds of Formula I may also be employed in conjunction with (or in a pharmaceutical composition additionally comprising):

(1) a 5α-reductase inhibitor, (2) a cyclosporin, (3) a potassium channel opener (such as minoxidil), or (4) a phospholipid.

Such co-therapy is particularly useful in hair revitalizing, such as in the treatment of male pattern alopecia, female pattern alopecia, alopecia senilis or alopecia areata, by providing epilation prevention, hair germination, and/or a promotion of hair generation and hair growth.

Such co-therapy is further useful in treating the hyperandrogenic conditions of androgenic alopecia, acne vulgaris, seborrhea, and female hirsutism.

For co-therapy of these conditions and diseases a compound of Formula I may be administered in combination with prior to, concurrent to, or subsequent to the administration of other agent(s).

For hair revitalizing the compound of Formula I may be administered topically or orally. Cyclosporin may be administered topically or orally. Although the 5α-reductase inhibitor or the potassium channel opener may be administered topically or orally, it is preferable that it be administered topically to the scalp. For unitary formulation, however, the preferred mode of administration is topically. It is especially preferred that the hair revitalizing composition of the present invention is administered by a percutaneous administration or by spraying onto the skin.

Dosage levels of the compounds of the present invention are of the order from about 0.005 mg to about 50 mg per kilogram of body weight per day, preferably from about 0.1 mg to about 10 mg per kilogram of body weight per day, are useful in the treatment of the above-indicated conditions (from about 0.7 mg to about 3.5 mg per patient per day, assuming a 70 kg patient). In addition, the compounds of the present invention may be administered on an intermittent basis; i.e. at daily, semiweekly, weekly, semi-monthly or monthly intervals.

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally comprise from about 0.01 mg to about 500 mg, and preferably about 0.5 mg to about 100 mg of active ingredient. For external administration the compound of Formula I may be formulated within the range of, for example, 0.0001% to 60% by weight, preferably from 0.001 to 10% by weight, and most preferably from about 0.005 to 0.8% by weight.

It will be understood, however, that the specific dose level for any particular patient will depend on a variety of factors including the activity of the specific compound employed, the age, body weight, general health, sex, diet, time of administration, route of administration, rate of excretion, drug combination and the severity of the particular disease undergoing therapy.

The following examples are given for the purpose of illustrating the present invention and shall not be construed as being limitations on the scope or spirit of the instant invention.

Preparation of Starting Intermediates

EXAMPLE 1

7-Ethyl-1,14-dihydroxy-12-(1'-oxo)ethyl-23,25-dimethoxy-13,19,21,27-tetramethyl-11,28-dioxa-4-azatricyclo-[22.3.1.0$^{4,9}$]octacos-18-ene-2,3,10.16-tetraone Method 1:

A solution of 2.01 g (2.52 mmole) of 17-ethyl-1,14-dihydroxy- 12-[2'-(4"-hydroxy-3"-methoxycyclohexyl)-1'-methylvinyl]- 23,25-dimethoxy-13,19,21,27-tetramethyl-11,28-dioxa-4-azatricyclo- [22.3.1.0$^{4,9}$]-octacos-18-ene-2,3, 10,16-tetraone, 0.460 g (3.93 mmole) of 4-methylmorpholine-N-oxide, 0.028 g (0.1 mmole) of iodosobenzoic acid, and 25 mg (0.098 mmole) of osmium tetroxide in 5 mL of dry dichloromethane was stirred in the dark at room temperature for 18 h. An additional 0.470 g (3.95 mmole) of 4-methylmorpholine-N-oxide was added and the solution was stirred at room temperature for 18 h. The solution was partitioned between ether and water and the ether layer was washed with 1.0M NaHSO$_3$ two times, then with brine, 1.0M KHCO$_3$, and brine. The pale yellow solution was dried over MgSO$_4$, and concentrated under vacuum to afford 1.87 g of a 40:60 mixture of diol and starting material. This residue was dissolved in 10 mL of methanol and 1.16 g (5.44 mmole) of NaIO$_4$ in 10 mL of water was added. The solution was stirred at room temperature for 6 hours and the mixture was diluted with water and lyophillized under high vacuum. The residue was triturated with ether and filtered to remove residual salts. The ether was concentrated to afford a yellow solid that was purified by flash chromatography on silica gel (2cm×25 cm column) using 60% ether-hexane to afford 0.631 g (44%) of the title compound as a white solid. Futher elution with 5% isopropanol-dichloromethane afforded 5.80 g (58%) of recovered starting material as a white solid. $^1$H NMR (CDCl$_3$, 2 rotomers) δ0.8–1.05 ppm (m, 8H), 1.59 (s, 3H), 1.78 (s, 3H), 2.10, 2.15 (s, 3H, 12b-CH$_3$), 3.25, 3.35 (s, 3H), 3,39 (s, 3H), $^{13}$C NMR (CDCl$_3$ 2 rotomers) δ97, 98 (C1), 164, 166 (C3), 168, 170 (C10), 192, 197 (C2) 201, 204 (C12a) 210, 212 (C16); Mass Spectrum (FAB) m/e 672 (M+Li).

Method 2:

A solution of 2.0 g (2.53 mmole) of 17-ethyl-1,14-dihydroxy-12-[2'-(4"-hydroxy-3"-methoxycyclohexyl)-1'-methylvinyl]-23,25-dimethoxy-13,19,21,27-tetramethyl-11, 28-dioxa-4-azatricyclo-[22.3.1.0$^{4,9}$]octacos-18-ene-2,3,10, 16-tetraone and 0.700 g (2.76 mmole) of osmium tetroxide in 50 mL of dry dichloromethane was stirred in the dark at room temperature for 40 h. Then hydrogen sulfide was bubbled into the solution for 4 hours, until the filtrate was clear. The mixture was filtered and the solid residue was washed with five 60 mL portions of dichloromethane. The pale yellow filtrate was concentrated under vacuum and the residue was dissolved in 250 mL of an ethereal solution of periodic acid (14 mg $H_5IO_6$/mL solution). The solution was stirred at room temperature for 4 hours (precipitate developed) and the mixture was partitioned between ether and water. The ether layer was washed three times with 1.0M $NaHSO_3$, then saturated $NaHCO_3$, then brine, and dried over $MgSO_4$. The filtrate was concentrated to a yellow solid that was purified by flash chromatography on silica gel (2.5 cm×25 cm column) using 80% ether-hexane to afford 0.270 g (16%) of the title compound as a white solid. Further elution with 5% isopropanol-dichloromethane afforded 0.900 g (45%) of recovered starting material as a white solid. $^1$H NMR $CDCl_3$, 2 rotomers) δ0.8–1.05 ppm (m, 8H), 1.59 (s, 3H), 1.78 (s, 3H), 2.10, 2.15 (s, 3H, 12b-$CH_3$), 3.25, 3.35 (s, 3H), 3.39 (s, 3H). $^{13}$C NMR ($CDCl_3$, 2 rotomers) δ97, 98 (C1), 164, 166 (C3), 168, 170 (C10), 192, 197 (C2) 201, 204 (C12a) 210, 212 (C16); Mass Spectrum (FAB) m/e 672 (M+Li).

Method 3:

A solution of 10.0 g (12.6 mmole) of 17-ethyl-1,14-dihydroxy- 12[2'-(4"-hydroxy'3"-methoxycyclohexyl)-1'-methylvinyl] -23,25-dimethoxy-13,19,21,-27-tetramethyl-11,28-dioxa-4-azatricyclo-[22.3.1.0$^{4,9}$]octacos-18-ene-2,3, 10-16-tetraone and 6.0 g (2.76 mmole) of osmium tetroxide in 30 mL of dry dichloromethane was stirred in the dark at room temperature for 36 h. The solution was saturated with hydrogen sulfide and left stirring at room temperature for 18 h. The solution was retreated with hydrogen sulfide and left stirring for 4 h until the supernatant was clear. The mixture was filtered through Celite and the solid residue was washed with five 60 mL portions of dichloromethane. The pale yellow filtrate was concentrated under vacuum and the residue was dissolved in 250 mL of THF in which 5.4 g (25 mmole) of periodic acid and 20 mL of water had been dissolved. The solution was stirred at room temperature for 4 hours and the mixture was partitioned between ether and water. The ether layer was washed with water, then three times with 1.0M $NaHSO_3$, then saturated $NaHCO_3$, then brine, and dried over $MgSO_4$. The filtrate was concentrated to a yellow solid that was purified by flash chromatography on silica gel (5 cm×25 cm column) using 60% ether-hexane to afford 2.62 g (32%) of the title compound as a white solid. $^1$H NMR ($CDCl_3$, 2 rotomers) δ0.8–1.05 ppm (m, 8H, 1.59 (s, 3H), 1.78 (s, 3H), 2.10, 2.15 (s, 3H, 12b-$CH_3$), 3.25, 3.35 (s, 3H), 3.39 (s, 3H). $^{13}$C NMR ($CDCl_3$, 2 rotomers) δ97, 98 (C1), 164, 166 (C3), 168, 170 (C10), 192, 197 (C2) 201, 204 (C12a) 210, 212 (C16); Mass Spectrum (FAB) m/e 672 (M+Li). Further elution with 5% isopropanol-dichloromethane afforded 5.80 g (58%) of recovered starting material as a white solid.

Method 4, Part A:

A solution of 3.00 g (3.79 mmole) of 17-ethyl-1,14-dihydroxy- 12-[2'-(4"-hydroxy-3"-methoxycyclohexyl)-1'-methylvinyl]- 23,25-dimethoxy-13,19,21,27-tetramethyl-11,28-dioxa-4-azatricyclo-[22.3.1.0$^{4,9}$]octacos-18-ene-2,3,- 10-16-tetraone and 1.0 g (3.94 mmole) osmium tetroxide in 10 mL of dichloromethane was stirred in the dark at room temperature for 18 h. Then 1.6 ml of 1,3-propanedithiol was added and the solution was stirred at room temperature for 3 h. The solution was poured onto a 5 cm×25 cm column of silica gel packed in 10% acetone-hexane and the column was washed with two column volumes of 10% acetone-hexane to remove residual thios. The column was then washed with two column volumes each of 40% acetone-hexane, 50% acetone-hexane, and 80% acetone hexane. Homogeneous fractions were pooled and concentrated to afford 0.703 g (23.4%) of starting material and 1.04 g (33%) of 17-ethyl-1, 14-dihydroxy-12-[2'-hydroxy- 2'-(4"-hydroxy-3"-methoxycyclohexyl)-1'-hydroxy-1'-methylethyl]-23,25-dimethoxy-13,19,21,27-tetramethyl-11,28-dioxa-4-azatricyclo-[22.3.1.0$^{4,9}$]octacos-18-ene-2,3,10,16-tetraone contaminated by a small amount of unreacted starting material.

Method 4, Part B:

A solution of 1.04 g (1.26 mmole) of 17-ethyl-1, 14-dihydroxy- 12-[2'-hydroxy-2'-(4"-hydroxy-3"-methoxycyclohexyl)-1'-hydroxy- 1'-methylethyl]-23,25-dimethoxy-13,19, 21,27-tetramethyl- 11,28-dioxa-4-azatricyclo[22.3.1.0$^{4,9}$] octacos-18-ene-2,3,10,16-tetraone and 1.48 g (6.91 mmole) of periodic acid in 100 mL of ether was stirred at room temperature. The solution turned green, then yellow and a precipitate developed. After 1 h the solution was partitioned between ether and water and the ether layer was washed two portions of 1.0M $NaHSO_3$, then brine, $KHCO_3$, and brine. The solution was dried over $MgSO_4$, concentrated and purified by flash chromatography on silica gel (2.5 cm×20 cm) using 60% ether-hexane and lyophillized from benzene to afford 0.72 g (84%) of the title compound as a white solid. $^1$H NMR ($CDCl_3$, 2 rotomers) δ0.8–1.05 ppm (m, 8H), 1.59 (s, 3H), 1.78 (s, 3H), 2.10, 2.15 (s, 3H, 12b-$CH_3$), 3.25, 3.35 (s, 3H), 3.39 (s, 3H). $^{13}$C NMR ($CDCl_3$, 2 rotomers) δ97, 98 (C1), 164, 166 (C3), 168, 170 (C10), 192, 197 (C2) 201, 204 (C12a) 210, 212 (C16); Mass Spectrum (FAB) m/e 672 (M+Li).

EXAMPLE 2

17-Ethyl-14-triethylsilyloxy-1-dihydroxy-12-(1'-oxo)ethyl-23,25-dimethoxy-13,19,21,27-tetramethyl-11,28-dioxa-4-azatricyclo[22.3.1.0$^{4,9}$]octacos-18-ene-2,3,10,16-tetraone A solution of 2.62 g (3.94 mmole) of 17-ethyl-1,14-dihydroxy- 12-(1'-oxo)ethyl-23,25-dimethoxy-13,19,21,27-tetramethyl- 11,28-dioxa-4-azatricyclo-[22.3.1.0$^{4,9}$]octacos-18-ene-2,3,10,16-tetraone in 10 mL of dry N,N-dimethylformamide was cooled to 0° C. under nitrogen. Then 0.680 g (10 mmole) of imidazole and 2 mL (2.12 g, 8 mmole) of chlorotriethylsilane was added and the solution was stirred at room temperature. After 2 h, the solution was partitioned between ether and water and the ether layer was washed with $KHCO_3$ solution and brine, dried over $MgSO_4$, and concentrated. The residue is was purified by flash chromatography (3 cm×20 cm) using 60% ether-hexane and homogeneous fractions concentrated and lyophillized from benzene to afford 2.43 g (79%) of the title compound as a fine white powder. $^1$H NMR ($CDCl_3$, 2 rotomers) δ0.06=0/ 07 (m, 6H), 0.8–1.05 ppm (m, 18H), 1.59 (s, 3H), 1.78 (s, 3H), 2.10, 2.15 (s, 3H, 12b-$CH_3$), 3.25, 3.35 (s, 3H), 3,39 (s, 3H); Mass Spectrum (FAB) m/e 788 (M+Li).

EXAMPLE 3

17-Ethyl-1,14-dihydroxy-12-[2'-(1-N-methylindol-5-yl)-methyl-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone A solution of 0.101 g (0.5 mmole) of 5-bromo-1-N-methylindole in 2 mL of dry ether was cooled to −78° C.

under nitrogen. Then 0.7 mL (1.1 mmole) of a 1.7M solution of t-butyllithium was added and the solution was stirred at −78° C. for 45 min. The solution was then transferred by canula to a solution of 0.8 mL (0.5 mmole) of vinyltrimethylsilane in 1 mL of dry THF. This solution was stirred at room temperature for 30 min, then was warmed to 0° C. After 15 min, the solution was cooled back to −78° C. and a solution of 77 mg (0.1 mmole) of 17-ethyl-14-triethylsilyloxy-1-hydroxy-12-(1'-oxo)-ethyl- 23,25-dimethoxy-13, 19,21,27-tetramethyl-11,28-dioxa-4-azatricyclo-[22.3.1.0$^{4,9}$]octacos-18-ene-2,3,10,16-tetraone was added and the solution was left stirring at −78° C. After 4 h, the reaction was quenched at −78° C. by addition of 0.2 mL of glacial acetic acid that had been diluted with 1 mL of dry THF. The reaction mixture was partitioned between ether and 1M KHCO$_3$ solution. The ether layer was washed with 1M KHCO$_3$ solution, then brine, dried over MgSO$_4$, and concentrated. The residue was dissolved in 3 mL of 5% HF—CH$_3$CN solution and left to stir at room temperature. After 6 h the reaction mixture was quenched with 2 mL of ethoxytrimethylsilane and stirred at room temperature until gas evolution stopped. The solution was concentrated to dryness and the residue was purified by preparative TLC (Analtech, 500 m) using 60% ether-hexane to afford 0.027 g (35%) of a pale yellow solid along with 0.030 g (45%) of the title compound. The yellow solid was purified by preparatory TLC (Analtech, 250 m) using two elutions of 30% ethyl acetate-hexane to afford 0.018 g (23%) of the title compound as a cream-colored solid. Mass Spectrum (FAB, Li spike) m/e 799 (M+Li).

EXAMPLE 4

General Procedure for Preparation of α-Stannylsilanes

Step 4A: α-(Dimethylphenylsilyl)benzenemethanol

A 38 cm fragment of lithium wire (3.2 mm diameter, 45 mg/cm, 1% sodium content, 0.244 mmole) was cut into 2 mm pieces with a razor blade in a glove bag that had been purged with argon. The fragments were placed in an oven-dried 250 mL round bottom flask and sealed under argon. Then 50 mL of dry THF was added and the mixture was stirred at −10° C. After 10 min. 17.3 mL (100 mmole) of chlorodimethylphenylsilane was added and the mixture was stirred at −10° C. under argon for 36–48 h, until metallation was complete. The cold, dark red solution was transferred by canula to a solution of 6.1 mL (60 mmole) of benzaldehyde in 100 mL of dry THF that had been cooled to −78° C. under argon. The solution was stirred at −78° C. for 45 min and allowed to warm to 0° C. for 30 min. Then it was recooled to −78° C. and quenched by addition of 10 mL of glacial acetic acid in 25 mL of dry THF. The pale yellow solution was partitioned between ether and saturated NH$_4$Cl solution and the ether layer was washed with KHCO$_3$, and brine, dried over MgSO$_4$, and concentrated. The residue was purified by flash chromatography on silica gel (6 cm×30 cm) using 10% ether hexane to afford 11.50 g (79%) of the title compound as a colorless oil. Mass Spectrum (FAB) m/e 243 (M+H).

Step 4B: 1-Chloro-1-(dimethylphenylsily)phenylmethane

A solution of 11.2 g (46.2 mmole) of 1-(dimethylphenylsily)benzenemethanol in 300 mL of dry THF was heated to 70° C. Then 15.72 g (60 mmole) of triphenylphosphine and 25 mL of CCl$_4$ were added and the solution was heated at reflux under nitrogen for 4 h. The solution was allowed to cool to room temperature, diluted with 300 mL of dry ether, stirred at room temperature to complete precipitation, filtered. The filtrate was concentrated to dryness and the residue was filtered through a pad of silica gel using hexane as eluant. The solution was concentrated to afford 10.42 g (87%) of the title compound as a colorless oil. Mass Spectrum (FAB) m/e 263, 261 (M+H).

Step 4C: 1-(Tri-n-butylstannyl)-1-(dimethylphenylsilyl)phenylmethane

A solution 25 mL (50 mmole) of bis(tributyltin) in 100 mL of dry THF was cooled to 0° C. Then 20 mL of a 2.5M solution of butyllithium was added and the solution was stirred at 0° C. for 30 min. This was added to a solution of 10.2 g (39.1 mmole) of 1-chloro-1-(dimethylphenylsilyl)phenylmethane in 50 mL of dry THF and the solution was stirred at room temperature for 2 h. The solution was partitioned between ether and water and the ether layer was washed with water and brine, dried over MgSO$_4$, and concentrated. The residue was purified by flash chromatography (8 cm×30 cm) using hexane to afford 15.71 g (78%) of the title compound as a colorless oil. Mass Spectrum (EI) m/e 515 (M+), 235 (M−Bu$_3$Sn).

EXAMPLE 5

General Procedure for Peterson Olefinations

17-Ethyl-1,14-dihydroxy-12-(2'-(Z)-phenyl-1'-methylvinyl)-23,25-dimethoxy-13,19,21,27-tetramethyl-11,28-dioxa-4-azatricyclo-[22.3.1.0$^{4,9}$]octacos-18-ene-2,3,10,16-tetraone and 17-Ethyl-1,14-dihydroxy-12-(2'-(E)-phenyl-1'-methylvinyl)-23,25-dimethoxy-13,19,21,27-tetramethyl-11,28-dioxa-4-azatricyclo-[22.3.1.0$^{4,9}$]octacos-18-ene-2,3,10,16-tetraone A solution of 0.515 g (1.0 mmole) of 1-(tri-n-butylstannyl)- 1-(dimethylphenylsilyl)phenylmethane in 1 mL of dry THF was cooled to −78° C. under nitrogen. To this was added 0.8 mL of a 2.5M solution of butyllithium in hexane and the solution was stirred at −78° C. for 30 min, then warmed to 0° C. After 15 min. this solution of α-silycarbanion was added dropwise to a solution of 0.077 g (0.1 mmole) of 17-ethyl-14-triethylsilyloxy-1-hydroxy-12-(1'-oxo)ethyl-23,25-dimethoxy- 13,19,21,27-tetramethyl-11, 28-dioxa-4-azatricyclo-[22.3.1.0$^{4,9}$]octacos-18-ene-2,3,10, 16-tetraone that had been cooled to −78° C. under nitrogen. After 4 h, the reaction was quenched at −78° C. by addition of 0.2 mL of glacial acetic acid that had been diluted with 1 mL of dry THF. The reaction mixture was partitioned between ether and 1M KHCO$_3$ solution. The ether layer was washed with 1M KHCO$_3$ solution, then brine, dried over MgSO$_4$, and concentrated. The residue was dissolved in 3 mL of 5% HF—CH$_3$CN solution and left to stir at room temperature. After 6 h the reaction mixture was quenched with 2 mL of ethoxytrimethylsilane and stirred at room temperature until gas evolution stopped. The solution was concentrated to dryness and the residue was purified by preparative TLC (Analtech, 500 m) using 60% ether-hexane to afford 0.034 g (45%) of a pale yellow solid along with 0.032 g (45%) of the ketone starting material. The white solid was purified by preparatory TLC (Analtech, 250 m) using two elutions of 25% ethyl acetate-hexane to afford 0.008 g (11%) of 17-ethyl-1,14-dihydroxy- 12-(2'-(Z)-phenyl-1'-methylvinyl)-23,25-dimethoxy- 13,19,21,27-tetramethyl-11,28-dioxa-4-azatricyclo[22.3.1.0$^{4,9}$]octacos- 18-ene-2,3,10,16-tetraone from the faster band as a white solid. Mass Spectrum (FAB, Li spike) m/e 746 (M+Li).

The slower band from the above TLC was collected to afford 0.012 g (16%) of 17-ethyl-1,14-dihydroxy-12-(2'-(E)-phenyl-1'-methylvinyl)- 23,25-dimethoxy-13,19,21,27-tetramethyl-11,28-dioxa-4-aza-tricyclo[22.3.1.0$^{4,9}$]octacos-18-ene-2,3,10,16-tetraone as a white solid. Mass Spectrum (FAB, Li spike) m/e 746 (M+Li).

EXAMPLE 6

17-Ethyl-1,14-dihydroxy-12-(2'-methoxycarbonyl-1'-methylvinyl)-23,25-dimethoxy-13,19,21,27-tetramethyl-11,28-dioxa-4-azatricyclo-[22.3.1.0$^{4,9}$]octacos-18-ene-2,3,10,16-tetraone Step 6A:
17-Ethyl-14-triethylsilyloxy-1-hydroxy-12-(2'methoxycarbonyl-1'-methylvinyl)-23,25-di-methoxy-13,19, 21,27-tetramethyl-11,28-dioxa-4-azatricyclo[22.3.1.0$^{4,9}$]octacos-18-ene-2,-3,10,16-tetraone A solution of 0.077 g (0.1 mmole) of 17-ethyl-14-triethylsilyloxy- 1-hydroxy-12-(1'-oxo)ethyl-23,25-dimethoxy-13,19,21,27-tetramethyl- 11,28-dioxa-4-azatricyclo [22.3.1.0$^{4,9}$]octacos-18-ene-2,3,10,16-tetraone and 67 mg (0.2 mmole) of methyl triphenylphosphoranylideneacetate in 1 mL of toluene was stirred at 60° C. After 8 h, the solution was diluted with 2 mL of dichloromethane and filtered through a pad of silica gel using dichloromethane as eluate. The filtrate was concentrated and the residue was purified by flash chromatography (2 cm×20 cm column) using 25% ethyl acetate-hexane to afford 0.039 g (46%) of the title compound as a colorless solid. $^1$H NMR (CDCl$_3$) δ 0.6–0.75 (m, 6H) 0.9–1.1 (m, 18H), 1.6, 1.7 (s, 3H), 2.18 2.20 (s, 3H), 3.2–3.4 (m, 6H), 3.9, 3.94 (s, 3H); $^{13}$C NMR δ163, 165 (C2'a) 164, 166 (C3), 169, 171 (C10), 196, 199 (C3) 211, 212 (C16); Mass Spectrum (FAB, Li spike): m/e 842 (M+Li).

Step 6B: 17-Ethyl-1,14-dihydroxy-12-(2'-methoxycarbon-yl-1'-methylvinyl)-23,25-dimethoxy-13,19,21,-27-tetramethyl-11,28-dioxa-4-azatricyclo[22.-3.1.0$^{4,9}$]octacos-18-ene-2,3,10,16-tetraone A solution of 0.030 g (35.6 mmole) of 17-ethyl-14-triethylsilyloxy- 1-hydroxy-12-(2'-methoxycarbonyl-1'-methylvinyl)-23,25-dimethoxy- 13,19,21,27-tetramethyl-11, 28-dioxa-4-azatricyclo[22.3.1.0$^{4,9}$]octacos-18-ene-2,3,10, 16-tetraone in 2 mL of 5% HF—CHC$_3$CN was stirred at room temperature. After 1 h the reaction was quenched with 1 mL of ethoxytrimethylsilane and concentrated to dryness. The residue was purified by flash chromatography (2 cm×20 cm) using 30% ethyl acetate-hexane to afford 0.018 g (69%) of the title compound as a white solid. $^1$H NMR (CDCl$_3$) δ0.9–1.1 (m, 9H), 1.6, 1.7 (s, 3H), 2.18 2.20 (s, 3H), 3.2–3.4 (m, 6H), 3.9, 3.94 (s, 3H); $^{13}$C NMR δ162, 165 (C2'a) 164, 166 (C3), 169, 171 (C10), 196, 201 (C3) 211, 212 (C16); Mass Spectrum (FAB, Li spike): m/e 728 (M+Li).

EXAMPLE 7

17-Ethyl-1,14-dihydroxy-12-(2'-methylcarbonyl-1'-methylvinyl)-23,25-dimethoxy-13,19,21,27-tetramethyl-11,28-dioxa-4-azatricyclo[22.3.1.0$^{4,9}$]octacos-18-ene-2,3,10,16-tetraone Step 7A: 17-Ethyl-14-triethylsilyloxy-1-hydroxy-12-(2'-methylcarbonyl-1'-methylvinyl)-23,25-di-methoxy-13,19,21,27-tetramethyl-11,28-dioxa-4-azatricyclo]22.3.1.0$^{4,9}$] octacos-18-ene-2,3,-10,16-tetraone A solution of 0.078 g (0.1 mmole) of 17-ethyl-14-triethylsilyloxy- 1-hydroxy-12-(1'-oxo)ethyl-23,25-dimethoxy-13,19,21,27-tetramethyl- 11,28-dioxa-4-azatricyclo [22.3.1.0$^{4,9}$]octacos-18-ene-2,3,10,16-tetraone and 67 mg (0.2 mmole) of triphenylphosphoranylidene-2-propanone in 1 mL of toluene was stirred at 60° C. After 24 h, the solution was diluted with 2 mL of dichloromethane and filtered through a pad of silica gel using dichloromethane as eluate. The filtrate was concentrated and the residue was purified by flash chromatography (2 cm×20 cm column) using 25% ethyl acetate-hexane to afford 0.028 g (34%) of the title compound as a colorless solid. $^1$H NMR (CDCl$_3$) δ0.6–0.75 (m, 6H) 0.9–1.1 (m, 18H), 1.6, 1.7 (s, 3H), 2.08–2.11 (s, 3H), 2.18 2.20 (s, 3H), 3.2–3.4 (m, 6H); $^{13}$C NMR δ 164, 166 (C3), 169, 171 (C10), 196, 199 (C3) 201, 201 (C2'a), 211, 212 (C16); Mass Spectrum (FAB, Li spike): m/e 826 (M+Li).

Step 7B: 17-Ethyl-1,14-dihydroxy-12-(2'-methylcarbon-yl-1'-methylvinyl)-23,25-dimethoxy-13,19,21,-27-tetramethyl-11,28-dioxa-4-azatricyclo]22.-3.1.0$^{4,9}$]octacos-18-ene-2,3,10,16-tetraone A solution of 0.022 g (26.8 mmole) of 17-ethyl-14-triethylsilyloxy- 1-hydroxy-12-(2'-methylcar-bonyl-1'-methylvinyl)-23,25-dimethoxy- 13,19,21,27-tetramethyl-11, 28-dioxa-4-azatricyclo[22.3.1.0$^{4,9}$]-octacos-18-ene-2,3,10, 16-tetraone in 2 mL of 5% HF—CHC$_3$CN was stirred at room temperature. After 1 h the reaction was quenched with 1 mL of ethoxytrimethylsilane and concentrated to dryness. The residue was purified by flash chromatography (2 cm×20 cm) using 30% ethyl acetate-hexane to afford 0.015 g (79%) of the title compound as a white solid. $^1$H NMR (CDCl$_3$) δ0.9–1.1 (m, 9H), 1.6, 1.7 (s, 3H), 2.08–2.11 (s, 3H), 2.18 2.20 (s, 3H), 3.2–3.4 (m, 6H); $^{13}$C NMR δ162, 165 (C2'a) 164, 166 (C3), 169, 171 (C10), 196, 201 (C3) 211, 212 (C16). Mass Spectrum (FAB, Li spike): m/e 728 (M+Li).

EXAMPLE 8

17-Ethyl-1,14-dihydroxy-12-(2'-(E)-tert-butoxycarbon-yl-1'-methylvinyl)-23,25-dimethoxy-13,19,21,27-tetramethyl-11,28-dioxa-4-azatricyclo[22.3.1.0$^{4,9}$]octacos-18-ene-2,3,10,16-tetraone and 17-Ethyl-1,14-dihydroxy-12-(2'-(Z)-tert-butoxycarbonyl-1'-methylvinyl)-23,25-dimethoxy-13,19,21,27-tetramethyl-11,28-dioxa-4-azatricyclo-[22.3.1.0$^{4,9}$]octacos-18-ene-2,3,10,16-tetraone Step 8A:
17-Ethyl-14-triethylsilyloxy-1-hydroxy-12-(2'-(E)-tert-butoxycarbonyl-1'-methylvinyl)-23,25-dimethoxy-13,19,21,27-tetramethyl-11,-28-dioxa-4-azatricyclo[22.3.1.0$^{4,9}$]octacos-18-ene-2,3,10,16-tetraone A solution of 0.077 g (0.1 mmole) of 17-ethyl-14-triethylsilyloxy- 1-hydroxy-12-(1'-oxo)ethyl-23,25-dimethoxy-13,19,21,27-tetramethyl- 11,28-dioxa-4-azatricyclo[22.3.1.0$^{4,9}$]octacos-18-ene- 2,3,10,16-tetraone and 72 mg (0.2 mmole) of tert-butyl triphenylphosphoranylideneacetate in 1 mL of toluene was stirred at 60° C. After 8 h, the solution was diluted with 2 mL of dichloromethane and filtered through a pad of silica gel using dichloromethane as eluate. The filtrate was concentrated and the residue was purified by flash chromatography (2 cm×20 cm column) using 25% ethyl acetate-hexane to afford 0.058 g (66%) of the title compound as a colorless solid. $^1$H NMR (CDCl$_3$) δ 0.6–0.75 (m, 6H) 0.9–1.1 (m 18H), 1.2 (s, 9H), 1.6, 1.7 (s, 3H), 2.18 2.20 (s, 3H), 3.2–3.4 (m, 6H); $^{13}$C NMR δ163, 165 (C2'a) 164, 166 (C3), 169, 171 (C10), 196, 199 (C3) 211, 212 (C16); Mass Spectrum (FAB, Li spike): m/e 884 (M+Li).

17-Ethyl-14-triethylsilyloxy-1-hydroxy-12-(2'-(Z)-tert-butoxycarbonyl-1'-methylvinyl)-23,25-dimethoxy-13,19,21,27-tetramethyl-11,28-dioxa-4-azatricyclo[22.-3.1.0$^{4,9}$]octacos-18-ene-2,3,10,16-tetraone The slower product from the above flash chromatography (2 cm×20 cm column) using 25% ethyl acetate-hexane was collected to afford 0.022 g (25%) of the title compound as a colorless solid; $^1$H NMR (CDCl$_3$) δ0.6–0.75 (m, 6H) 0.9–1.1 (m, 18H), 1.2 (s, 9H), 1.6, 1.7 (s, 3H), 2.22 2.26 (s, 3H), 3.2–3.4. (m, 6H); $^{13}$C NMR δ162, 165 (C2'a) 164, 166 (C3), 169, 171 (C10), 196, 199 (C3) 211, 212 (C16); Mass Spectrum (FAB, Li spike): m/e 884 (M+Li).

Step 8B: 17-Ethyl-1,14-dihydroxy-12-(2'-(Z)-tert-butoxycarbonyl-1'-methylvinyl)-23,25-di-methoxy-13,19,21,27-tetramethyl-11,28-dioxa-4-azatricyclo[22.3.1.0$^{4,9}$]octacos-18-ene-2,-3,10,16-tetraone A solution of 0.015 g (17.1 mmole) of 17-ethyl-14-triethylsilyloxy- 1-hydroxy-12-(2'-methoxycarbonyl-1'-methylvinyl)-23,25-dimethoxy- 13,19,21,27-tetramethyl-11,28-dioxa-4-azatricyclo[22.3.1.0$^{4,9}$]-octacos-18-ene-2,3,10,16-tetraone in 2 mL of 5% HF—CH$_3$CN was stirred at room temperature. After 1 h the reaction was quenched with 1 mL of ethoxytrimethylsilane and concentrated to dryness. The residue was purified by flash chromatography (1 cm×15 cm) using 30% ethyl acetate-hexane to afford 0.008 g (64%) of the title compound as a white solid. $^1$H NMR (CDCl$_3$) δ0.9–1.1 (m, 9H), 1.2 (s, 9H), 1.6, 1.7 (s, 3H), 2.18 2.20 (s, 3H), 3.2–3.4 (m, 6H), 3.9, 3.94 (s, 3H); $^{13}$C NMR δ163, 165 (C2'a) 164, 166 (C3), 169, 171 (C10), 196, 201 (C3) 211, 212 (C16); Mass Spectrum (FAB, Li spike): m/e 728 (M+Li).

17-Ethyl-1,14-dihydroxy-12-(2'-(Z)-tert-butoxycarbon-yl-1'-methylvinyl)-23,25-dimethoxy-13,19,21,27-tetramethyl-11,28-dioxa-4-azatricyclo[22.3.1.0$^{4,9}$]octacos-18-ene-2,3,10,16-tetraone A solution of 0.015 g (17.1 mmole) of 17-ethyl-14-triethylsilyloxy-1-hydroxy- 12-(2'-methoxycarbonyl-1'-methylvinyl)-23,25-dimethoxy- 13,19,21,27-tetramethyl-11,28-dioxa-4-azatricyclo[22.3.1.0$^{4,9}$]octacos-18-ene-2,3,10,16-tetraone in 2 mL of 5% HF—CH$_3$CN was stirred at room temperature. After 1 h the reaction was quenched with 1 mL of ethoxytrimethylsilane and concentrated to dryness. The residue was purified by flash chromatography (1 cm×15 cm) using 30% ethyl acetate-hexane to afford 0.008 g (64%) of the title compound as a white solid. $^1$H NMR (CDCl$_3$) δ0.9–1.1 (m, 9H), 1.6, 1.7 (s, 3H), 2.22 2.25 (s, 3H), 3.2–3.4 (m, 6H), 3.9, 3.94 (s, 3H); $^{13}$C NMR δ162, 165 (C2'a) 164, 166 (C3), 169, 171 (C10), 197, 201 (C3) 211, 212 (C16); Mass Spectrum (FAB, Li spike): m/e 770 (M+Li).

EXAMPLE 9

17-Ethyl-1-hydroxy-12-[2'-(4"-hydroxy-3"-methoxycyclohexyl)-1'-methylvinyl)-23,25-dimethoxy-13,19,21,27-tetramethyl-11,28-dioxa-4-azatricyclo[22.3.1.0$^{4,9}$]octacos-18-ene-2,3,10,16-tetraone A solution of 500 mg of 17-ethyl-1,14-dihydroxy-12-[2'-(4"-hydroxy-3-methoxycyclohexyl)-1'-methylvinyl]-23,25-dimethoxy- 13,19,21,27-tetramethyl-11,28-dioxa-4-azatricyclo[22.3.1.0$^{4,9}$]octacos- 18-ene-2,3,10,16-tetraone (1a) in 7 ml of benzene was treated with 10 mg of p-toluenesulfonic acid and the solution was heated at 60° C. for two hours. The reaction mixture was quenched into saturated sodium bicarbonate solution and extracted with ethyl acetate. The combined organic layers were washed with water and saturated sodium chloride solution, dried with anhydrous magnesium sulfate and concentrate. The is residue was chromatographed on silica gel (66% ethyl acetate: 33% hexane: 1% methanol) to give 350 mg of product. This material was dissolved in 10 ml of ethyl acetate and treated with 15 mg of 5% Rh/C. A balloon containing hydrogen was placed over the reaction mixture and the mixture stirred until the reaction was complete. The mixture was filtered through diatomaceous earth, concentrated and the residue subjected to chromatography (75% CH$_2$Cl$_2$: 5% MeOH: 20% Hexane) to give 294 mg of product A.

EXAMPLE 10

17-Ethyl-1-hydroxy-12-[2'-(4",3"-dihydroxyoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1,14-dihydroxy-12-[2'-(4"-hydroxy- 3"-isopropyloxycyclohexyl)-1'-methylvinyl]-23,25- dimethoxy- 13,19,21,27-tetramethyl-11,28-dioxa-4-azatricyclo[22.3.1.0$^{4,9}$]octacos- 18-ene-2,3,10,16-tetraone (210 mg) and a catalytic amount of p-toluenesulfonic acid in 40 ml of benzene was refluxed for 4 hours under a nitrogen atmosphere. The solvent was removed under reduced pressure and the dark residue was purified by chromatography (silica gel, 7% i-propanol/CH$_2$Cl$_2$)to give 17-ethyl-1-hydroxy-12-[2'-(4"-hydroxy- 3"-isopropyloxycyclohexyl)-1'-methylvinyl]-23,25-dimethoxy- 13,19,21,27-tetramethyl-11,28-dioxa-4-azatricyclo-[22.3.1.0$^{4,9}$]octacos- 14,18-diene-2,3,10,16-tetraone (180 mg) as a white solid. This material was dissolved in ethanol (20 ml) and treated with 5% Rh/C (40 mg). Hydrogen was introduced via balloon for 30 min. and the mixture was filtered through celite. Removal of solvent followed by chromatography (silica gel) gave 172 mg of the title compound. Mass Spectrum, 1H and 13C NMR data were consistant with the title structure.

EXAMPLE 11

17-Ethyl-1-hydroxy-12-[2'-(4"-triisopropylsilyloxy-3"-methoxycyclohexyl)-1'-methylvinyl]-14-triisopropyl-silyloxy-23,25-dimethoxy-13,19,21,27-tetramethyl-11,-28-dioxa-4-azatricyclo[22.3.1.0$^{4,9}$]-octacos-18-ene-2,-3,10,16-tetraone To a cooled solution (0° C.) of 17-ethyl-1,14-dihydroxy-12- [2'-(4"-hydroxy-3"-methoxycyclohexyl)-1'-methylvinyl]-23,25-dimethoxy- 13,19,21,27-tetra-methyl-11,28-dioxa-4-azatricyclo[22.3.1.0$^{4,9}$]octacos-18-ene-2,3,10,16,-tetraone (1a) 120 mg) in dry methylene chloride (15 ml) was added 2,6-lutidine (64.3 mg) followed by triisopropylsilyl trifluoromethanesulfonate (184 mg). Reaction temperature was raised to r.t. and stirred overnight under nitrogen atmosphere. The reaction was quenched with 10 ml of water and extracted with ethyl acetate. Organic layer was washed (water, sat'd NaHCO$_3$, sat'd NaCl) and dried (anhydrous MgSO$_4$). Removal of solvent followed by chromatography on silica gel (70% hexane/ethyl acetate) gave 150 mg of product. Mass Spectrum (FAB): 1110 (M+Li).

EXAMPLE 12

Preparation of 17-Ethyl-1-hydroxy-12-[2'-(4"-hydroxy-3"-methoxycyclohexyl)-1'-methylvinyl]-14-triisopropylsilyloxy-23,25-dimethoxy-13,19,21,27-tetramethyl-11,28-dioxa-4-azatricyclo[22.3.1.0$^{4,9}$]octacos-18-ene-2,3,10,16-tetraone (2a)

The title compound from Example 1A (680 mg) was dissolved in methylene chloride (45 ml) and 10% solution of p-toluenesulfonic acid in methanol (45 ml) was added with stirring. The mixture was stirred at room temperature and the progress was followed by tlc analysis. After 4 hr, reaction was quenched with sat'd sodium bicarbonate and extracted with ethyl acetate three times. Normal work-up and removal of solvent followed by purification on silica gel column (80% ethyl acetate/hexane) gave 560 mg of the product as a white solid. Mass Spectrum (FAB): 954 (M+Li).

EXAMPLE 13

Preparation of 17-Ethyl-1-hydroxy-12-[2'-(4"-t-butyl-dimethylsilyloxy-3"-methoxycyclohexyl)-1'-methylvinyl]-14-t-butyldimethylsilyloxy-23,25-dimethoxy-13,19,21,27-tetramethyl-11,28-dioxa-4-azatricyclo[22.3.1.0$^{4,9}$] octacos-18-ene-2,3,10,16-tetraone To a cooled solution (0° C.) of 17-ethyl-1,14-dihydroxy-12-[2'-(4"-hydroxy-3"-methoxycyclohexyl)-1'-methylvinyl] -23,25-dimethoxy- 13,19,21,27-tetramethyl-11,28-dioxa-4-azatricyclo[22.3.1.0$^{4,9}$]-octacos-18-ene-2,3,10,16-tetraone (1a) (395 mg) in dry methylene chloride (15 ml) was added 2,6-lutidine (160 mg) followed by t-butyldimethylsilyl triflouromethanesulfonate (250 mg). Reaction temperature was raised to r.t. and stirred under nitrogen atmosphere. After 6 hr, the reaction was quenched with 10 ml of water and extracted with ethyl acetate. Organic layer was washed (water, saturated NaHCO$_3$, saturated NaCl) and dried (anhydrous MgSO$_4$). Removal of solvent under reduced pressure gave 500 mg of crude product. Mass Spectrum (FAB): 1023 (M+Li).

EXAMPLE 14

17-Ethyl-1-hydroxy-12-[2'-(4"-hydroxy-3"-methoxycyclohexyl)-1'-methylvinyl]-14-t-butyldimethylsilyloxy-23,25-dimethoxy-13,19,21,27-tetramethyl-11,28-dioxa-4-azatricyclo-[22.3.1.0$^{4,9}$]octacos-18-ene-2,3,10,16-tetraone (2b)

The product from the previous example (500 mg) was dissolved in acetonitrile (20 ml) and 100 ml of hydrogen fluroide (48%) was added. Reaction was stirred for 20 minutes at room temperature, quenched with saturated sodium bicarbonate, then extracted with ethyl acetate. Removal of solvent in vacuo followed by chromatography on silica gel (80% ethyl acetate/hexane) gave 300 mg of product (Mass, $^1$H and $^{13}$C NMR data consistent with the title compound).

EXAMPLE 15

17-Ethyl-1-hydroxy-12-[2'-(4"-(tert-butyldimethylsiloxy)-3"-hydroxycyclohexyl)-1'-methylvinyl]-23,25-dimethoxy-13,19,21,27-tetramethyl-11,28-dioxa-4-azatricyclo[22.3.1.04,9 ]octacos-18-ene-2,3,10,16-tetraone To a solution of 17-ethyl-1-hydroxy-12-[2'(3",4"-dihydroxycyclohexyl)- 1'-methylvinyl]-23,25-dimethoxy-13,19, 21,27-tetramethyl- 11,28-dioxa-4-azatricyclo[22.3.1.0$^{4,9}$] octacos-18-ene-2,3,10,16-tetraone (3.01 g) in dry methylene chloride (70 ml) was added an excess of imidazole (809 mg) followed by tert-butyldimethylsilyl chloride (716 mg). After 3 days of stirring at room temperature, the mixture was diluted with ethyl acetate which in turn was washed with 1N HCl, saturated sodium bicarbonate and brine, dried over magnesium sulfate and purified by flash chromatography (ethylacetate:hexane (1:3)) to give the title compound (941 mg) ($^1$H NMR consistent with the desired structure).

EXAMPLE 16

17-Ethyl-1,14,20-trihydroxy-12-[2'-(4"-hydroxy-3"-methoxycyclohexyl)-1'-methylvinyl]-23,25-dimethoxy-13,19,21,27-tetramethyl-1,28-dioxa-4-azatricyclo[22.3.1.0$^{4,9}$]octacos-18-ene-2,3,10,16tetraone To stirred solution of 17-ethyl-1-hydroxy-12-[2'-(4"-t-butyldimethylsilyloxy- 3"-methoxycyclohexyl)-1'-methylvinyl]-14-t-butyldimethylsilyloxy- 23,25-dimethyoxy-13,19,21,27-tetramethyl- 11,28-dioxa-4-azatricyclo[22.3.1.0$^{4,9}$]octacos-18-ene-2,3,10,16-tetraone in 95% ethanol was added pyridine followed by SeO$_2$. The flask was then refluxed at 70° C. After 20 hours, the reaction mixture was cooled to rt and filtered through diatomaceous earth. The filtrate was poured into a saturated sodium bicarbonate solution which was extracted with ethyl acetate, washed with brine, dried over magnesium sulfate, filtered and concentrated in vacuo. The product was chromatographed [silica, ethyl acetate:hexanes (1:2)+1% methanol] to give 17-Ethyl-1,20-dihydroxy- 12-[2'-(4"-t-butyldimethylsilyloxy-3"-methoxycyclohexyl)- 1'-methylvinyl]-14-t-butyldimethylsilyloxy-23,25-dimethoxy- 3,19,21,27-tetramethyl-11,28-dioxa-4-azatricyclo-[22.3.1.0$^{4,9}$]octacos-18-ene-2,3,10,16-tetraone. This material was dissolved in tetrahydrofuran in a polypropylene vial. To this was added HF-pyridine solution in THF. After stirring at room temperature for 28 hr, the mixture was added to saturated sodium bicarbonate solution. The reaction mixture was extracted with ethyl acetate, the organic extracts were filtered through a thin pad of magnesium sulfate, and the filtrate was evaporated in vacuo. The crude product was purified by chromatography (silica, ethyl acetate:hexanes 2:1+1% methanol) to give the title compound.

EXAMPLE 17

17-Ethyl-1,14,20-trihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Alternate Route To a solution of 17-ethyl-1,14-dihydroxy-12-[2'-(4"-hydroxy- 3"-methoxycyclohexyl)-1'-methylvinyl]-23,25-dimethoxy- 13,19,21,27-tetramethyl-11,28-dioxa-4-azatricyclo[22.3.1.0.$^{4,9}$]octacos- 18-ene-2,3,10,16-tetraone (51.5 g, 0.065 mol) in glacial acetic acid (500 ml) at room temperature, was added a solution of selenium dioxide (9.27 gm, 0.083 mol) in H$_2$O (90 ml). The reaction mixture was stirred at room temperature for 41 hours whereupon, it was poured into a stirred mixture of H$_2$O (3 L) and celite. After stirring for 15 minutes, the mixture was filtered through a pad of celite and extracted with diethyl ether (1×2 L, 2×1 L). The organic fractions were washed with saturated sodium bicarbonate and brine, dried over magnesium sulfate, filtered and evaporated in vacuo. The product was purified by chromatography (silica, acetone:hexanes 2:5) to give the title compound. Mass Spectrum and NMR were consistant with the desired structure.

EXAMPLE 18

17-Ethyl-20-fluoro-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$] octacos-18-ene-2,3,10,16-tetraone To a stirred solution of 17-Ethyl-1,20-di-hydroxy-12-[2'-(4"-t-butyldimethylsilyloxy-3"-methoxycyclohexyl)-1'-methylvinyl]-14-t-butyldimethylsilyloxy- 23,25-dimethoxy-13,19,21,27-tetramethyl- 11,28-dioxa-4-azatricyclo [22.3.1.0$^{4,9}$]octacos-18-ene-2,3,10,16-tetraone in methylene chloride cooled to −78° C. was added diethylaminosulfur trifluoride. After 3 min., saturated sodium bicarbonate solution was added followed by ethyl acetate and the reaction mixture was allowed to warm to room temperature. The reaction mixture was extracted with ethyl acetate, the organic extracts were dried over magnesium sulfate, filtered and evaporated in vacuo. The product was purified by chromatography (silica, ethyl acetate:hexanes 1:2+1% methanol. To a solution of this material (10 mg) in THF (0.6 ml) in a polypropylene vial was added 40 μL of HF-pyridine solution in THF. After stirring for 28 hours at rt, the mixture was added to a saturated solution of sodium bicarbonate. This mixture was extracted with ethyl acetate and the organic extracts were dried over magnesium sulfate, filtered and evaporated in vacuo. The product was purified by chromatography (silica, ethyl acetate:hexanes 2:1+1% methanol) to give the title compound. Mass Spectrum (FAB): 832 (M+Na)

EXAMPLE 19

T-Cell Proliferation Assay
1. Sample Preparation
 The compounds to be assayed were dissolved in absolute ethanol at 1 mg/ml.
2. Assay
 Spleens from C57B1/6 mice were taken under sterile conditions and gently dissociated in ice-cold RPMI 1640 culture medium (GIBC), Grand Island, N.Y.) supplemented with 10% heat-inactivated fetal calf serum (GIBO)). Cells were pelleted by centrifugation at 1500 rpm for 8 minutes. Contaminating red cells were removed by treating the pellet with ammonium chloride lysing buffer (GIBO)) for 2 minutes at 4° C. Cold medium was added and cells were again centrifuged at 1500 rpm for 8 minutes. T lymphocytes were then isolated by separation of the cell suspension on nylon wool columns as follows: Nylon wool columns were prepared by packing approximately 4 grams of washed and dried nylon wool into 20 ml plastic syringes. The columns were sterilized by autoclaving at 25° F. for 30 minutes. Nylon wool columns were wetted with warm (37° C.) culture medium and rinsed with the same medium. Washed spleen cells resuspended in warm medium were slowly applied to the nylon wool. The columns were then incubated in an upright position at 37° C. for 1 hour. Non-adherent T lymphocytes were eluted from the columns with warm culture medium and the cell suspensions were spun as above.

Purified T lymphocytes were resuspended at 2.5×10$^5$ cells/ml in complete culture medium composed of RPMI 1640 medium with 10% heat- inactivated fetal calf serum, 100 mM glutamine, 1 mM sodium pyruvate, 2×10$^{-5}$M 2-mercaptoethanol and 50 μg/ml gentamycin. Ionomycin was added at 250 ng/ml and PMA at 10 ng/ml. The cell suspension was immediately distributed into 96 well flat-bottom microculture plates (Costar) at 200 μl/well. The various dilutions of the compound to be tested were then added in triplicate wells at 20 μl/well. The compound 17-allyl-1,14-dihydroxy-12-[2'-(4"-hydroxy-3"-methoxycyclohexyl)- 1'-methylvinyl]-23,25-dimethoxy-13,19,21,27-tetramethyl- 11,28-dioxa-4-aza-tricyclo[22.3.1.0^{4,9}]octacos-18-ene- 2,3,10,16-tetraone was used as a standard. The culture plates were then incubated at 37° C. in a humidified atmosphere of 5% $CO_2$-95% air for 44 hours. The proliferation of T lymphocytes was assessed by measurement of tritiated thymidine incorporation. After 44 hours of culturing, the cells were pulse-labelled with 2 μCi/well of tritiated thymidine (NEN, Cambridge, Mass.). After another 4 hours of incubation, cultures were harvested on glass fiber filters using a multiple sample harvester. Radioactivity of filter discs corresponding to individual wells was measured by standard liquid scintillation counting methods (Beta-counter). Mean counts per minute of replicate wells were calculated and the results expressed as concentration of compound required to inhibit tritiated thymidine uptake of T-cells by 50%. A selection of compounds were tested according to the previous procedure and had activity in inhibiting the proliferation of T-cells in the aforementioned assay. The results of this assay are representative of the intrinsic immunosuppressive activity of the compounds of the present invention.

For determining antagonist activity, the foregoing procedure is modified in that dilutions of compounds are cultured with 17-ally-1,14-dihydroxy-12-[2'-(4"-hydroxy-3"-methoxycyclohexyl)-1'-methylvinyl]- 23,25-dimethoxy-13,19, 21,27-tetramethyl-11,28-dioxa-4-azatricyclo[22.3.1.0^{4,9}]octacos-18-ene-2,3,10,16-tetraone (as a standard) at a concentration of 1.2 nM, a concentration which inhibits T cell proliferation by 100%, the concentration of compound required to reverse the inhibition obtained by the standard alone by 50% is measured, and the $ED_{50}$ value is determined.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of formula I:

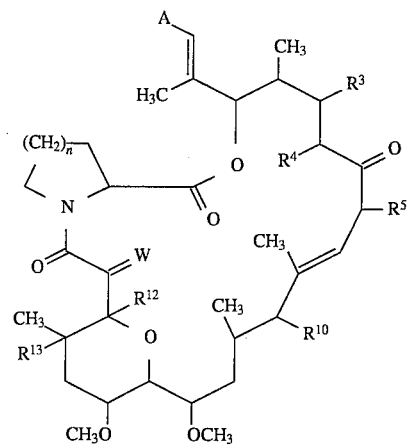

wherein:

A is selected from the group consisting of:
(1) Ar—B—, and
(2) Ar—B—Ar'—;

Ar is selected from the group consisting of:
(1) phenyl,
(2) substituted phenyl in which the substituents are X, Y, and Z,
(3) heteroaryl, and
(4) substituted heteroaryl in which the substituents are X, Y, and Z;

Ar' is selected from the group consisting of:
(1) phenyl,
(2) substituted phenyl in which the substituents are X, Y, and Z,
(3) heteroaryl, and
(4) substituted heteroaryl in which the substituents are X, Y, and Z;

B is a bond or is selected from the group consisting of:
(1) —O—,
(2) —$NR^6$—, wherein $R^6$ is as defined below,
(3) —S(O)p—, wherein p is 0, 1 or 2,
(4) $C_{1-10}$alkyl,
(5) substituted $C_{1-10}$alkyl in which the alkyl portion may be substituted with one or more of the substituent(s) selected from:
(a) hydroxy,
(b) oxo,
(c) $C_{1-6}$alkoxy,
(d) phenyl-$C_{1-3}$alkoxy,
(e) substituted phenyl-$C_{1-3}$alkoxy, in which the substituents on phenyl are X, Y and Z,
(f) unsubstituted or substituted phenyloxy, in which the substituents on phenyl are X, Y and Z,
(g) —OCO—$C_{1-6}$alkyl,
(h) —$NR^6R^7$, wherein $R^6$ and $R^7$ are independently selected from:
(i) hydrogen,
(ii) $C_{1-10}$alkyl unsubstituted or substituted with
(a') phenyl, which is unsubstituted or substituted with X, Y and Z,
(b') —OH,
(c') $C_{1-6}$alkoxy,
(d') —$CO_2H$,
(e') —$CO_2C_{1-6}$alkyl,
(f') —$C_{3-7}$cycloalkyl,
(g') —$OR^{11}$ (iii) $C_{3-10}$alkenyl unsubstituted or substituted with one or more of the substituent(s) selected from:
(a') aryl, which is unsubstituted or substituted with X, Y and Z,
(b') heteroaryl, which is unsubstituted or substituted with X, Y and Z,
(c') —OH,
(d') $C_{1-6}$alkoxy,
(e') —$CO_2H$,
(f') —$CO_2$—$C_{1-6}$alkyl,
(g') —$C_{3-7}$cycloalkyl, and
(h') —$OR^{11}$,
(iv) or where $R^6$ and $R^7$ and the N to which they are attached may form an unsubstituted or substituted 3–7-membered heterocyclic ring which may include one or two additional heteroatoms independently selected from the group consisting of O, $S(O)_p$, $NR^{14}$, wherein $R^{14}$ is hydrogen or $C_{1-6}$alkyl unsubstituted or substituted by phenyl, and p is 0, 1 or 2, selected from: morpholine, thiomorpholine, piperidine, and piperizine,
(i) —$NR^6CO$—$C_{1-6}$alkyl-$R^7$ wherein $R^6$ and $R^7$ are as defined above,
(j) —$NR^6CO_2$—$C_{1-6}$alkyl-$R^7$,
(k) —$NR^6CONR^6R^7$,
(l) —$OCONR^6R^7$,
(m) —$COOR^6$,
(n) —CHO,
(o) phenyl,
(p) substituted phenyl in which the substituents are X, Y and Z
(q) —$OR^{11}$ and
(r) —$S(O)_p$—$C_{1-6}$alkyl, (6) $C_{1-10}$alkyl wherein one or more of the alkyl carbons is replaced by a group selected from: —$NR^6$—, —O—, —$S(O)_p$—, —$CO_2$—, —$O_2C$—, —$CONR^6$—, —$NR^6CO$—, —$NR^6CONR^7$—, (7) substituted $C_{1-10}$alkyl wherein one or more of the alkyl carbons is replaced by a group selected from: —$NR^6$—, —O—, —$S(O)_p$—, —$CO_2$—, —$O_2C$—, —$CONR^6$—, —$N^6CO$— and —$NR^6CONR^7$—, and the alkyl group may be substituted by one or more of the substituent(s) selected from:
(a) hydroxy,
(b) oxo,
(c) $C_{1-6}$alkoxy,
(d) phenyl-$C_{1-3}$alkoxy,
(e) substituted phenyl-$C_{1-3}$alkoxy, in which the substituents on phenyl are X, Y and Z,
(f) unsubstituted or substituted phenyloxy, in which the substituents on phenyl are X, Y and Z,
(g) —OCO—$C_{1-6}$alkyl,
(h) —$NR^6R^7$, wherein $R^6$ and $R^7$ are as defined above,
(i) —$NR^6CO$—$C_{1-6}$alkyl-$R^7$,
(j) —$NR^6CO_2C_{1-6}$alkyl-$R^6$,
(k) —$NR^6CONR^6R^7$,
(l) —$OCONR^6R^7$,
(m) —$COOR^6$,
(n) —CHO,
(o) phenyl,
(p) substituted phenyl in which the substituents are X, Y and Z
(q) —$OR^{11}$ and
(r) —$S(O)_p$—$C_{1-6}$alkyl, (8) $C_{3-10}$alkenyl wherein alkenyl contains one to four double bonds, (9) $C_{3-10}$alkenyl wherein alkenyl contains one to four double bonds and wherein one or more of the alkyl carbons is replaced by a group selected from: —$NR^6$—, —O—, —$S(O)_p$—, —$CO_2$—, —$O_2C$—, —$CONR^6$—, —$NR^6CO$—, —$NR^6CONR^7$—,

(10) substituted $C_{3-10}$alkenyl wherein alkenyl contains one to four double bonds and wherein one or more of the alkyl carbons may be replaced by a group selected from: —$NR^6$—, —O—, —$S(O)_p$—, —$CO_2$—, —$O_2C$—, —$CONR^6$—, —$NR^6CO$—, —$NR^6CONR^7$, and the alkyl group may be substituted by one or more of the substituent(s) selected from:
(a) hydroxy,
(b) oxo,
(c) $C_{1-6}$alkoxy,
(d) phenyl$C_{1-3}$alkoxy,
(e) substituted phenyl$C_{1-3}$alkoxy, in which the substituents on phenyl are X, Y and Z,
(f) unsubstituted or substituted phenyloxy, in which the substituents on phenyl are X, Y and Z,
(g) —OCO—$C_{1-6}$alkyl,
(h) —$NR^6R^7$, wherein $R^6$ and $R^7$ are as defined above,
(i) —$NR^6CO$—$C_{1-6}$alkyl,
(j) —$NR^6CO_2$—$C_{1-6}$alkyl,
(k) —$NR^6CONR^6R^7$,
(l) —$OCONR^6R^7$,
(m) —$COOR^6$,
(n) —CHO,
(o) phenyl,
(p) substituted phenyl in which the substituents are X, Y and Z
(q) —$OR^{11}$ and
(r) —$S(O)_n$—$C_{1-6}$alkyl,

(11) $C_{3-10}$alkynyl wherein alkynyl contains one or two triple bonds,

(12) $C_{3-10}$alkynyl wherein alkynyl contains one or two triple bonds and wherein one or more of the alkyl carbons is replaced by a group selected from: —$NR^6$—, —O—, —$S(O)_p$—, —$CO_2$—, —$O_2C$—, —$CONR^6$—, —$NR^6CO$—, —$NR^6CONR^7$—,

(13) substituted $C_{3-10}$alkynyl wherein alkynyl contains one or two triple bonds and wherein one or more of the alkyl carbons is replaced by a group selected from: —$NR^6$—, —O—, —$S(O)_p$—, —$CO_2$—, —$O_2C$—, —$CONR^6$—, —$NR^6CO$—, —$NR^6CONR^7$, and Z, and the alkyl group may be substituted by one or more of the substituent(s) selected from:
(a) hydroxy,
(b) oxo,
(c) $C_{1-6}$alkoxy,
(d) phenyl-$C_{1-3}$alkoxy,
(e) substituted phenyl$C_{1-3}$alkoxy, in which the substituents on phenyl are X, Y and Z,
(f) unsubstituted or substituted phenyloxy, in which the substituents on phenyl are X, Y and Z,
(g) —$OCOR^6$,
(h) —$NR^6R^7$, wherein $R^6$ and $R^7$ are as defined above,
(i) —$NR^6CO$—$C_{1-6}$alkyl,
(j) —$NR^6CO_2$—$C_{1-6}$alkyl,
(k) —$NR^6CONR^6R^7$,
(l) —$OCONR^6R^7$,
(m) —$COOR^6$,
(n) —CHO,
(o) phenyl,
(p) substituted phenyl in which the substituents are X, Y and Z
(q) —$OR^{11}$, and
(r) —$S(O)_p$—$C_{1-6}$alkyl;

$R^3$ is hydrogen, hydroxy, —$OR^{11}$, or $C_{1-6}$alkoxy;

$R^4$ is hydrogen, or $R^3$ and $R^4$ taken together form a double bond;

$R^5$ is methyl, ethyl, propyl, or allyl;

$R^{10}$ is hydrogen, hydroxy, $-OR^{11}$, or fluoro;

$R^{11}$ is selected from:
- (a) $-PO(OH)O-M+$, wherein M+ is a positively charged inorganic or organic counterion selected from the group consisting of: ammonium, sodium, lithium, potassium, calcium, magnesium, dicyclohexylamino, N-methyl-D-glucamino, argininyl, and lysinyl,
- (b) $-SO_3-M+$,
- (c) $-CO(CH_2)_qCO_2-M+$, wherein q is 1–3, and
- (d) $-CO-C_{1-6}$alkyl$-NR^6R^7$, wherein $R^6$ and $R^7$ are as defined above and the alkyl is unsubstituted or substituted with one or more substituents selected from:
  - (i) hydroxy,
  - (ii) $C_{1-6}$alkoxy,
  - (iii) $-NR^{17}R^{18}$, wherein $R^{17}$ and $R^{18}$ are independently selected from:
    - (a') hydrogen, and
    - (b') $C_{1-6}$alkyl,
  - (iv) $-COOR^6$, wherein $R^6$ is as defined above,
  - (v) phenyl,
  - (vi) substituted phenyl in which the substituents are X, Y and Z,
  - (vii) heteroaryl,
  - (viii) $-SH$, and
  - (ix) $-S-C_{1-6}$alkyl;

$R^{12}$ is hydroxy, or hydrogen;

$R^{13}$ is hydrogen, or $R^{12}$ and $R^{13}$ taken together form a double bond;

W is O or (H, OH);

X, Y and Z independently are selected from the group consisting of:
- (a) hydrogen,
- (b) $C_{1-10}$alkyl, unsubstituted or substituted with one or more substituents selected from:
  - (i) aryl,
  - (ii) substituted aryl in which the substituents are X', Y' and Z',
  - (iii) heteroaryl,
  - (iv) substituted heteroaryl in which the substituents are X', Y', and Z',
  - (v) unsubstituted or substituted aryloxy, in which the substituents on aryl are X', Y' and Z',
  - (vi) $-OR^6$,
  - (vii) $-OR^{11}$,
  - (viii) $-OCOR^6$,
  - (ix) $-OCO_2R^6$,
  - (x) $-NR^6R^7$,
  - (xi) $-CHO$,
  - (xii) $-NR^6COC_{1-6}$alkyl$-R^7$,
  - (xiii) $-NR^6CO_2C_{1-6}$alkyl$-R^7$,
  - (xiv) $-NR^6CONR^6R^7$,
  - (xv) $-OCONR^6R^7$,
  - (xvi) $-CONR^6R^7$,
- (c) $C_{1-10}$alkyl wherein one or more of the alkyl carbons is replaced by a group selected from $-NR^6-$, $-O-$, $-S(O)_p-$, $-CO_2-$, $-O_2C-$, $-CONR^6-$, $-NR^6CO-$, $-NR^6CONR^7-$, $-CO-$, $-CH(OH)-$, alkenyl or alkynyl and the alkyl may be unsubstituted or substituted with one or more substituents selected from:
  - (i) aryl,
  - (ii) substituted aryl in which the substituents are X', Y' and Z',
  - (iii) heteroaryl,
  - (iv) substituted heteroaryl in which the substituents are X', Y', and Z',
  - (v) unsubstituted or substituted aryloxy, in which the substituents on aryl are X', Y', and Z',
  - (vi) $-OR^6$,
  - (vii) $-OR^{11}$,
  - (viii) $-OCOR^6$,
  - (ix) $-OCO_2R^6$,
  - (x) $-NR^6R^7$,
  - (xi) $-CHO$,
  - (xii) $-NR^6COC_{1-6}$alkyl$-R^7$,
  - (xiii) $-NR^6CO_2C_{1-6}$alkyl$-R^7$,
  - (xiv) $-NR^6CONR^6R^7$,
  - (xv) $-OCONR^6R^7$,
  - (xvi) $-CONR^6R^7$,
- (d) halogen,
- (e) $-NR^6R^7$,
- (f) $-CN$,
- (g) $-CHO$,
- (h) $-CF_3$,
- (i) $-SR^8$, wherein $R^8$ is hydrogen, $C_{1-6}$alkyl, trifluoromethyl, or phenyl,
- (j) $-SOR^8$,
- (k) $-SO_2R^8$,
- (l) $-CONR^6R^7$,
- (m) $R^9O(CH_2)_m-$ wherein $R^9$ is hydrogen, $C_{1-6}$alkyl, hydroxy-$C_{2-3}$alkyl, $-CF_3$, phenyl, $R^{11}$ or naphthyl and m is 0, 1, 2, or 3,
- (n) $-CH(OR^{15})(OR^{16})$, wherein $R^{15}$ and $R^{16}$ are $C_{1-3}$alkyl or taken together form an ethyl or propyl bridge,
- (o)

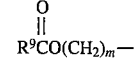

wherein $R^9$ and m are as defined above,
- (p)

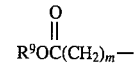

wherein $R^9$ and m are as defined above, and
- (q) $-R^{11}$,
- (r) aryl,
- (s) substituted aryl in which the substituents are X', Y' and Z', or any two of X, Y and Z may be joined to form a saturated ring having 5, 6 or 7 ring atoms, said ring atoms comprising 1 or 2 oxygen atoms, the remaining ring atoms being carbon, selected from: dioxolanyl and dioxanyl;

X', Y' and Z' independently are selected from the group consisting of:
- (a) hydrogen,
- (b) $C_{1-7}$alkyl,
- (c) $C_{2-6}$alkenyl,
- (d) halogen,
- (e) $-(CH_2)_m-NR^6R^7$, wherein $R^6$, $R^7$, and m are as defined above,
- (f) $-CN$,
- (g) $-CHO$,
- (h) $-CF_3$,
- (i) $-SR^8$, wherein $R^8$ is hydrogen, $C_{1-6}$alkyl, trifluoromethyl, or phenyl, (j) —SOR⁸, wherein R⁸ is as defined above, (k) —SO₂R⁸, wherein R⁸ is as defined above, (l) —CONR⁶R⁷, wherein R⁶ and R⁷ are as defined above, (m) R⁹O(CH₂)ₘ— wherein R⁹ and m are as defined above, (n) —CH(OR¹⁵)(OR¹⁶), wherein R¹⁵ and R¹⁶ are as defined above, (o)

wherein R⁹ and m are as defined above, (p)

wherein R⁹ and m are as defined above, and (q) —R¹¹;

n is 1 or 2; heteroaryl, as used herein in the claim is: acridine, carbazole, cinnoline, dibenzofuran, dibenzothiophene, quinoxaline, pyrrazole, benzoxazole, indole, imidazole, thiazole, benzothiazole, benzotriazole, furan, benzofuran, benzimidazole, quinoline, isoquinoline, oxazole, pyrazine, pyridazine, pyridine, pyrimidine and pyrrole;

with the proviso that if: A is Ar—B—, Ar is substituted phenyl in which the substituents are X, Y and Z, B is a bond, X is hydrogen, and Y is HO—, then Z is other than CH₃O— or R⁹CO₂, wherein R⁹ is a defined above;

and pharmaceutically acceptable salts thereof.

2. The compound according to claim 1 wherein the absolute configuration of Formula I is as defined in Formula III:

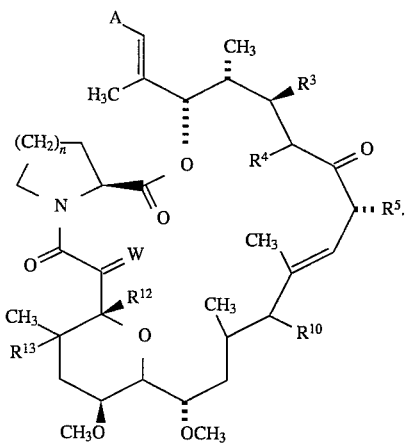

3. The compound of claim 1 wherein heteroaryl is selected from the group consisting of:

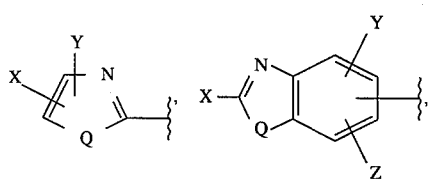

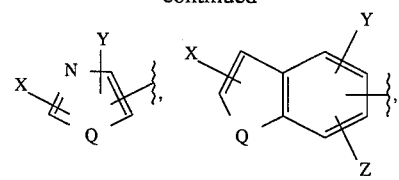

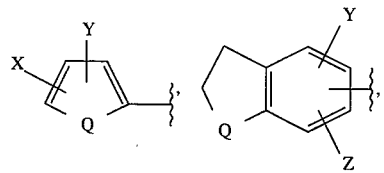

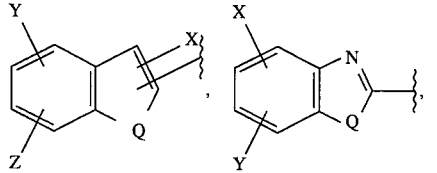

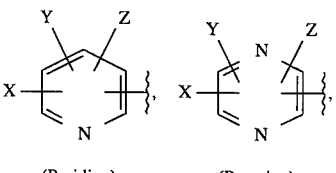

(Pyridazine)

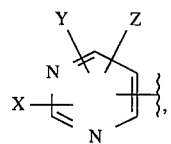

(Pyridine)     (Pyrazine)

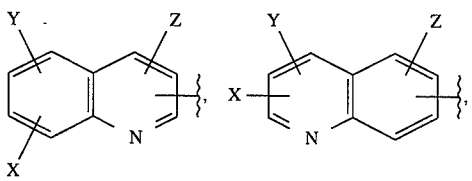

(Pyrimidine)

(Quinoline)

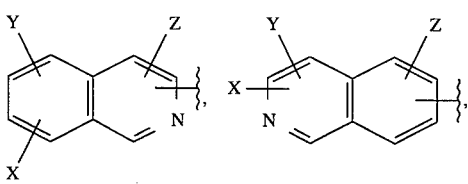

(Isoquinoline)

-continued

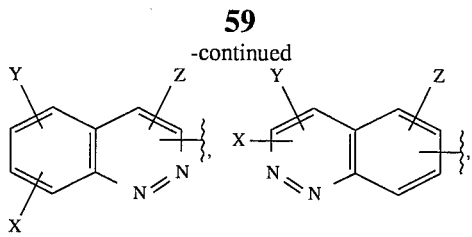

(Cinnoline)

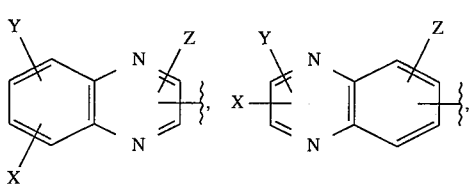

(Quinoxaline)

wherein Q is —N(X)—, —O—, —S—, —SO—, or —SO₂—, and X, Y, and Z are as defined in claim 1.

4. The compound of claim 3 wherein heteroaryl is selected from the group consisting of:

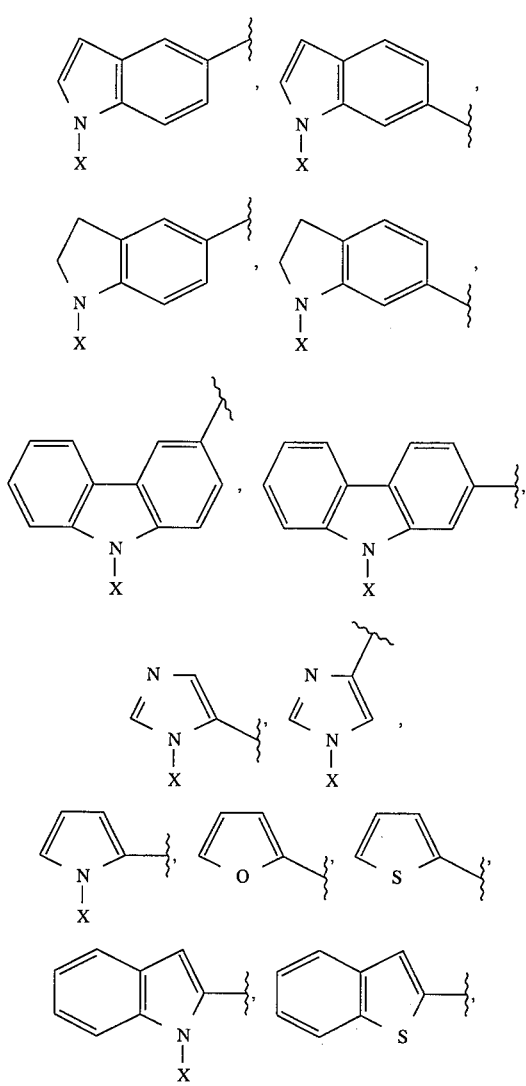

wherein X is defined in claim 1.

5. The compound of claim 1 wherein heteroaryl is:

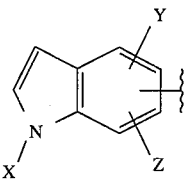

or

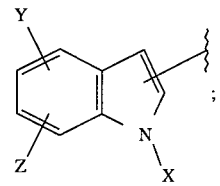

wherein X, Y, and Z are as defined in claim 1.

6. The compound of claim 1 wherein:

A is Ar—B—Ar'—, wherein Ar is heteroaryl, Ar' is phenyl, and B is —O—, $R^2$ is selected from:

(1) hydrogen, (2) methyl, (3) ethyl, (4) propyl, (5) allyl, (6) —$R^{11}$, (7) —$C_{2-3}$alkyl—OH; and (8) —$C_{2-3}$alkyl—OR$^{11}$;

$R^3$ is selected from:

(1) hydrogen, (2) hydroxy, (3) —OR$^{11}$, or $R^3$ and $R^4$ taken together form a double bond;

$R^{10}$ is hydrogen, hydroxy, fluoro, or —OR$^{11}$;

W is O; and n is 2.

7. The compound of claim 1 of the formula X or XI:

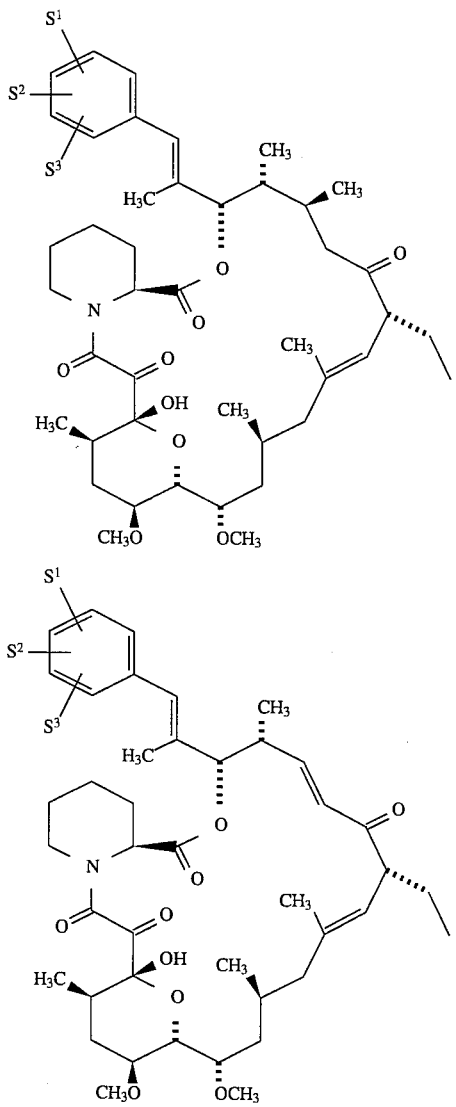

wherein $S^1$, $S^2$, and $S^3$ are selected from the following groups of substituents:

| $S^1$ | $S^2$ | $S^3$ |
|---|---|---|
| 3-H | 4-H | 5-H |
| 3-H | 4-OH | 5-H |
| 3-OH | 4-OH | 5-H |
| 3-OCH$_3$ | 4-OH | 5-H |
| 3-OEt | 4-OH | 5-H |
| 3-Oallyl | 4-OH | 5-H |
| 3-Opropyl | 4-OH | 5-H |
| 3-OH | 4-OCH$_3$ | 5-H |
| 3-OH | 4-OEt | 5-H |
| 3-OH | 4-O-allyl | 5-H |
| 3-OH | 4-O-propyl | 5-H |
| 3-OCH$_3$ | 4-C$_6$H$_5$—O— | 5-H |
| 3-OCH$_3$ | 4-(4-CH$_3$OC$_6$H$_4$O)— | 5-H |
| 3-OCH$_3$ | 4-(4-HOC$_6$H$_4$O)— | 5-H |
| 3-OCH$_3$ | 4-(4-ClC$_6$H$_4$O)— | 5-H |
| 3-OCH$_3$ | 4-[4-(CH$_3$)$_2$NC$_6$H$_4$O]— | 5-H |
| 3-OCH$_3$ | 4-[4-(Et)$_2$NC$_6$H$_4$O]— | 5-H |
| 3-C$_6$H$_4$O— | 4-OCH$_3$ | 5-H |
| 3-(4-CH$_3$OC$_6$H$_4$O)— | 4-OCH$_3$ | 5-H |
| 3-(4-HOC$_6$H$_4$O)— | 4-OCH$_3$ | 5-H |
| 3-(4-ClC$_6$H$_4$O)— | 4-OCH$_3$ | 5-H |
| 3-[4-(CH$_3$)$_2$NC$_6$H$_4$O]— | 4-OCH$_3$ | 5-H |
| 3-[4-(Et)$_2$NC$_6$H$_4$O]— | 4-OCH$_3$ | 5-H |
| 3-OH | 4-OH | 5-OH |
| 3-OCH$_3$ | 4-OH | 5-OH |
| 3-OCH$_3$ | 4-OCH$_3$ | 5-OH |
| 3-OCH$_3$ | 4-OCH$_3$ | 5-OCH$_3$ |
| 3-OEt | 4-OH | 5-OH |
| 3-OEt | 4-OH | 5-OH |
| 3-OEt | 4-OEt | 5-OEt |
| 3-OCH$_3$ | 4-OH | 5-C$_6$H$_5$—O— |
| 3-OCH$_3$ | 4-OH | 5-(4-CH$_3$OC$_6$H$_4$O)— |
| 3-OCH$_3$ | 4-OH | 5-(4-HOC$_6$H$_4$O)— |
| 3-OCH$_3$ | 4-OH | 5-(4-ClC$_6$H$_4$O)— |
| 3-OCH$_3$ | 4-OH | 5-[4-(CH$_3$)$_2$NC$_6$H$_4$O]— |
| 3-OCH$_3$ | 4-OH | 5-[4-(Et)$_2$NC$_6$H$_4$O]— |
| 3-OCH$_3$ | 4-OCH$_3$ | 5-C$_6$H$_5$O— |
| 3-OCH$_3$ | 4-OCH$_3$ | 5-(4-CH$_3$OC$_6$H$_4$O)— |
| 3-OCH$_3$ | 4-OCH$_3$ | 5-(4-HOC$_6$H$_4$O)— |
| 3-OCH$_3$ | 4-OCH$_3$ | 5-(4-ClC$_6$H$_4$O)— |
| 3-OCH$_3$ | 4-OH | 5-[4-(CH$_3$)$_2$NC$_6$H$_4$O]— |
| 3-OCH$_3$ | 4-OCH$_3$ | 5-[4-(Et)$_2$NC$_6$H$_4$O]— |
| 3-OEt | 4-OH | 5-C$_6$H$_5$O— |
| 3-OEt | 4-OH | 5-(4-CH$_3$OC$_6$H$_4$O)— |
| 3-OEt | 4-OH | 5-(4-HOC$_6$H$_4$O)— |
| 3-OEt | 4-OH | 5-(4-ClC$_6$H$_4$O)— |
| 3-OEt | 4-OH | 5-[4-(CH$_3$)$_2$NC$_6$H$_4$O]— |
| 3-OEt | 4-OH | 5-[4-(Et)$_2$NC$_6$H$_4$O]— |
| 3-OEt | 4-OEt | 5-C$_6$H$_5$O— |
| 3-OEt | 4-OH | 5-(4-CH$_3$OC$_6$H$_4$O)— |
| 3-OEt | 4-OH | 5-(4-HOC$_6$H$_4$O)— |
| 3-OEt | 4-OH | 5-(4-ClC$_6$H$_4$O)— |
| 3-OEt | 4-OH | 5-[4-(CH$_3$)$_2$NC$_6$H$_4$O]— |
| 3-OEt | 4-OH | 5-[4-(Et)$_2$NC$_6$H$_4$O]— |
| 3-OCH$_3$ | 4-(3-CH$_3$OC$_6$H$_4$O)— | 5-H |
| 3-OCH$_3$ | 4-(3-HOC$_6$H$_4$O)— | 5-H |
| 3-OCH$_3$ | 4-(3-ClC$_6$H$_4$O)— | 5-H |
| 3-OCH$_3$ | 4-[3-(CH$_3$)$_2$NC$_6$H$_4$O]— | 5-H |
| 3-OCH$_3$ | 4-[3-(Et)$_2$NC$_6$H$_4$O]— | 5-H |
| 3-(3-CH$_3$OC$_6$H$_4$O)— | 4-OCH$_3$ | 5-H |
| 3-(3-HOC$_6$H$_4$O)— | 4-OCH$_3$ | 5-H |
| 3-(3-ClC$_6$H$_4$O)— | 4-OCH$_3$ | 5-H |
| 3-[3-(CH$_3$)$_2$NC$_6$H$_4$O]— | 4-OCH$_3$ | 5-H |
| 3-[3-(Et)$_2$NC$_6$H$_4$O]— | 4-OCH$_3$ | 5-H |
| 3-OCH$_3$ | 4-OH | 5-[3-CH$_3$OC$_6$H$_4$O)— |
| 3-OCH$_3$ | 4-OH | 5-[3-HOC$_6$H$_4$O)— |
| 3-OCH$_3$ | 4-OH | 5-[3-ClC$_6$H$_4$O)— |
| 3-OCH$_3$ | 4-OH | 5-[3-(CH$_3$)$_2$NC$_6$H$_4$O]— |
| 3-OCH$_3$ | 4-OH | 5-[3-(Et)$_2$NC$_6$H$_4$O]— |
| 3-OCH$_3$ | 4-OCH$_3$ | 5-(3-CH$_3$OC$_6$H$_4$O)— |
| 3-OCH$_3$ | 4-OCH$_3$ | 5-(3-HOC$_6$H$_4$O)— |
| 3-OCH$_3$ | 4-OCH$_3$ | 5-(3-ClC$_6$H$_4$O)— |
| 3-OCH$_3$ | 4-OCH$_3$ | 5-[3-(CH$_3$)$_2$NC$_6$H$_4$O]— |
| 3-OCH$_3$ | 4-OCH$_3$ | 5-[3-(Et)$_2$NC$_6$H$_4$O]— |
| 3-OEt | 4-OH | 5-(3-CH$_3$OC$_6$H$_4$O)— |
| 3-OEt | 4-OH | 5-(3-HOC$_6$H$_4$O)— |
| 3-OEt | 4-OH | 5-(3-ClC$_6$H$_4$O)— |
| 3-OEt | 4-OH | 5-[3-(CH$_3$)$_2$NC$_6$H$_4$O]— |
| 3-OEt | 4-OH | 5-[3-(Et)$_2$NC$_6$H$_4$O]— |
| 3-OEt | 4-OEt | 5-(3-CH$_3$OC$_6$H$_4$O)— |
| 3-OEt | 4-OEt | 5-(3-HOC$_6$H$_4$O)— |
| 3-OEt | 4-OEt | 5-(3-ClC$_6$H$_4$O)— |
| 3-OEt | 4-OEt | 5-[3-(CH$_3$)$_2$NC$_6$H$_4$O]— |
| 3-OEt | 4-OEt | 5-[3-(Et)$_2$NC$_6$H$_4$O]— |

| $S^1$ | $S^2$ |
|---|---|
| 3-OH | 4-(1-H-indol-5-yl)—O— |
| 3-OH | 4-(1-CH$_3$-indol-5-yl)—O— |
| 3-OH | 4-(—CH$_3$CH$_2$-indol-5-yl)—O— |
| 3-OH | 4-(HO—CH$_2$CH$_2$-indol-5-yl)—O— |
| 3-OH | 4-(—HO—CH$_2$CH$_2$CH$_2$-indol-5-yl)—O— |
| 3-OH | 4-(—M$^+$¯O(HO)PO—O—CH$_2$CH$_2$-indol-5-yl)—O— |
| 3-OH | 4-(—M$^+$¯O(HO)PO—O—CH$_2$CH$_2$CH$_2$-indol-5-yl)—O— |
| 3-OCH$_3$ | 4-(1-H-indol-5-yl)—O— |
| 3-OCH$_3$ | 4-(1-CH$_3$-indol-5-yl)—O— |
| 3-OCH$_3$ | 4-(CH$_3$CH$_2$-indol-5-yl)—O— |
| 3-OCH$_3$ | 4(—HO—CH$_2$CH$_2$-indol-5-yl)—O— |

-continued

| S¹ | S² |
|---|---|
| 3-OCH₃ | 4-(—HO—CH₂CH₂CH₂-indol-5-yl)—O— |
| 3-OCH₃ | 4-(—M⁺⁻O(HO)PO—O—CH₂CH₂-indol-5-yl)—O— |
| 3-OCH₃ | 4-(—M⁺⁻O(HO)PO—O—CH₂CH₂CH₂-indol-5-yl)—O— |
| 3-OCH₂CH₃ | 4-(1-H-indol-5-yl)—O— |
| 3-OCH₂CH₃ | 4-(1-CH₃-indol-5-yl)—O— |
| 3-OCH₂CH₃ | 4-(—CH₃CH₂-indol-5-yl)—O— |
| 3-OCH₂CH₃ | 4-(—HO—CH₂CH₂-indol-5-yl)—O— |
| 3-OCH₂CH₃ | 4-(—HO—CH₂CH₂CH₂-indol-5-yl)—O— |
| 3-OCH₂CH₃ | 4-(—M⁺⁻O(HO)PO—O—CH₂CH₂-indol-5-yl)—O— |
| 3-OCH₂CH₃ | 4-(—M⁺⁻O(HO)PO—O—CH₂CH₂CH₂-indol-5-yl)—O— |
| 4-OH | 5-(1-H-indol-5-yl)—O— |
| 4-OH | 5-(1-CH₃-indol-5-yl)—O— |
| 4-OH | 5-(—CH₃CH₂-indol-5-yl)—O— |
| 4-OH | 5-(—HO—CH₂CH₂-indol-5-yl)—O— |
| 4-OH | 5-(—HO—CH₂CH₂CH₂-indol-5-yl)—O— |
| 4-OH | 5-(—M⁺⁻O(HO)PO—O—CH₂CH₂-indol-5-yl)—O— |
| 4-OH | 5-(—M⁺⁻O(HO)PO—O—CH₂CH₂CH₂-indol-5-yl)—O— |
| 4-OCH₃ | 5-(1-H-indol-5-yl)—O— |
| 4-OCH₃ | 5-(1-CH₃-indol-5-yl)—O— |
| 4-OCH₃ | 5-(—CH₃CH₂-indol-5-yl)—O— |
| 4-OCH₃ | 5-(—HO—CH₂CH₂-indol-5-yl)—O— |
| 4-OCH₃ | 5-(—HO—CH₂CH₂CH₂-indol-5-yl)—O— |
| 4-OCH₃ | 5-(—M⁺⁻O(HO)PO—O—CH₂CH₂-indol-5-yl)—O— |
| 4-OCH₃ | 5-(—M⁺⁻O(HO)PO—O—CH₂CH₂CH₂-indol-5-yl)—O— |
| 4-OCH₂CH₃ | 5-(1-H-indol-5-yl)—O— |
| 4-OCH₂CH₃ | 5-(1-CH₃-indol-5-yl)—O— |
| 4-OCH₂CH₃ | 5-(—CH₃CH₂-indol-5-yl)—O— |
| 4-OCH₂CH₃ | 5-(—HO—CH₂CH₂-indol-5-yl)—O— |
| 4-OCH₂CH₃ | 5-(—HO—CH₂CH₂CH₂-indol-5-yl)—O— |
| 4-OCH₂CH₃ | 5-(—M⁺⁻O(HO)PO—O—CH₂CH₂-indol-5-yl)—O— |
| 4-OCH₂CH₃ | 5-(-M⁺⁻O(HO)PO—O—CH₂CH₂CH₂-indol-5-yl)—O— |
| 3-OH | 4-(1-H-indol-6-yl)—O— |
| 3-OH | 4-(1-CH₃-indol-6-yl)—O— |
| 3-OH | 4-(—CH₃CH₂-indol-6-yl)—O— |
| 3-OH | 4-(—HO—CH₂CH₂-indol-6-yl)—O— |
| 3-OH | 4-(—HO—CH₂CH₂CH₂-indol-6-yl)—O— |
| 3-OH | 4-(—M⁺⁻O(HO)PO—O—CH₂CH₂-indol-6-yl)—O— |
| 3-OH | 4-(—M⁺⁻O(HO)PO—O—CH₂CH₂CH₂-indol-6-yl)—O— |
| 3-OCH₃ | 4-(1-H-indol-6-yl)—O— |
| 3-OCH₃ | 4-(1-CH₃-indol-6-yl)—O— |
| 3-OCH₃ | 4-(—CH₃CH₂-indol-6-yl)—O— |
| 3-OCH₃ | 4-(—HO—CH₂CH₂-indol-6-yl)—O— |
| 3-OCH₃ | 4-(—HO—CH₂CH₂CH₂-indol-6-yl)—O— |
| 3-OCH₃ | 4-(—M⁺⁻O(HO)PO—O—CH₂CH₂-indol-6-yl)—O— |
| 3-OCH₃ | 4-(—M⁺⁻O(HO)PO—O—CH₂CH₂CH₂-indol-6-yl)—O— |
| 3-OCH₂CH₃ | 4-(1-H-indol-6-yl)—O— |
| 3-OCH₂CH₃ | 4-(1-CH₃-indol-6-yl)—O— |
| 3-OCH₂CH₃ | 4-(—CH₃CH₂-indol-6-yl)—O— |
| 3-OCH₂CH₃ | 4-(—HO—CH₂CH₂-indol-6-yl)—O— |
| 3-OCH₂CH₃ | 4-(—HO—CH₂CH₂CH₂-indol-6-yl)—O— |
| 3-OCH₂CH₃ | 4-(—M⁺⁻O(HO)PO—O—CH₂CH₂-indol-6-yl)—O— |
| 3-OCH₂CH₃ | 4-(—M⁺⁻O(HO)PO—O—CH₂CH₂CH₂-indol-6-yl)—O— |
| 4-OH | 5-(1-H-indol-6-yl)—O— |
| 4-OH | 5-(1-CH₃-indol-6-yl)—O— |
| 4-OH | 5-(—CH₃CH₂-indol-6-yl)—O— |
| 4-OH | 5-(—HO—CH₂CH₂-indol-6-yl)—O— |
| 4-OH | 5-(—HO—CH₂CH₂CH₂-indol-6-yl)—O— |
| 4-OH | 5-(—M⁺⁻O(HO)PO—O—CH₂CH₂-indol-6-yl)—O— |
| 4-OH | 5-(—M⁺⁻O(HO)PO—O—CH₂CH₂CH₂-indol-6-yl)—O— |
| 4-OCH₃ | 5-(1-H-indol-6-yl)—O— |
| 4-OCH₃ | 5-(1-CH₃-indol-6-yl)—O— |
| 4-OCH₃ | 5-(—CH₃CH₂-indol-6-yl)—O— |
| 4-OCH₃ | 5-(—HO—CH₂CH₂-indol-6-yl)—O— |
| 4-OCH₃ | 5-(—HO—CH₂CH₂CH₂-indol-6-yl)—O— |
| 4-OCH₃ | 5-(—M⁺⁻O(HO)PO—O—CH₂CH₂-indol-6-yl)—O— |
| 4-OCH₃ | 5-(—M⁺⁻O(HO)PO—O—CH₂CH₂CH₂-indol-6-yl)—O— |
| 4-OCH₂CH₃ | 5-(1-H-indol-6-yl)—O— |
| 4-OCH₂CH₃ | 5-(1-CH₃-indol-6-yl)—O— |
| 4-OCH₂CH₃ | 5-(—CH₃CH₂-indol-6-yl)—O— |
| 4-OCH₂CH₃ | 5-(—HO—CH₂CH₂-indol-6-yl)—O— |
| 4-OCH₂CH₃ | 5-(—HO—CH₂CH₂CH₂-indol-6-yl)—O— |
| 4-OCH₂CH₃ | 5-(—M⁺⁻O(HO)PO—O—CH₂CH₂-indol-yl)—O— |
| 4-OCH₂CH₃ | 5-(—M⁺⁻O(HO)PO—O—CH₂CH₂CH₂-indol-6-yl)—O— |
| 4-OH | 3-[C₆H₄—COCH₂—O—] |
| 4-OCH₃ | 3-[C₆H₄—COCH₂—O—] |
| 4-OEt | 3-[C₆H₄—COCH₂—O—] |
| 4-OH | 3-[3-CH₃C₆H₄—COCH₂—O—] |
| 4-OCH₃ | 3-[3-CH₃C₆H₄—COCH₂—O—] |
| 4-OEt | 3-[3-CH₃C₆H₄—COCH₂—O—] |
| 4-OH | 3-[3-CH₃OC₆H₄—COCH₂—O—] |
| 4-OCH₃ | 3-[3-CH₃OC₆H₄—COCH₂—O—] |
| 4-OEt | 3-[3-CH₃OC₆H₄—COCH₂—O—] |
| 4-OH | 3-[3-HOC₆H₄—COCH₂—O—] |
| 4-OCH₃ | 3-[3-HOC₆H₄—COCH₂—O—] |
| 4-OEt | 3-[3-HOC₆H₄—COCH₂—O—] |
| 4-OH | 3-[C₆H₄—CH(OH)CH₂—O—] |
| 4-OCH₃ | 3-[C₆H₄—CH(OH)CH₂—O—] |
| 4-OEt | 3-[C₆H₄—CH(OH)CH₂—O—] |
| 4-OH | 3-[3-CH₃C₆H₄—CH(OH)CH₂—O—] |
| 4-OCH₃ | 3-[3-CH₃C₆H₄—CH(OH)CH₂—O—] |
| 4-OEt | 3-[3-CH₃C₆H₄—CH(OH)CH₂—O—] |
| 4-OH | 3-[3-CH₃OC₆H₄—CH(OH)CH₂—O—] |
| 4-OCH₃ | 3-[3-CH₃OC₆H₄—CH(OH)CH₂—O—] |
| 4-OEt | 3-[3-CH₃OC₆H₄—CH(OH)CH₂—O—] |
| 4-OH | 3-[3-HOC₆H₄—CH(OH)CH₂—O—] |
| 4-OCH₃ | 3-[3-HOC₆H₄—CH(OH)CH₂—O—] |
| 4-OEt | 3-[3-HOC₆H₄—CH(OH)CH₂—O—] | and pharmaceutically acceptable salts thereof.

8. The compound of claim 1 of the formula XII, XIII XIV or XV:

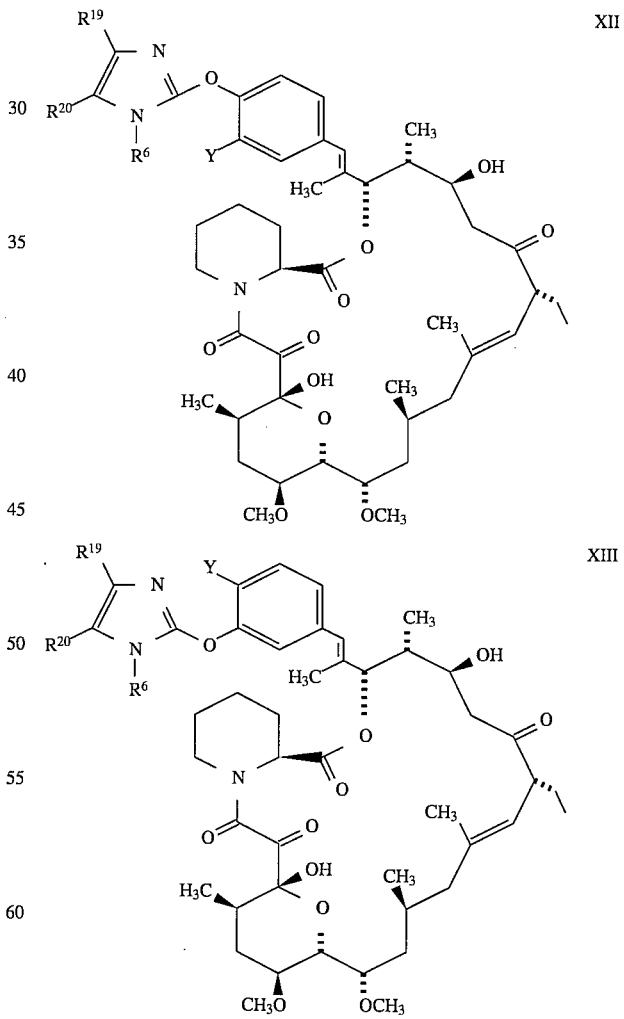

-continued

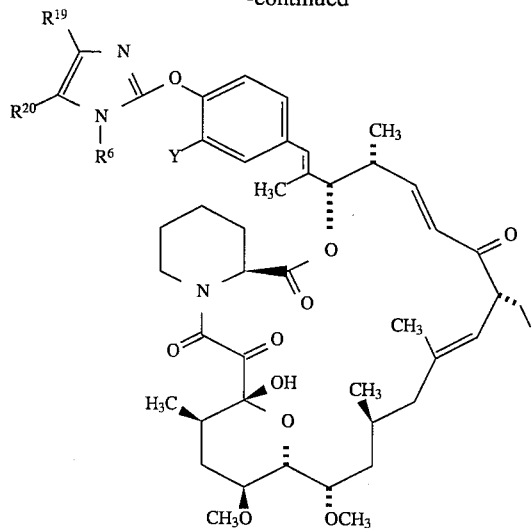

XIV

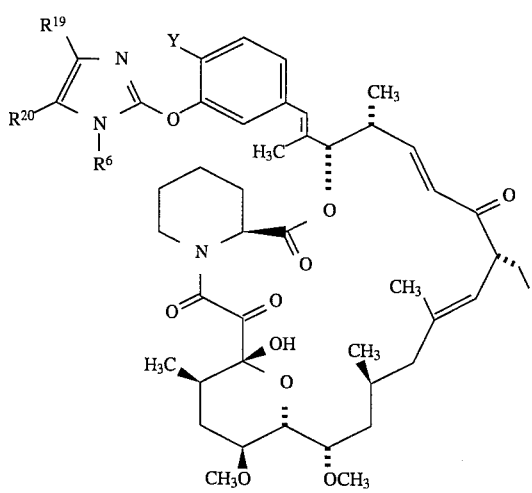

XV wherein R⁶, R¹⁹, R²⁰, and Y are selected from the following groups of substituents:

| Y | R⁶ | R¹⁹ | R²⁰ |
|---|---|---|---|
| OH | H | H | H |
| OH | H | H | C₆H₅— |
| OH | H | H | 3-ClC₆H₄— |
| OH | H | H | 4-ClC₆H₄— |
| OH | H | H | 3-BrC₆H₄— |
| OH | H | H | 4-BrC₆H₄— |
| OH | H | H | 3-HOC₆H₄— |
| OH | H | H | 4-HOC₆H₄— |
| OH | H | H | 3-CH₃OC₆H₄— |
| OH | H | H | 4-CH₃OC₆H₄— |
| OH | H | H | 3-CH₃CH₂OC₆H₄— |
| OH | H | H | 4-CH₃CH₂OC₆H₄— |
| OH | H | H | 3-CH₃CH₂— |
| OH | H | H | 4-CH₃CH₂— |
| OH | H | H | 3-HOCH₂CH₂— |
| OH | H | H | 4-HOCH₂CH₂— |
| OCH₃ | H | H | H |
| OCH₃ | H | H | C₆H₅— |
| OCH₃ | H | H | 3-ClC₆H₄— |
| OCH₃ | H | H | 4-ClC₆H₄— |
| OCH₃ | H | H | 3-BrC₆H₄— |
| OCH₃ | H | H | 4-BrC₆H₄— |
| OCH₃ | H | H | 3-HOC₆H₄— |
| OCH₃ | H | H | 4-HOC₆H₄— |
| OCH₃ | H | H | 3-CH₃OC₆H₄— |
| 3-OCH₃ | H | H | 4-CH₃OC₆H₄— |
| OCH₃ | H | H | 3-CH₃CH₂OC₆H₄— |
| OCH₃ | H | H | 4-CH₃CH₂OC₆H₄— |
| OCH₃ | H | H | 3-CH₃CH₂CH₂— |
| OCH₃ | H | H | 4-CH₃CH₂CH₂— |
| OCH₃ | H | H | 3-HOCH₂CH₂— |
| OCH₃ | H | H | 4-HOCH₂CH₂— |
| OCH₂CH₃ | H | H | H |
| OCH₂CH₃ | H | H | C₆H₅— |
| OCH₂CH₃ | H | H | 3-ClC₆H₄— |
| OCH₂CH₃ | H | H | 4-ClC₆H₄— |
| OCH₂CH₃ | H | H | 3-BrC₆H₄— |
| OCH₂CH₃ | H | H | 4-BrC₆H₄— |
| OCH₂CH₃ | H | H | 3-HOC₆H₄— |
| OCH₂CH₃ | H | H | 4-HOC₆H₄— |
| OCH₂CH₃ | H | H | 3-CH₃OC₆H₄— |
| OCH₂CH₃ | H | H | 4-CH₃OC₆H₄— |
| OCH₂CH₃ | H | H | 3-CH₃CH₂OC₆H₄— |
| OCH₂CH₃ | H | H | 4-CH₃CH₂OC₆H₄— |
| OCH₂CH₃ | H | H | 3-CH₃CH₂CH₂— |
| OCH₂CH₃ | H | H | 4-CH₃CH₂CH₂— |
| OCH₂CH₃ | H | H | 4-HOCH₂CH₂— | and pharmaceutically acceptable salts thereof.

9. The compound of claim 1 of the formula XVI or XVII:

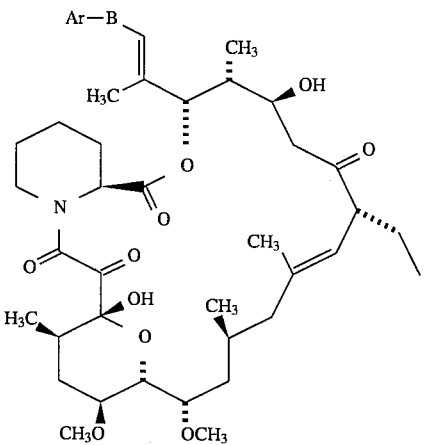

XVI

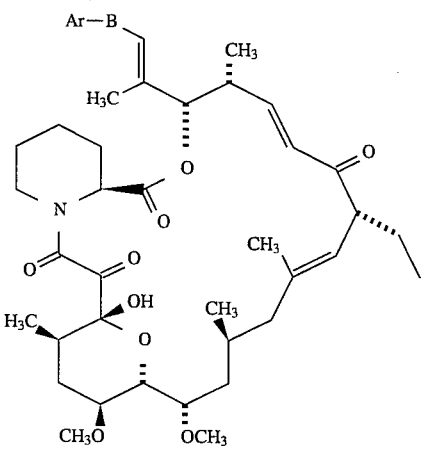

XVII wherein Ar is selected from the group consisting of:

3—CH₃O—C₆H₄—,
3—HO—C₆H₄—,
3—Cl—C₆H₄—,
3—(CH₃)₂N—C₆H₄—,
3—(Et)₂N—C₆H₄—,
4—CH₃O—C₆H₄—,
4—HO—C₆H₄—,
4—Cl—C₆H₄—,

4—(CH$_3$)$_2$N—C$_6$H$_4$—,
4—(Et)$_2$N—C$_6$H$_4$—,
1-H-indol-5-yl-,
1-CH$_3$-indol-5-yl-,
1-CH$_3$CH$_2$-indol-5-yl)-,
1-HO-CH$_2$CH$_2$-indol-5-yl)-,
1-HO-CH$_2$CH$_2$CH$_2$-indol-5-yl)-,
1-[-M$^+$—O(HO)PO—O—CH$_2$CH$_2$]-indol-5-yl-,
1-[-M$^+$—O(HO)PO—O—CH$_2$CH$_2$CH$_2$]-indol-5-yl-,
1-H-indol-6-yl-,
1-CH$_3$-indol-6-yl-,
1-CH$_3$CH$_2$-indol-6-yl)-,
1-HO—CH$_2$CH$_2$-indol-6-yl)-,
1-HO—CH$_2$CH$_2$CH$_2$-indol-6-yl)-,
1-[-M$^+$—O(HO)PO—O—CH$_2$CH$_2$]-indol-6-yl-, and
1-[-M$^+$—O(HO)PO—O—CH$_2$CH$_2$CH$_2$]-indol-6-yl-;
B is selected from the group consisting of:
—NHCO—,
—O$_2$C—,
—CH$_2$—,
—CH$_2$CH$_2$—,
—CH$_2$CH$_2$CH$_2$—,
—CH=CH—,
—(CH$_3$)C=CH—,
—CH=C(CH$_3$)—,
—(CH$_3$)C=(CCH$_3$)—,
—CH$_2$—CH=CH—,
—CH$_2$—(CH$_3$)C=CH—,
—CH$_2$—CH=C(CH$_3$)—,
—CH$_2$—(CH$_3$)C=(CCH$_3$)—,
—CH$_2$—CH$_2$—CH=CH—,
—CH$_2$—CH$_2$—(CH$_3$)C=CH—,
—CH$_2$—CH$_2$—CH=C(CH$_3$)—,
—CH$_2$—CH(CH$_3$)—CH=CH—,
—CH$_2$—CH(CH$_3$)—(CH$_3$)C=CH—,
—CH$_2$—CH(CH$_3$)—CH=C(CH$_3$)—,
—CH(CH$_3$)—CH$_2$—CH=CH—,
—CH(CH$_3$)—CH$_2$—(CH$_3$)C=CH—,
—CH(CH$_3$)—CH$_2$—CH=C(CH$_3$)—,
—CH$_2$—CH(OCH$_3$)—CH=CH—,
—CH$_2$—CH(OCH$_3$)—(CH$_3$)C=CH—,
—CH$_2$—CH(OCH$_3$)—CH=C(CH$_3$)—,
—CH(OCH$_3$)—CH$_2$—CH=CH—,
—CH(OCH$_3$)—CH$_2$—(CH$_3$)C=CH—,
—CH(OCH$_3$)—CH$_2$—CH=C(CH$_3$)—,
—CH$_2$—CH$_2$—CH$_2$—CH=CH—,
—CH$_2$—CH$_2$—CH(CH$_3$)—CH=CH—,
—CH$_2$—CH$_2$—CH(CH$_3$)—(CH$_3$)C=CH—,
—CH$_2$—CH$_2$—CH(CH$_3$)—CH=C(CH$_3$)—,
—CH$_2$—CH(CH$_3$)—CH$_2$—CH=CH—,
—CH$_2$—CH(CH$_3$)—CH$_2$—(CH$_3$)C=CH—,
—CH$_2$—CH(CH$_3$)—CH$_2$—CH=C(CH$_3$)—,
—CH$_2$—CH$_2$—CH(OCH$_3$)—CH=CH—,
—CH$_2$—CH$_2$—CH(OCH$_3$)—(CH$_3$)C=CH—,
—CH$_2$—CH$_2$—CH(OCH$_3$)—CH=C(CH$_3$)—,
—CH$_2$—CH(OCH$_3$)—CH$_2$—CH=CH—,
—CH$_2$—CH(OCH$_3$)—CH$_2$—(CH$_3$)C=CH—,
—CH$_2$—CH(OCH$_3$)—CH$_2$—CH=C(CH$_3$)—,
—CH$_2$—CH(CH$_3$)—CH(OCH$_3$)—CH=CH—,
—CH$_2$—CH(CH$_3$)—CH(OCH$_3$)—(CH$_3$)C=CH—,
—CH$_2$—CH(CH$_3$)—CH(OCH$_3$)—CH=C(CH$_3$)—,
—CH$_2$—CH(OCH$_3$)—CH(CH$_3$)—CH=CH—,
—CH$_2$—CH(OCH$_3$)—CH(CH$_3$)—(CH$_3$)C=CH—, and
—CH$_2$—CH(OCH$_3$)—CH(CH$_3$)—CH=C(CH$_3$)—;
and pharmaceutically acceptable salts thereof.

* * * * *